US010544082B2

(12) United States Patent
Ozmeral et al.

(10) Patent No.: US 10,544,082 B2
(45) Date of Patent: Jan. 28, 2020

(54) METHOD TO PRODUCE ACRYLIC ACID WITH ACETALDEHYDE AS THE MAIN BY-PRODUCT

(71) Applicant: PTT GLOBAL CHEMICAL PUBLIC COMPANY LIMITED, Bangkok (TH)

(72) Inventors: Cenan Ozmeral, Flagler Beach, FL (US); Rajesh Dasari, Lincoln, MA (US); Ramnik Singh, Winchester, MA (US); Yu Noda, Prague (CZ); Robert M. Rioux, State College, PA (US); Yuriy Roman-Leshkov, Cambridge, MA (US)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 0 days.

(21) Appl. No.: 15/580,041

(22) PCT Filed: Jun. 10, 2016

(86) PCT No.: PCT/US2016/036819
§ 371 (c)(1),
(2) Date: Dec. 6, 2017

(87) PCT Pub. No.: WO2016/201181
PCT Pub. Date: Dec. 15, 2016

(65) Prior Publication Data
US 2018/0134647 A1    May 17, 2018

Related U.S. Application Data

(60) Provisional application No. 62/173,499, filed on Jun. 10, 2015.

(51) Int. Cl.
| C07C 51/377 | (2006.01) |
|---|---|
| C07C 45/54 | (2006.01) |
| B01J 29/08 | (2006.01) |
| B01J 29/40 | (2006.01) |
| B01J 29/60 | (2006.01) |
| B01J 29/70 | (2006.01) |
| B01J 35/00 | (2006.01) |
| B01J 29/18 | (2006.01) |
| B01J 37/02 | (2006.01) |
| B01J 37/30 | (2006.01) |
| B01J 27/18 | (2006.01) |

(52) U.S. Cl.
CPC ......... *C07C 51/377* (2013.01); *B01J 27/1806* (2013.01); *B01J 29/082* (2013.01); *B01J 29/084* (2013.01); *B01J 29/18* (2013.01); *B01J 29/40* (2013.01); *B01J 29/60* (2013.01); *B01J 29/7007* (2013.01); *B01J 35/002* (2013.01); *B01J 37/0201* (2013.01); *B01J 37/30* (2013.01); *C07C 45/54* (2013.01); *B01J 2229/123* (2013.01); *B01J 2229/183* (2013.01); *Y02P 20/588* (2015.11)

(58) Field of Classification Search
CPC .... B01J 27/1806; B01J 29/082; B01J 29/084; B01J 29/18; B01J 29/40; B01J 29/60; B01J 29/7007; B01J 35/002; B01J 37/0201; B01J 37/30; B01J 2229/123; B01J 2229/183; C07C 45/54; C07C 51/377
See application file for complete search history.

(56) References Cited

FOREIGN PATENT DOCUMENTS

WO    WO2013134385    *   9/2013

OTHER PUBLICATIONS

Standard Test Method for Determination of Catalyst Acidity by Ammonia Chemisoportion, ASTM International, pp. 1-3 (Year: 2018).*

* cited by examiner

*Primary Examiner* — Paul A Zucker
(74) *Attorney, Agent, or Firm* — Oblon, McClelland, Maier & Neustadt, L.L.P.

(57) ABSTRACT

Described herein are solid acid catalysts and the methods for catalytically preparing α,β-unsaturated carboxylic acids and/or esters thereof. In one aspect, a zeolite catalyst may be used. The catalyst may, in certain embodiments, be modified to improve the selectivity and/or conversion of a reaction. For instance, a catalyst may be modified by ion exchange to achieve a desirable acidity profile in order to achieve high level of conversion of reactants and selectivity for desirable products of the catalytic reaction. In another aspect, a variety of feed stocks (e.g., starting compositions) may be used including an α-hydroxycarboxylic acid, an α-hydroxycarboxylic acid ester, a β-hydroxycarboxylic acid, a β-hydroxycarboxylic acid ester, cyclic esters thereof (e.g., lactide), and combinations thereof.

16 Claims, 31 Drawing Sheets

Fresh and Spent Catalyst 1.0 K2 (pH13)/NaY441    1.25 K2/NaZSM5    4.0 K1/NaZSM5

US 10,544,082 B2

METHOD TO PRODUCE ACRYLIC ACID WITH ACETALDEHYDE AS THE MAIN BY-PRODUCT

CROSS REFERENCE TO RELATED APPLICATION

This application is the U.S. national stage application of International Patent Application No. PCT/US2016/036819 filed on Jun. 10, 2016, which claims priority to U.S. Provisional Application Ser. No. 62/173,499 filed on Jun. 10, 2015.

FIELD OF THE INVENTION

The present invention is in the field of catalytically preparing α, β-unsaturated carboxylic acid and/or esters thereof from α-hydroxycarboxylic acid or β-hydroxycarboxylic acid and esters thereof.

BACKGROUND OF THE INVENTION

Acrylic acid, an α, β-unsaturated carboxylic acid, is an important commodity chemical. When reacted with an alcohol it forms the corresponding ester. Acrylic acid and its esters readily combine with themselves or other monomers by reacting at their double bond to form homopolymers or copolymers useful in the manufacture of various plastics, coatings, adhesives, elastomers, floor polishes and paints.

Traditionally, acrylic acid is derived from fossil hydrocarbon resources. The most widely used process for acrylic acid manufacturing is the vapor phase oxidation of propylene, which is a byproduct of ethylene and gasoline production, involving two reactions in series, using two separate catalysts. The other method for acrylic acid manufacturing involves hydroxycarboxylation of acetylene. This method utilizes nickel carbonyl and high pressure carbon monoxide, both of which are expensive and considered environmentally unfriendly. In addition, there is a concern in the continued use of fossil hydrocarbon reserves in the manufacture of acrylic acid as it contributes to an increase in the greenhouse gas emission. As a result, there is a growing interest in the catalytic dehydration of lactic acid and 3-hydroxypropionic acid as an alternative route to produce acrylic acid because lactic acid and 3-hydroxypropionic acid can be derived from renewable, biological resources like sugar cane, corn and cellulosic feedstock.

A number of inorganic solid acid catalysts have been reported to be useful in the production of acrylic acid from lactic acid at elevated temperature. The production of acrylic acid from lactic acid involves removal of hydroxyl group from alpha carbon atom and hydrogen atom from the adjacent beta carbon atom. Thus, it would appear that the efficiency of this chemical conversion from lactic acid to acrylic acid would depend on the rate constant for the dehydration reaction. But in reality, the challenge in increasing the efficiency of dehydration of lactic acid leading to acrylic acid production depends on inhibiting a number of competing side reactions. As illustrated in FIG. 1, under the conditions reported to be favorable for dehydration of lactic acid, four other competing chemical reactions namely decarbonylation, decarboxylation, condensation and reduction are known to occur either in parallel or in series. Acetaldehyde formation occurs when lactic acid undergoes decarboxylation or decarbonylation reaction. Condensation reaction involving lactic acid at elevated temperature results in the formation of 2,3-pentanedione. Reduction reaction involving lactic acid at elevated temperature results in the formation of propionic acid and 1,2-propanediol. Thus in a catalytic reaction involving solid acid catalysts at elevated temperatures, lactic acid yields a product mixture comprising acrylic acid, acetaldehyde, hydroxy acetone, 2,3-Pentanedione, propionic acid and 1,2-propanediol. Fractional distillation process may be followed to separate acrylic acid from the resulting product mixture. However, the process step involving fractional distillation adds additional cost to acrylic acid manufacturing process. Therefore, it is desirable to develop a catalytic process for manufacturing acrylic acid involving catalytic dehydration of lactic acid where the formation of byproducts such as 2,3-pentanedione, propionic acid, hydroxy acetone and acetaldehyde are either completely eliminated or significantly reduced.

SUMMARY OF THE INVENTION

The invention relates to a process for preparing an α, β-unsaturated carboxylic acid and/or ester thereof via vapor phase dehydration reaction involving a suitable reactant and a solid acid catalyst with a minimum 80% conversion of reactant and a minimum 70% selectivity for α, β-unsaturated carboxylic acid and/or ester thereof. In the present invention, only acetaldehyde with maximum selectivity of 20% is formed as a byproduct from this vapor phase dehydration reaction. The other byproducts such 2,3-pentanedione and propionic acid are produced in very minimal amount in this vapor phase dehydration reaction according to the present invention and show selectivity of less than 1.0%.

The reactant suitable for this vapor phase dehydration reaction is selected from the group consisting of an α-hydroxycarboxylic acid, an α-hydroxycarboxylic acid ester, a β-hydroxycarboxylic acid, a β-hydroxycarboxylic acid ester and a lactide, acetoxylated forms of any of these acids or ester and any combination thereof. In one aspect of the present invention, the reactants used in the vapor phase dehydration reaction are obtained from biomass through biological fermentation involving microbial catalyst. In the prepared embodiment of the present invention, biomass-derived α-hydroxycarboxylic acid and/or esters thereof are used as the reactant.

The solid acid catalyst suitable for the present invention comprises either a porous aluminosilicate material or carbon based material or a metal oxide material as a support and at least one active salt. The porous aluminosilicate material suitable for the present invention has silica to aluminum ratio in the range of 1 to 150. The porous aluminosilicate material support useful for the present invention is selected from a group consisting of Zeolite A, Zeolite B, Zeolite L, Zeolite X, Zeolite Y, Zeolite ZK-4, Zeolite ZSM-5 and a combination thereof. In one aspect of the present invention, the Zeolite ZSM-5 is used as a preferred support component of the solid acid catalyst. The carbon based material support is selected from a group of charcoals, activated carbons, graphite and graphene. The metal oxide support is selected from a group of $ZnO$, $ZrO_2$, $SiO_2$, $Al_2O_3$, $TiO_2$, $K_2O$, $Na_2O$, $MgO$, $CaO$, $LiO_2$, $Ag_2O$, $FeO$, $Fe_2O_3$, $CrO_3$, $CuO$, $Cu_2O$ and a combination thereof.

The active salt suitable for the present invention is represented by an inorganic salt, preferably a phosphate salt. In a preferred embodiment of the present invention, the potassium dihydrogen phosphate is used as an active salt in the catalytic vapor phase dehydration reaction.

The critical aspect of catalyst preparation according to the present invention is focused on maintaining an optimal balance between the acid and base properties of the catalyst system so that highest selectivity for the desired product is obtained. The porous aluminosilicate zeolites used as a support in the present invention are generally considered as solid acid catalyst. In one aspect of the present invention the surface acidity of the zeolite used as a support of the catalyst system is reduced through ion-exchange reaction. In the ion-exchange reaction according to the present invention the proton or ammonium ion associated with porous aluminosilicate material is replaced by one or more cations selected from a group consisting of $Li^+$, $Na^+$, $K^+$, $Cs^+$, $Mg^{2+}$, $Be^{2+}$, $Ba^{2+}$, $Ca^{2+}$, $La^{2+}$, $La^{3+}$, $Ce^{2+}$, $Ce^{3+}$, $Sm^{2+}$, $Sm^{3+}$, $Eu^{2+}$ and $Eu^{3+}$. As a result of this ion exchange reaction, the surface acidity of porous aluminosilicate material is reduced and such decrease in the surface acidity can be monitored by means of recording the temperature programmed desorption profile of the porous aluminosilicate material before and after ion exchange reaction.

The ion-exchanged zeolite material is subjected to salt impregnation process. In one aspect of the present invention the surface acidity of the ion exchanged porous aliminosilicate material is further reduced by means of impregnating one or more of the inorganic salt selected from a group consisting of a phosphate, a phosphite, an orthophosphate, a metaphosphate, a polyphosphate, a sulfate, a sulfite, a bisulfite, a bisulfate, a nitrate, a nitrite, a carbonate, a halide, a molybdate, a arsenate, a tungstate, a stanate, an antimonite and any combination thereof. In preferred aspect of the present invention, the ion exchanged porous aluminosilicate material is impregnated with an inorganic salt selected from a group consisting of a monosodium phosphate, disodium phosphate, a trisodium phosphate, a potassium phosphate, a sodium aluminum phosphate compound, and any combination thereof.

In one aspect of the present invention, inorganic acid salt impregnation is carried out through an incipient impregnation process. In another aspect of the present invention, the inorganic acid salt impregnation is carried out through a wet impregnation process.

In one embodiment of the present invention, the ion exchange reaction together with the salt impregnation process reduces the Brönsted acidity of the porous aluminosilicate material. In another embodiment of the present invention, the ion exchange reaction together with the salt impregnation process reduces the Lewis acidity of the porous aluminosilicate material.

In one aspect of the present invention, the catalytic dehydration reaction for preparing an α, β-unsaturated carboxylic acid and/or ester is performed in a reactor vessel comprising a reactor material comprising at least on selected from the group consisting of titanium, silanized stainless steel, quartz, and any combination thereof.

In another aspect of the present invention, the dehydration reaction for preparing an α, β-unsaturated carboxylic acid and/or ester occurs in the presence of a carrier gas selected from a group consisting of carbon dioxide, helium, nitrogen and any combination thereof.

In yet another aspect of the present invention, the dehydration reaction for preparing an α, β-unsaturated carboxylic acid and/or ester is carried in the temperature range of 250° C. to 400° C. and with carrier gas velocity in the range of 0.2 $hr^{-1}$ to about 1.5 $hr^{-1}$.

BRIEF DESCRIPTION OF THE DRAWINGS

The objects and features of the invention can be better understood with reference to the drawings described below, and the claims. The drawings are not necessarily to scale; emphasis instead generally being placed upon illustrating the principles of the invention. In the drawings, like numerals are used to indicate like parts throughout the various views.

DETAILED DESCRIPTION

Figure 1:
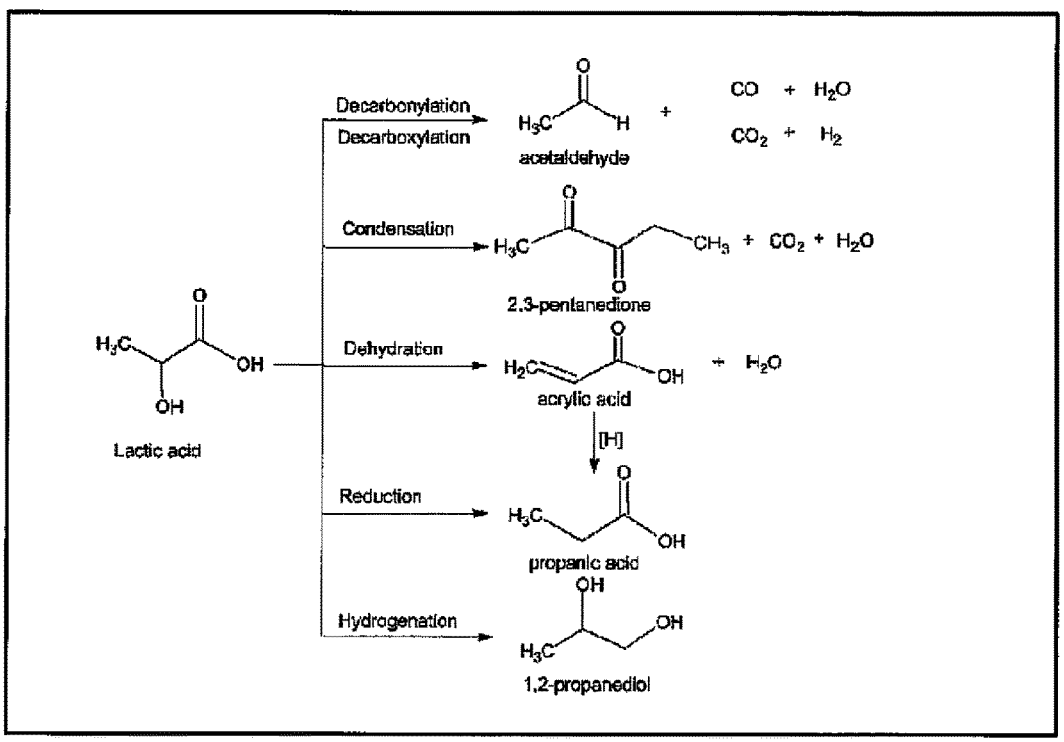
FIG. 1 Schematic depiction of reaction pathway for lactic acid conversion at elevated temperature in the presence of heterogeneous catalyst. Competing parallel and series chemical reactions limit the selectivity for the dehydration reaction to yield acrylic acid from lactic acid.

The present invention relates to a method of catalytically preparing α, β-unsaturated carboxylic acids and/or esters thereof using a reactant selected from the group consisting of an α-hydroxycarboxylic acid, an α-hydroxycarboxylic acid ester, a β-hydroxycarboxylic acid, a β-hydroxycarboxylic acid ester, and a cyclic ester thereof. More specifically, the present invention provides catalysts that are useful in the vapor phase dehydration of lactic acid with very high conversion and high level of selectivity for acrylic acid.

It should be noted that when "about" is used herein at the beginning of a numerical list, "about" modifies each number of the numerical list. It should be noted that in some numerical listings of ranges, some lower limits listed may be greater than some upper limits listed. One skilled in the art will recognize that the selected subset will require the selection of an upper limit in excess of the selected lower limit.

As used herein, the term "dehydration reaction" refers to the removal of water from a reactant. The term "dehydration reaction" is also known as "dehydroxylation reaction" in the art.

In some embodiments, an α-hydroxy carboxylic acid described herein (e.g., lactic acid and its derivatives) may be obtained from a fermentation broth. In some embodiments, a fermentation broth described herein may be derived from the cultures of the bacterial species including *Escherichia coli* and *Bacillus coagulans* selected for lactic acid production on a commercial scale. In some embodiments, a fermentation broth described herein may be derived from the culture fluid of the filamentous fungal species selected for lactic acid production. In some embodiments, a fermentation broth described herein may be derived from yeast species known to produce lactic acid in industrial scale. Microorganisms suitable for the production of lactic acid on a commercial scale may, in some embodiments, include *Escherichia coli*, *Bacillus coagulans*, *Lactobacillus delbruckii*, *L. bulgaricus*, *L. thermophilus*, *L. leichmanni*, *L. casei*, *L. fermentii*, *Streptococcus thermophilus*, *S. lactis*, *S. faecalils*, *Pediococcus* sp, *Leuconostoc* sp, *Bifidobacterium* sp, *Rhizopus oryzae* and a number of species of yeasts in industrial use. One skilled in the art with the benefit of this disclosure should recognize suitable combinations of any of the foregoing.

The fermentation process for producing α-hydroxy carboxylic acid like lactic acid may, in some embodiments, be a batch process, a continuous process, or a hybrid thereof. A large number of carbohydrate materials derived from natural resources can be used as a feedstock in conjunction with the fermentative production of α-hydroxy carboxylic acids described herein. For example, sucrose from cane and beet, glucose, whey containing lactose, maltose and dextrose from hydrolyzed starch, glycerol from biodiesel industry, and combinations thereof may be suitable for the fermentative production of α-hydroxy carboxylic acids described herein. Microorganisms may also be created with the ability to use pentose sugars derived from hydrolysis of cellulosic biomass in the production of α-hydroxy carboxylic acids described herein. In some embodiments, a microorganism with ability to utilize both 6-carbon containing sugars such as glucose and 5-carbon containing sugars such as xylose simultaneously in the production of lactic acid is a preferred biocatalyst in the fermentative production of lactic acid. In some embodiments, hydrolysate derived from cheaply available cellulosic material containing both C-5 carbon and C-6 carbon sugars and a biocatalyst capable of utilizing simultaneously C-5 and C-6 carbon sugars in the production of lactic acid is highly preferred from the point of producing low-cost lactic acid suitable for the conversion into acrylic acid and acrylic acid ester.

In some embodiments, fermentation broths for the production of lactic acid may include acid-tolerant homolactic acid bacteria. By "homolactic" it is meant that the bacteria strain produces substantially only lactic acid as the fermentation product. The acid-tolerant homolactic bacterium is typically isolated from the corn steep water of a commercial corn milling facility. An acid tolerant microorganism, which can also grow at elevated temperatures, may be preferred in some embodiments. In some preferred embodiments, microorganisms that can produce at least 4 g of lactic acid per liter (and more preferably 50 g of lactic acid per liter) of the fermentation fluid may be utilized in fermentation procedures described herein.

In some embodiments, the fermentation broth may be utilized at various points of production, e.g., after various unit operations have occurred like filtration, acidification, polishing, concentration, or having been processed by more than one of the aforementioned unit operations. In some embodiments, when the fermentation broth may contain about 6 to about 20% lactic acid on weight/weight (w/w) basis, the lactic acid may be recovered in a concentrated form. The recovery of lactic acid in a concentrated form from a fermentation broth may be achieved by a plurality of methods and/or a combination of methods known in the art.

During the fermentation methods described herein, at least one alkali material (e.g., NaOH, $CaCO_3$, $(NH_4)_2CO_3$, $NH_4HCO_3$ $NH_4OH$, KOH, or any combination thereof) may be utilized in order to maintain the near neutral pH of the growth medium. Addition of alkali materials to the fermentation broth often results in the accumulation of lactic acid in the form of inorganic salts. In some embodiments, ammonium hydroxide may be a preferred alkali material for maintaining the neutral pH of the fermentation broth. With the addition of ammonium hydroxide to the fermentation medium, ammonium lactate may accumulate in the fermentation broth. Because ammonium lactate has higher solubility in aqueous solution, it may have an increased concentration in the fermentation broth. One way to obtain lactic acid from the fermentation broth containing ammonium lactate may include micro and ultra-filtration of the fermentation broth followed by continuous ion exchange (CIX), simulated moving bed chromatography (SMB), electrodialysis bipolar membrane (EDBM), fixed bed ion exchange, or liquid-liquid extraction. The sample coming out of fixed bed ion exchange may, in some embodiments, then be subjected to bipolar electrodialysis to obtain lactic acid in the form of a concentrated free acid.

In some embodiments, the reactants (e.g., lactic acid and lactic acid ester) may be derived from biological resources (e.g., glucose, sucrose and glycerol) through one or more chemical processes using chemical catalysts without involving any fermentation process using biocatalysts. For example, lactic and lactic acid esters derived from the biological resources may be subsequently subjected to dehydration and esterification reactions to yield acrylic acid and acrylic acid ester.

In another example, glycerol may be used as a starting material to produce lactic acid and then acrylic acid using a chemical process without involving any fermentation process. Global biodiesel production by trans-esterification of fatty acid esters derived from vegetable oils has increased several fold in the past decade to partly substitute the use of fossil-derived diesel fuel. Glycerol, a byproduct from biodiesel industry, may be a suitable or, in some embodiments, a preferred starting material for the manufacture of acrylic acid and acrylic acid esters according to the processes described in the present invention.

For example, one approach to produce lactic acid from glycerol may use the thermochemical conversion process where at temperatures higher than about 550° C. glycerol converts to lactic acid through intermediary compounds like glyceraldehydes, 2-hydroxypropenal and pyruvaldehyde. However, the thermochemical conversion process can cause significant decomposition of pyruvaldehyde and lactic acid at this elevated temperature, thereby leading to a decrease in the selectivity for lactic acid production. In some instances, the use of a chemical catalyst that mediates the dehydrogenation reaction responsible for the production of lactic acid may allow for the reduction in temperature, thereby enhancing selectivity and mitigating decomposition. In some instances, a heterogeneous catalyst may be preferred as the heterogeneous catalyst may be recovered and reused multiple times, may not require any buffering, and may be easily modified to run on a continuous flow process mode instead of a batch process mode to increase throughput and turnover time. These advantages may translate to a significant reduction in operating costs and waste disposal.

The catalyst useful in the vapor phase dehydration reaction according to the present invention is a solid heterogeneous catalyst having two components namely a support and an active inorganic salt. Porous aluminosilicate material with certain level of surface acidity acts as a support in the solid heterogeneous catalyst according to the present invention. Natural and synthetic zeolites with crystalline aluminosilicate architecture are highly suitable to function as a support for the heterogeneous catalyst of the present invention.

As used herein, zeolites refer to the aluminosilicate member of the family of microporous solid known as "molecular sieves". Zeolites are crystals made up of three dimensional networks of atoms. These networks are largely open structures containing cavities and channels of various sizes. The zeolite network is primarily made from three elements namely oxygen, silicon and aluminum. These three elements are arranged in tetrahedral units of $SiO_4$ and $AlO_4$ and these units are linked together to form the network of the crystal. Zeolites have a general molecular formula $M_{x/n}[(ALO_2)_x(SIO_2)_y]zH_2O$ where n is charge of the metal cation (M), M is usually $Na^+$, $K^+$, or $Ca^{2+}$, and z is the number of moles of water of hydration which is highly variable. An example of a zeolite may be natrolite with the formula $Na_2Al_2Si_3O_{10} \cdot 2H_2O$. As used herein, the term "modified zeolites" refer to zeolites having been modified by (1) impregnation with inorganic salts and/or oxides and/or (2) ion exchange.

Besides, silica, aluminum and oxygen, zeolite contain certain non-framework components. If zeolite is not dehydrated, it will contain a certain amount of water within the pores of the framework. Further, zeolite contains positively charged cations as non-framework component. These non-framework cations are required to maintain electrochemical neutrality of the zeolites. Each oxygen ion carries a formal charge of two. In a zeolite with no aluminum atoms, the ratio of silicon atoms to oxygen atoms would be 1 to 2. Each silicon atoms with its formal charge of positive four would balance two oxygen atoms with their individual formal charge of negative two. As a result, a zeolite having only silica would be electrochemically neutral. Aluminum atoms in zeolite carry a formal charge of positive three and a single aluminum atom cannot balance the charge from two oxygen atoms. As a result for every aluminum atom in a zeolite, there is one net negative charge. In order to correct this deficit of positive charge, zeolites having aluminum in its framework contains equal number of positive charges as non-framework cations. In naturally occurring zeolites, the non-framework cations can be represented by a proton. On the other hand, in the synthetic zeolites, the non-framework cation may be provided by $Na^+$, $K^+$, $Mg^{2+}$, $Ca^{2+}$, $NH4^+$ or protons $H^+$.

A number of synthetic zeolites have been prepared during the last 50 years with varying ratio of silica to alumina. For example Zeolite A was synthesized in 1948 by the scientists at Union Carbide. Next synthetic zeolite, Zeolite X was also synthesized by scientist at Union Carbide with silica to alumina ratio of 2. The other synthetic zeolite, Zeolite Y has a silica to alumina ratio between roughly four and seven. ZK-4 zeolite was synthesized by the scientist at Mobil using tetramethylammonium as organic cation. Zeolite Beta was also synthesized by scientist at Mobil using tetraethylammonium as a non-framework cation. Zeolite Beta could be synthesized with very high silica to alumina ratio from 5 to 150. High silica content increases the thermal stability of the zeolite. The ZSM-5 zeolite was synthesized by the scientist at Mobil using tetrapropylammonium as a non-framework cation. ZSM-5 has channels in two directions. In one direction, the channels are straight and in the other direction, the channels are undulated.

The suitability of a zeolite as a catalyst in a particular reaction is dependent on two factors namely the (1) topology of the zeolite and (2) composition of the zeolite. The topology of zeolites resulting from their porous architecture discriminates between the reactants. For example, if the pore diameter of a particular zeolite is about 5 angstroms, that particular zeolite is not suitable for catalytic conversion of reactant molecules with the diameter larger than 5 angstrom as it would not have access to the channels within the zeolite. This ability of zeolite to discriminate reactant molecules based on their size is referred as shape selectivity. Based on the dimension of their channels, the zeolites are divided into three categories namely small, medium and large pore zeolites. This information about size constraint index is useful to determine if a particular zeolite can function as a support for a catalyst.

Once a zeolite is qualified as a catalyst support based on its size selectivity, the next step is to determine if the chemical composition of the selected zeolite by itself is enough to carry out the required catalytic function on the reactant molecule. For example, in the instant invention, the selected catalyst is expected to catalyze the dehydration of the lactic acid molecule without catalyzing the decarbonylation, decarboxylation, condensation and reduction reactions of lactic acid. The desired catalytic function may be provided (1) by a zeolite itself or (2) by a zeolite in combination with yet another chemical compound. In the second instant, where there is a need for an additional chemical compound besides the zeolite to catalyze the desired chemical reaction, the zeolite is considered to provide a physical support for the additional chemical compound. Under the situation where an additional chemical compound is required besides the aluminosilicate framework of zeolite in catalyzing the desired chemical reaction, the chemical reaction may be catalyzed solely by the additional chemical compound and the zeolite provides only a physical support to the additional chemical compound. It is also possible that the zeolite and the additional chemical compound act together and catalyze the desired chemical reaction while suppressing unwanted chemical reaction. It is also possible that the additional chemical compound could establish a chemical interaction with the zeolite and thereby becoming a non-framework component of the zeolite. Such an interaction between zeolite framework and the additional chemical compound can be determined by using appropriate physical techniques such as x-ray diffraction and nuclear magnetic resonance spectroscopy.

As used in the present invention, the term "support" refers to zeolite with its porous aliminosilicate framework irrespective of the fact whether it has established any chemical interaction with the additional chemical compound or the interaction between the additional chemical compound and the aluminosilicate framework of zeolite is only physical.

As used in the present invention, the process of adding additional chemical compound to the zeolite is referred as "impregnation" process. The impregnation of the additional chemical compound onto zeolite material can be carried out in several different ways with the goal of impregnating appropriate amount of second chemical compound onto zeolite in a cost-effective way. In one aspect of the present invention, when the impregnation process is carried out in small scale, desired amount of additional chemical compound in aqueous solution is added to the fully dehydrated zeolite and the additional chemical compound enter into the channels of zeolite through capillary action. This process of impregnation is referred as "incipient impregnation". In another aspect of the present invention, the dehydrated zeolite is suspended in an aqueous solution of second chemical compound and stirred for a specified time so that the second chemical compound enters into the channels of zeolite. The resulting zeolite sample is allowed to stand for 2 hours at room temperature and dried ate 120° C. for 10 hours in air. Finally the dried sample is calcined at 300° C. for 3 hours. This process of impregnating second chemical compound into the zeolite is referred as "wet impregnation" process. In yet another aspect of the present invention, the impregnation of zeolite with a second chemical compound can be achieved in a large scale using rotating drums and spray heads. Large volume of dehydrated zeolite material is taken in rotating drums fitted with spray heads. While the drums are in a rotating mode, an aqueous solution of second chemical compound is sprayed onto the zeolite material to achieve required level of impregnation.

In general, an inorganic salt is used as second chemical compound in the impregnation process and therefore this impregnation process is also referred as "salt impregnation". In one aspect of the instant invention, the salt impregnation process is carried out using an inorganic salt selected from a group consisting of a phosphate, a, sulfate, a nitrate, a carbonate, a halide, a molybdate, a tungstate, a stanate, an antimonite, and any combination thereof. In a preferred embodiment of the present invention, the inorganic salt suitable for impregnation process is selected from a group consisting of a monosodium phosphate, disodium phosphate, a trisodium phosphate, a potassium phosphate, a sodium aluminum phosphate, and any combination thereof.

If a selected zeolite in its fresh form is not capable of catalyzing a particular chemical reaction, the selected zeolite may be subjected to certain chemical modification so that it could catalyze desired chemical reaction. Similarly, if the selected zeolite in its fresh form is catalyzing one or more unwanted chemical reactions leading to the production of undesirable side products, the selected zeolite may be subjected to certain chemical modifications to prevent the formation of undesirable side products. The chemical modification for the purpose of altering catalytic properties of zeolite is carried out with the fresh zeolite before subjecting it to salt impregnation process.

In one aspect of the present invention, the chemical modification of zeolite is done through dealumination reaction leading to removal of aluminum atom from aluminosilicate crystalline framework and a change in the silica to aluminum ratio, or replacing aluminum or silica atoms of framework with P, Ga, Fe, B, or other metal atoms.

In another aspect of the present invention, the chemical modification to zeolite is carried out by means of replacing the existing non-framework cation with a new cation and this chemical modification is referred as ion-exchange reaction. The successful ion exchange reaction can be monitored either using NMR spectroscopy of through elemental analysis involving inductively coupled plasma techniques. The ion-exchange reaction besides modifying the elemental composition also brings about a change in the surface acidity of zeolite.

Depending upon the chemical reaction catalyzed by zeolite, surface acidity contributes significantly to the catalytic properties of zeolites. Two different surface acidities, namely Brθnsted acidity and Lewis acidity are recognized on the surface of zeolites. Under Brθnsted theory, an acid is a proton donor while under Lewis theory, the acid is an electron acceptor. Therefore, Brθnsted acid is not a Lewis acid. However, a proton itself is an acid, as it has a vacant orbital that bonds to the base. Similarly, a Lewis base is also a Brθnsted base, since it is always capable of donating its unshared electron pair to a proton.

Bronstad acidity and Lewis acidity on the surface of a zeolite can be altered through specific chemical modifications to zeolite. For example, by means of replacing non-framework cations in the zeolite with a proton, the Brθnsted acidity can be introduced into a zeolite. Similarly, by means of replacing non-framework cations on the surface of zeolite with ammonium and calcining the ammonium exchanged zeolite at the elevated temperature, the ammonium cation can be decomposes to ammonia leaving behind a proton on the surface of zeolite in place of a non-framework cation. Similarly an ion-exchange reaction with a polyvalent cation can generate protons via partial hydrolysis of water molecule. On the other hand, mild streaming of a zeolite usually cause dehydroxylation and reduces the total number of Brθnsted sites while creating Lewis acid sites.

A number of physical characterization methods such as microcalorimetry, temperature programmed desorption (TPD), magic angle spinning nuclear magnetic resonance (MAS-NMR and infrared (IR) spectroscopy can be used to determine the acidity of the zeolite molecules before and after specific modifications such as ion-exchange reaction and salt impregnation process. With TPD technique the acid strength of zeolite material is measured in an indirect way using a probe molecule.

It is believed that zeolites contain channels (also known as voids or pores) that are occupied by the cations and water molecules. Without being limited by theory, it is believed that dehydration reactions conducted in the presence of zeolites may take place preferentially within the channels of the zeolites. Accordingly, it is believed that the dimensions of the channels affect, inter alia, the diffusion rates of chemicals there through, and consequently the selectivity and conversion efficiency of the dehydration reactions. In some embodiments, the diameter of the channels in zeolite catalysts suitable for use in conjunction with dehydration reactions disclosed herein may range from about 1 to about 20 angstroms, or more preferably about five to about 10 angstroms, including any subset there between.

Zeolites suitable for use as dehydration catalysts described herein may be derived from naturally-occurring materials and/or may be chemically synthesized. Further, zeolites suitable for use as dehydration catalysts described herein may have, in some embodiments, crystalline structures commensurate with L-type zeolites, Y-type zeolites, X-type zeolites, and any combination thereof. Different types of zeolites such as A, X, Y, and L differ from each other in terms of their composition, pore volume, and/or channel structure. A-type and X-type zeolites have a molar ratio of Si to Al of about 1 and a tetrahedral aluminosilicate framework. Y-type zeolites have a molar ratio of Si to Al of about 1.5 to about 3.0 and a framework topology similar to that of X-type zeolites. L-type zeolites have a molar ratio of Si to Al of about 3.0 and have one-dimensional pores of about 0.71 nm aperture leading to cavities of about 0.48 nm×1.24 nm×1.07 nm. ZSM-5 molecular sieve zeolites have Si/Al ratio from 10 to 100 or higher and a pore size of 0.6 nm.

In some embodiments, modified zeolites may be produced by performing an ion exchange with a zeolite. In some embodiments, modified zeolites suitable for use as dehydroxylation catalysts described herein may have ions associated therewith that may include, but are not limited to, H+, Li+, Na+, K+, Cs+, Mg2+, Ca2+, La2+, La3+, Ce2+, Ce3+, Ce4+, Sm2+, Sm3+, Eu2+, Eu3+, and the like, and any combination thereof. As used herein, "[ions associated]-[crystalline structure]-type zeolite" is used to abbreviate specific zeolites and/or modified zeolites. For example, an L-type zeolite having potassium ions associated therewith is abbreviated by K-L-type zeolite. In another example, a X-type zeolite having potassium and sodium ions incorporated therewith is abbreviated Na/K-X-type zeolite. In some embodiments, L-type zeolites may be modified by techniques like calcination, ion exchange, incipient wetness impregnation, hydro-treatment with steam, any hybrid thereof, and any combination thereof.

In some embodiments, modified zeolites suitable for use as dehydration catalysts described herein may have more than one cation associated therewith. In certain embodiments, modified zeolites suitable for use as dehydration catalysts described herein may comprise a first cation and a second cation, where the mole ratio of the first cation to the second cation may range from a lower limit of about 1:1000, 1:500, 1:100, 1:50, 1:10, 1:5, 1:3, 1:2, or 1:1 to an upper limit of about 1000:1, 500:1, 100:1, 50:1, 10:1, 5:1, 3:1, 2:1, or 1:1, and wherein the mole ratio may range from any lower limit to any upper limit and encompass any subset there between. By way of non-limiting examples, modified zeolites suitable for use as dehydration catalysts described herein may, in some embodiments, be H/Na-L-type zeolites, Li/Na-X-type zeolites, Na/K-Y-type zeolites, and any combination thereof. By way of another non-limiting example, modified zeolites suitable for use as dehydration catalysts described herein may, in some embodiments, be Na/K-L-type zeolites, Na/K-Y-type zeolites, and/or Na/K-X-type zeolites, where the ratio of sodium ions to potassium ions is about 1:10 or greater.

Without being limited by theory, it is believed that in embodiments where at least some $H^+$ ions on the zeolite are exchanged, the catalyst acidity of the produced modified zeolite may be reduced. The magnitude of the reduction in acidity may be determined using a suitable test. For example, ASTM (American Society for Testing and Materials) D4824 may be used to determine the acidity of the modified zeolite. Briefly, this test uses ammonia chemisorption to determine the acidity of the modified zeolite where a volumetric system is used to obtain the amount of chemisorbed ammonia.

In some embodiments, modified zeolites may be zeolites impregnated with an inorganic salt and/or oxide thereof. Inorganic salts suitable for use in producing modified zeolites describe herein may, in some embodiments, include, but are not limited to, phosphates, sulfates, molybdates, tungstates, stanates, antimonates, and the like, and any combination thereof with a cation of calcium, sodium, magnesium, aluminum, potassium, and the like, and any combination thereof. By way of nonlimiting example, in some embodiments, modified zeolites may be produced with sodium phosphate compounds (e.g., monosodium phosphate ($NaH_2PO_4$), disodium phosphate ($Na_2HPO_4$), and trisodium phosphate ($Na_3PO_4$)), potassium phosphate compounds, sodium aluminum phosphate compounds (e.g., Na8Al2(OH)2(PO4)4), and any combination thereof.

In some embodiments, modified zeolites suitable for use as dehydration catalysts described herein may be impregnated with an inorganic salt and/or oxide thereof at a concentration ranging from a lower limit of about 0.1 mmol, 0.2 mmol, or 0.4 mmol per gram of modified zeolite to an upper limit of about 1.0 mmol, 0.8 mmol, or 0.6 mmol per gram of modified zeolite, and wherein the concentration may range from any lower limit to any upper limit and encompass any subset there between. By way of non-limiting example, impregnated ZSM-5 type zeolites suitable for use in conjunction with dehydration reactions described herein may be Na/KZSM-5 type zeolite impregnated with a sodium phosphate compound, where the ratio of sodium ions to potassium ions is about 1:10 or greater. To begin with ZSM-5 type zeolite is synthesized using tetrapropylammonium cation as a templating agent which upon heating yield HZSM-5 type zeolite. Upon ion-exchange with a sodium salt NAZSM-5 zeolite is obtained. When impregnated with potassium phosphate Na/KZSM-5 form of zeolite is obtained.

One of ordinary skill in the art should recognize additional steps for the preparation of modified zeolites by ion exchange and/or impregnation. For example, drying and/or calcining may be needed to, inter alia, to remove water from the pores and/or to convert salts to oxides thereof. Further, proper storage may be needed to, inter alia, to prevent the modified zeolites from being at least partially deactivated during storage. As used herein, the term "calcining" refers to a process by which the zeolite catalyst is subjected to a thermal treatment process in the presence of air for the removal of a volatile fraction.

Solid dehydration catalysts suitable for use as dehydration catalysts described herein may, in some embodiments, have a high surface area. In some embodiments, solid dehydration catalysts suitable for use as dehydration catalysts described herein may have a surface area of about 100 m2/g or greater. In some embodiments, solid dehydration catalysts suitable for use as dehydration catalysts described herein may have a surface area ranging from a lower limit of about 100 m2/g, 125 m2/g, 150 m2/g, or 200 m2/g to an upper limit of about 500 m2/g, 400 m2/g, 300 m2/g, or 250 m2/g, and wherein the surface area may range from any lower limit to any upper limit and encompass any subset there between.

In some embodiments, dehydration catalysts described herein may be present in dehydration reactions described herein in a molar ratio of catalyst to reactant/intermediate of about 1:1000 or greater. In some embodiments, dehydration catalysts described herein may be present in dehydration reactions described herein in a molar ratio of catalyst to reactant/intermediate ranging from a lower limit of about 1:1000, 1:500, or 1:250 to an upper limit of about 1:1, 1:10, or 1:100, and wherein the molar ratio may range from any lower limit to any upper limit and encompass any subset there between.

In some embodiments, dehydration reaction may utilize more than one type of dehydration catalyst described herein. In some embodiments, the weight ratio of the two dehydration catalysts may be about 1:10 or greater. In some embodiments, the weight ratio of the two dehydration catalysts may range from a lower limit of about 1:10, 1:5, 1:3, or 1:1 to an upper limit of about 10:1, 5:1, 3:1, or 1:1, and wherein the weight ratio may range from any lower limit to any upper limit and encompass any subset there between. One skilled in the art with the benefit of this disclosure should understand the extension of such ratios to three or more dehydration catalysts described herein.

In some embodiments, a dehydration reaction useful in reaction pathways of the present invention may be performed at a temperature ranging from a lower limit of about 100° C., 150° C., or 200° C. to an upper limit of about 500° C., 400° C., or 350° C., and wherein the temperature may range from any lower limit to any upper limit and encompass any subset there between.

Polymerization inhibitors may be utilized in conjunction with dehydration reactions described herein to prevent the polymerization of α, β-unsaturated carboxylic acids or the esters thereof produced along the reaction pathway. In some embodiments, polymerization inhibitors may be introduced to a reaction pathway of the present invention, e.g., in the starting composition, during a dehydration reaction, during an esterification reaction, and any combination thereof. Examples of polymerization inhibitors may include, but are not limited to, 4-methoxy phenol, 2,6-di-tert-butyl-4-methylphenol, sterically hindered phenols, and the like.

In some instances, the dehydration reaction of the present invention can be conducted in the absence of any zeolites support described herein and only in the presence of additional chemical compound supported on materials such as glass, ceramic, porcelain, or metallic material present within the reaction vessel and such a dehydration reaction in the absence of a zeolite support is expected to have lower conversion of lactic acid and reduced specificity for α,β-unsaturated carboxylic acid.

In some embodiments, a dehydration reaction of the present invention may have a conversion efficiency of about 40% or greater, in some embodiments about 50% or greater, in some embodiments about 55% or greater, in some embodiments about 60% or greater, in some embodiments about 65% or greater, in some embodiments about 70% or greater, in some embodiments about 75% or greater, in some embodiments about 80% or greater, in some embodiments about 85% or greater, in some embodiments about 90% or greater, in some embodiments about 95% or greater, in some embodiments about 98% or greater, or in some embodiments about 99% greater.

In some embodiments, the selectivity of the dehydration reaction of the present invention may result in production of α,β-unsaturated carboxylic acids and/or esters thereof in an amount that is 40 wt % or greater of a product, in some embodiments 50 wt % or greater of a product, in some embodiments 55 wt % or greater of a product, in some embodiments 60 wt % or greater of a product, in some embodiments 65 wt % or greater of a product, in some embodiments 70 wt % or greater of a product, in some embodiments 75 wt % or greater of a product, in some embodiments 80 wt % or greater of a product, in some embodiments 85 wt % or greater of a product, in some embodiments 90 wt % or greater of a product, in some embodiments 95 wt % or greater of a product, in some embodiments 98 wt % or greater of a product, and in some embodiments 99 wt % or greater of a product.

It should be understood that the conversion efficiency and/or selectivity of the dehydration reaction is dependent on, inter alia, controlling the temperature for calcining the catalyst where applicable, the composition of the dehydration catalyst, the concentration of reactants and/or intermediates, and/or the duration of the contact between the reactants and/or intermediates and the dehydroxylation and/or esterification catalysts.

In some instances, it has been observed that the reactor metallurgy may adversely affect the acrylic acid selectivity in lactic acid dehydration reaction. Without being limited by theory, it is believed that the lactic acid feed may cause the corrosion of reactor walls leading to the leaching of metal components from the reactor wall. For example, when a stainless steel reactor is used in the dehydration reaction, metal components such as nickel, chromium and iron may leach out into the product stream and/or accumulate onto the dehydration catalyst, which can, for example, be detected using inductively coupled plasma (ICP) analysis. The leached metals may act as a catalyst capable of forming byproducts. For example, nickel released from the walls of a stainless steel reactor may act as a hydrogenation catalyst leading to the formation of propionic acid from acrylic acid. Similarly, iron released from the walls of the stainless steel reactor may function as a decarboxylation catalyst leading to the formation of acetaldehyde. Additionally, some of the components leached out of the reactor walls may lead to the polymerization of lactic acid and acrylic acid. Accordingly, in some embodiments, reactor materials may be chosen to be resistant to corrosion either by feed or the products formed through catalytic dehydration reaction. Examples of suitable reactor materials that may mitigate unwanted catalysis may include, but are not limited to, titanium, silanized stainless steel, quartz, and the like. Such a reactor with reduced level of corrosion may provide for higher selectivity for acrylic acid and reducing byproduct formation.

Any suitable systems may be used in conjunction with carrying out the dehydration reaction of the present invention. In some embodiments, systems suitable for use in conjunction with carrying out the reaction pathways of the present invention may comprise reactors and optionally comprise at least one of preheaters (e.g., to preheat starting compositions, solvents, reactants, and the like), pumps, heat exchangers, condensers, material handling equipment, and the like, and any combination thereof. Examples of suitable reactors may include, but are not limited to, batch reactors, plug-flow reactors, continuously-stirred tank reactors, packed-bed reactors, slurry reactors, fixed-bed reactors, fluidized-bed reactors, and the like. Reactors may, in some embodiments, be single-staged or multi-staged. Further, reaction pathways of the present invention may be performed, in some embodiments, batch-wise, semi-continuously, continuously, or any hybrid thereof.

As stated above, the dehydration reaction may be conducted in the liquid and/or vapor phase. Accordingly, carrier gases (e.g., argon, nitrogen, carbon dioxide, and the like) may be utilized in conjunction with the dehydration reaction and/or systems described herein. In some embodiments, the dehydration reaction may be conducted in the liquid and/or the vapor phase, which, in some embodiments, may be substantially a single inert gas (e.g., the carrier gas being greater than about 90% of a single carrier gas) or a mixture of multiple inert gases. In some embodiments, the dehydration reaction may be conducted in the liquid and/or the vapor phase, which, in some embodiments, may be substantially carbon dioxide (e.g., the carrier gas being greater than about 90% carbon dioxide).

In some embodiments, dehydration reaction of the present invention may proceed at a weight hour space velocity ("WHSV") of about 0.2 $hr^{-1}$ to about 1.5 $hr^{-1}$, or more preferably about 0.5 $hr^{-1}$ to about 1.2 $hr^{-1}$.

In some embodiments, the product of dehydration reaction of the present invention may comprise α,β-unsaturated carboxylic acids and/or esters thereof and other components (e.g., solvents, polymerization inhibitors, byproducts, unreacted reactants, dehydroxylation catalysts, and/or esterification catalysts). Accordingly, the product of a dehydration reaction of the present invention may be separated and/or purified into components of the product (including mixtures of components). In some embodiments, the solvent may be separated from the product of a dehydration reaction of the present invention and recycled for reuse. Recycling solvents may advantageously produce less waste and reduce the cost of producing α,β-unsaturated carboxylic acids and/or esters thereof.

Suitable techniques for separation and/or purification may include, but are not limited to, distillation, extraction, reactive extraction, adsorption, absorption, stripping, crystallization, evaporation, sublimation, diffusion separation, adsorptive bubble separation, membrane separation, fluid-particle separation, and the like, and any combination thereof.

One skilled in the art with the benefit of this disclosure should further recognize that at least some of the various dehydration catalysts described herein may be regenerated either in situ or ex situ. For example, in some embodiments, zeolites and/or modified zeolites may be regenerated at elevated temperatures in the presence of oxygen (e.g., air or oxygen diluted in an inert gas).

To facilitate a better understanding of the present invention, the following examples of preferred or representative embodiments are given. In no way should the following examples be read to limit, or to define, the scope of the invention.

EXPERIMENTAL SECTION

Table 1 provides formulas for several calculations used throughout the examples section.

Figure 2:
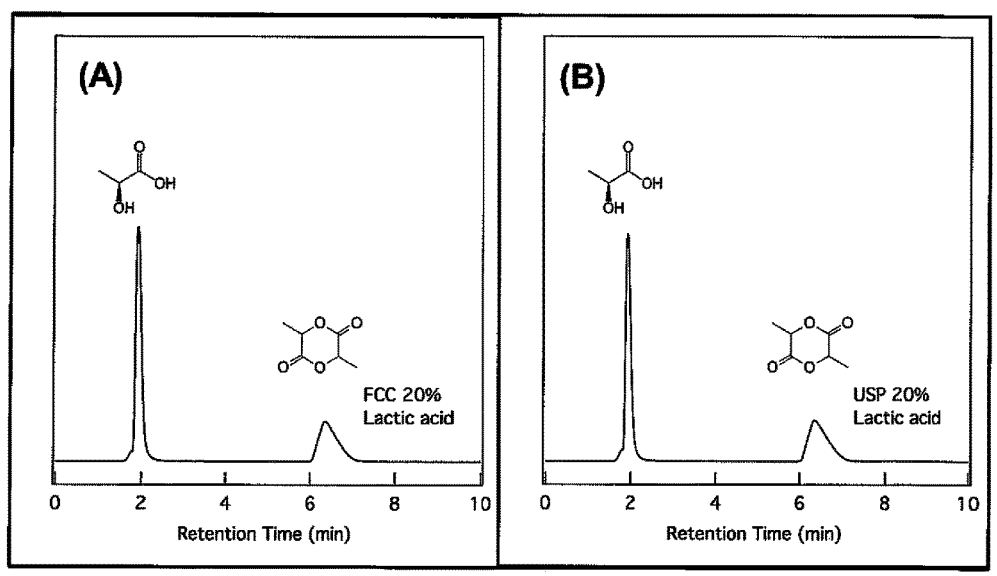
FIG. 2 Separation of lactic acid and lactide from two different commercial supplies of biomass-derived lactic acid preparations from Archer Daniels Midland Company namely ADM LA-FCC (A) and ADM LA-HS USP 20 (B) on a Shimadzu 10A HPLC with SPD-10A UV-Vis detector (210 nm). A Phenomenex Synergi 4m Fusion-RP 80 A×4.6 mm column was used. The mobile phase was a 10 mM phosphoric (sodium) aqueous solution. One ml of sample (20% lactic acid aqueous solution) was injected onto the column.

Quantification of the reactants: Two different samples of bio-based lactic acid samples (ADM LA-FCC and ADM LA-HS USP) received from Archer Daniels Midland Company (Chicago, Ill., USA) were analyzed using high performance liquid chromatography (HPLC) and nuclear magnetic resonance (NMR) spectroscopy to determine the relative percentage of lactic acid and its dimeric form (lactide). Shimadzu 10A HPLC was operated with SPD-10A UV-Vis detector (210 nm) and a Phenimenex Synergi 4m Fusion-RP 80 Å×4.6 mm column. The mobile phase was a 10 mM phosphoric (sodium) aqueous solution. One mL of sample (20% lactic acid aqueous solution) was injected into the column. Two peaks with retention times of 1.92 and 6.92 minutes were observed in the HPLC profile (FIG. 2). The first peak at 1.92 minute was attributable to lactic acid fraction and the second peak at 6.92 minute was attributable to lactide fraction. Based on this HPLC analysis, it was determined that the ADM FCC sample contained 63.0% lactic acid, 35.6% lactide and 1.5% unknown materials while the ADM HS-USP samples contained 63.4% lactic acid, 34.8% lactide and 1.8% unknown materials.

Feed preparation: The commercially available bio-based lactic acid is at about 88% in its concentration. However, due to the equilibrium limitation between the lactic acid monomer and its oligomers, only about 72% of lactic acid is available in the monomeric form. The remaining carbon is mostly in lactide form and a minor portion is in the form of higher oligomers. The lactide and longer chain oligomers are formed during the final evaporation step of bio-based lactic acid manufacturing process. The catalytic dehydration reactions according to the present invention were performed with 5-60% lactic acid feed, which required the dilution of commercial 88% lactic acid product. In order to determine a complete and accurate carbon balance, the diluted feed was subjected to heat treatment to convert all of lactide and other oligomers to monomeric lactic acid.

Figure 3:
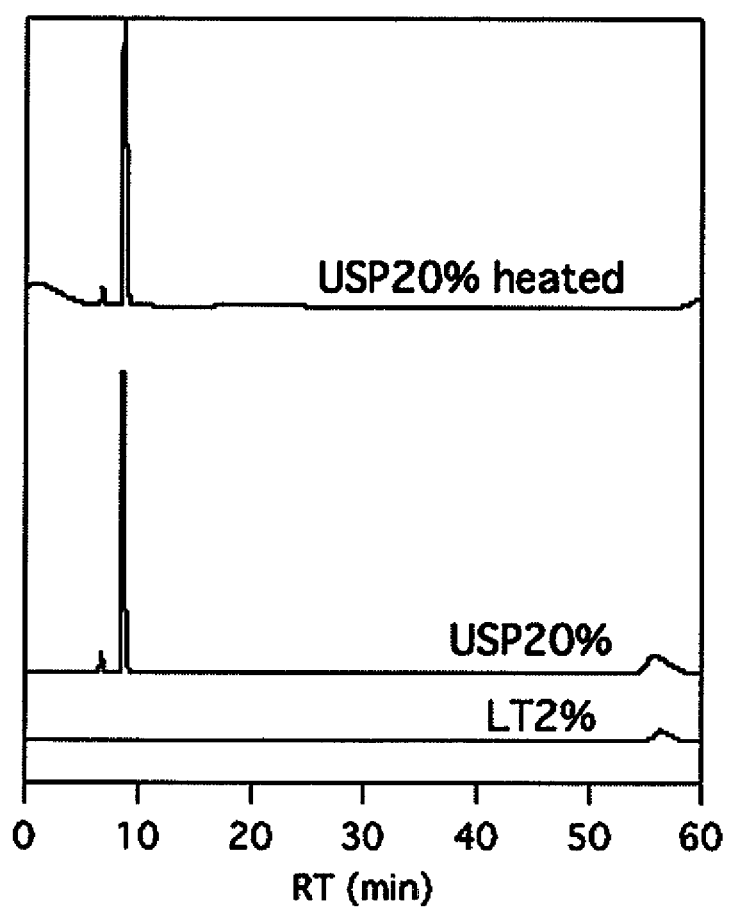
FIG. 3 Heat treatment of lactic acid preparation to convert lactide into lactic acid. Shown in this figure are the chromatographs of commercial lactic acid preparation (ADM LA-HS USP 20) before and after heat treatment at 80° C. for 15 hours. Upon heat treatment, the peak at 57 minutes corresponding to lactide fraction disappeared in the chromatograph. Also shown in this figure is a chromatograph of 2% lactide solution (Sigma Aldrich Chemicals) used as a standard.

The dilute lactic acid feed solution was charged to a round-bottom flask and stirred with a magnetic stirring bar during the heat treatment. Once the temperature reached 80° C., the solution was held at that temperature for 15 hours. After 15 hours of heat treatment, the lactide concentration became almost negligible. This heat-treated lactic acid solution was used in the catalytic dehydration reactions to produce acrylic acid. For the purpose of preparing large volume of lactic acid feed, the heat treatment of the dilute feed solution can be performed in an incubator shaker. FIG. 3 shows the chromatograph of the commercial sample of the bio-based lactic acid containing lactide and the disappearance of the lactide peak upon heat treatment. Also shown in this figure is the chromatograph of lactide aqueous solution from Sigma Aldrich Chemicals (LT2%) The type of lactic acid enantiomer [D (−) lactic acid or L (+) lactic acid] or the enantiomeric purity doesn't affect the dehydration reaction selectivity to acrylic acid.

Figure 4:
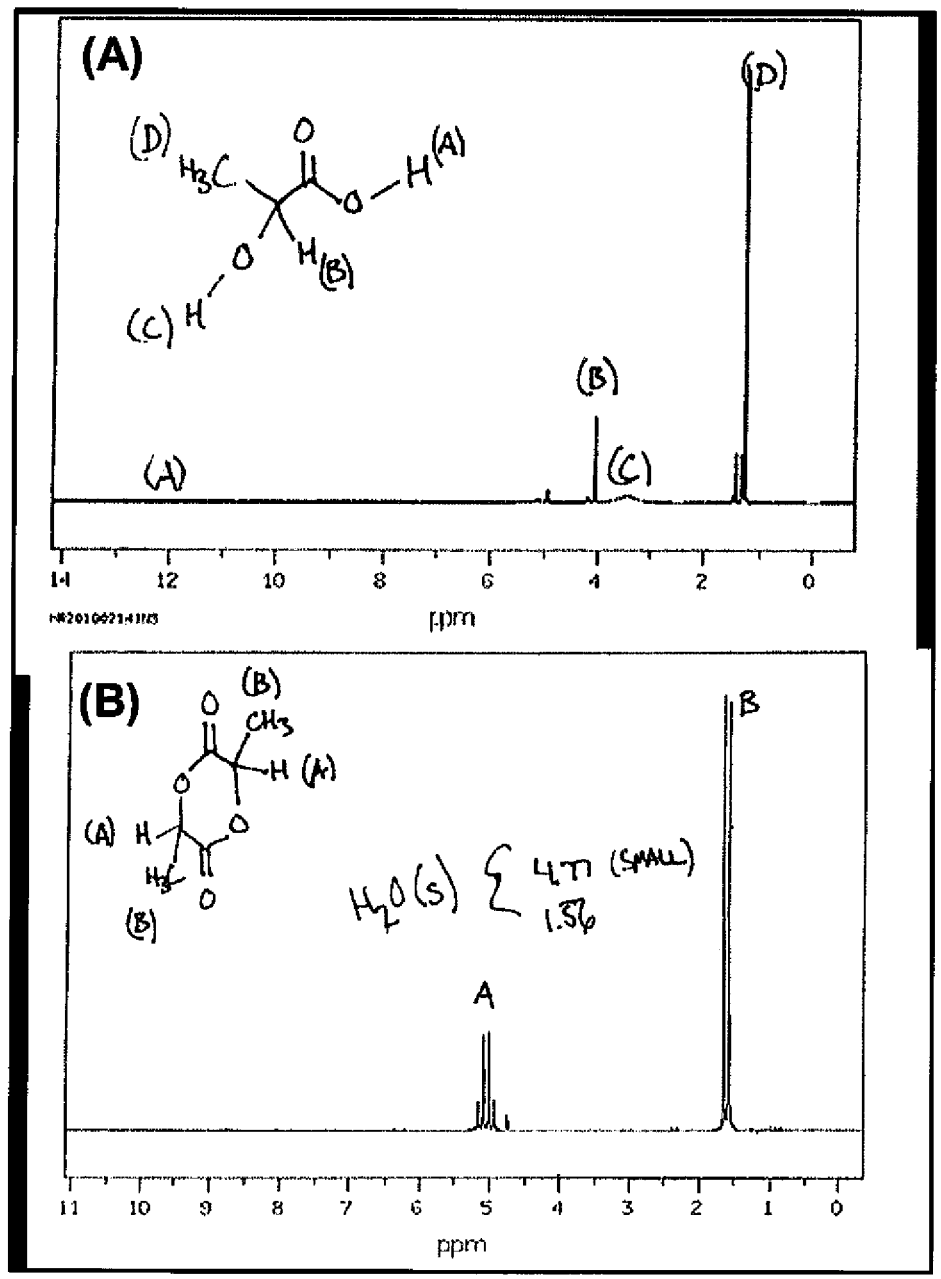
FIG. 4 Proton ($^1H$) NMR spectra for lactic acid in dimethylsulfoxide (DMSO) and (B) lactide in $CDCl_3$.

Proton ($^1H$) NMR spectra of bio-based lactic acid samples ADM LA-FCC and AMD LA-HS USP were acquired on a Bruker AV-360 spectrometer. Samples (16 scans) were run at 360 mhz for $^1H$ nuclei. FIGS. 4A and 4B are examples of $^1H$ spectra for lactic acid and lactide, respectively.

Figure 5:
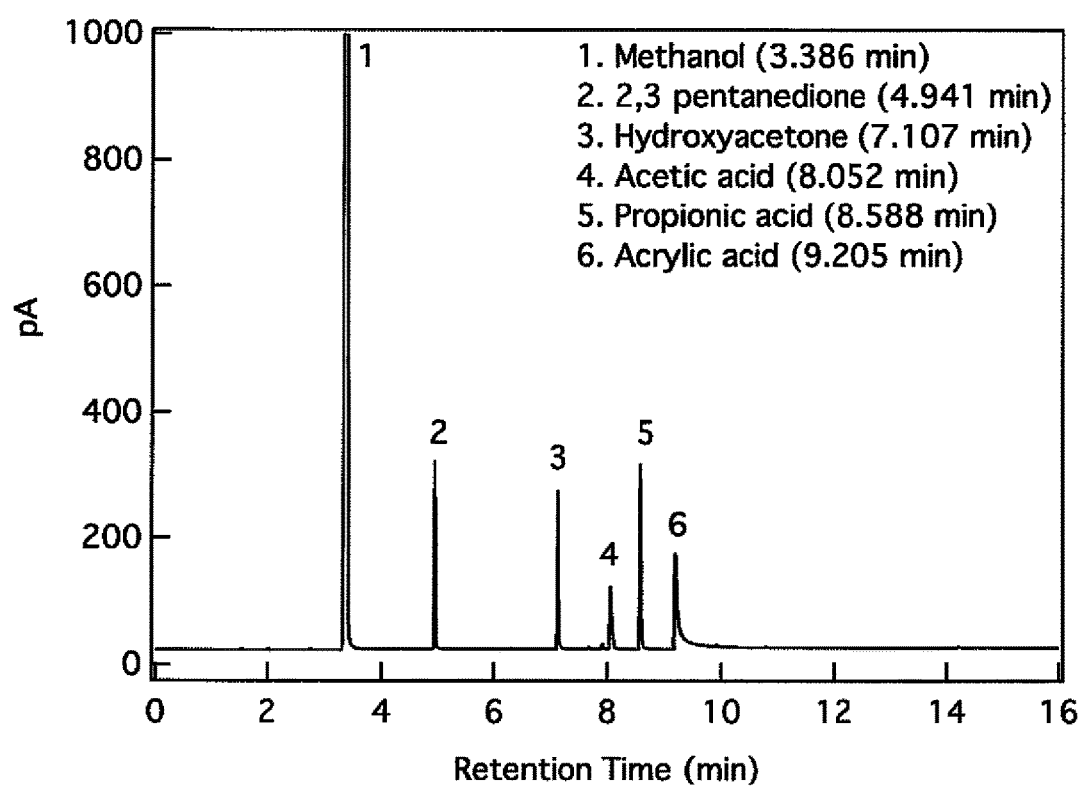
FIG. 5 GC chromatograph for synthetic mixture of six compounds including diluent methanol. Peaks are easily resolves in the FFAP column. The chromatograph was reproduced in IgorPro from Agilent Chemstation.

Quantification of products of lactic acid dehydration reaction: A gas chromatography apparatus (GC System—Agilent 7890A) with FFAP capillary column was used to quantify 2,3 pentanedione, hydroxyacetone, acetic acid, propionic acid and acrylic acid in the products of lactic acid hydration reaction. The GC apparatus was operated using the following parameters: Injection temperature: 250° C.; Detector Temperature: 300° C.; Air flow: 400 ml/min; $H_2$ flow: 44 ml/min; He flow: 30 ml/min; Oven temperature: 40° C. for 2 minutes, 20° C./minute to 220° C., and hold 5 minutes; Injection volume: 1 ml and Split ratio 25:1. Under this operating conditions, it was possible to separate and detect acrylic acid, hydroxyl acetone, propionic acid, 2,3-pentanedione and acetic acid (FIG. 5). The mole selectivity of acrylic acid and other products were calculated as follows: Selectivity=Areas of a product/Total area of the products. The areas are first corrected with response factors determined utilizing calibrating curves. The retention time for acetaldehyde, 2,3-Pentanedione, hydroxyl acetone, acetic acid, propionic acid and acrylic acid were determined to be 2.0 min, 3.4 min, 4.9 min, 8.0 min, 8.6 min, and 9.2 min respectively. The response factor for acetaldehyde, 2, 3-Pentanedione, hydroxyl acetone, acetic acid, propionic acid and acrylic acid were determined to be 1.23, 1.14, 1.54, 1.00, 1.62 and 1.34 respectively. When calculating total area of the products, two unknown peaks at 12.2 and 12.3 minutes were excluded as these peaks are related to lactic acid.

Catalyst Loading, Reactor Set-Up and Reaction Run: The volume of the catalyst was measured using a graduated cylinder and its weight was determined gravimetrically. An inert material such as glass wool, porcelain beads, alumina beads and titanium wool was used to support the catalyst bed. The same inert material was also used on top of the catalyst bed to serve as a pre-heating zone to vaporize the liquid feed. The support was inserted first and the catalyst is slowly poured on top of the support. The reactor was tapped gently to pack the catalyst bed. The catalyst bed was positioned in the center of the furnace. The inlet and outlet of the cooling water lines were connected to the condenser jacket located beneath the reactor outlet to recover all the condensates at 2° C. using chilled water recirculation. The liquid inlet was adjusted in such a way so that it could deliver the feed right into the pre-heating zone above the catalyst bed. A thermocouple was placed in the middle of the reactor to monitor the reaction temperature. The entire reactor is secured within the furnace and the connections are coupled at the 'T' joint where the liquid feed and the inert carrier gas were mixed prior to entering the reactor. The top and bottom opening of the furnace were covered with insulation to prevent any heat losses. The liquid feed and the inert carrier gas flows were started at desired values once the target reaction temperature is achieved. The condensates were collected and analyzed by offline HPLC and the non-condensable products were analyzed by using an online GC. The short run format of the dehydration reaction was run for 4 hours while the reaction products were collected for each hour. The analytical data were used to estimate the conversion of the reactant, products selectivity and carbon balance.

Figure 6:
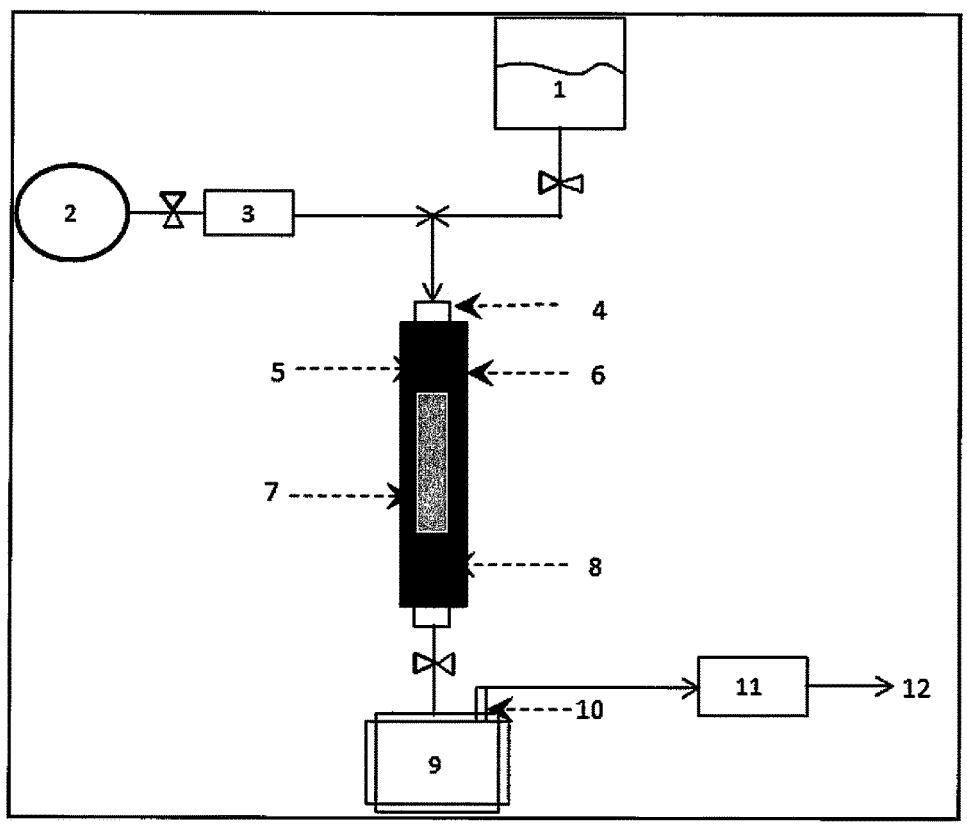
FIG. 6 Schematic of the catalytic dehydration reactor used in the present invention. Various parts of the reactor are numbered as provided here: 1—Liquid feed; 2—Inert carrier gas; 3—Mass flow controller; 4—Reactor; 5—Preheating zone with an inert support on top of the catalyst bed; 6—Furnace; 7—Catalyst bed; 8—Inert support for the catalyst bed; 9—Condenser and collection pot; 10—Vent for non-condensables; 11—In-line gas chromatography; and 12—Vent.

A simplified schematic of the reactor set up is shown in FIG. 6. The reactor can be of any material of construction such as stainless steel, quartz, titanium, or metal alloys.

When the reactor is made up of stainless steel, it is preferred to modify the inner surface of the stainless steel reactor with the silane coupling agent (SCA), (3-mercaptopropyl)trimethoxysilane as the non-functionalized stainless steel surface can interfere with the reaction and potentially lead to increase in the unwanted side products such as propionic acid. The quartz surface has been found to have certain reactivity to lactic acid and not being completely inert to the reaction. However, it is preferable to use the reactor made up of quartz.

Appropriate fittings and seals are used to complete the connection and prevent any leaks. The reactor can be operated in trickle feed mode, where the liquid feed droplets are trickled onto the catalyst bed or as a vapor feed mode, where the liquid feed is vaporized in the pre-heating zone prior to coming in contact with the catalyst bed.

Zeolite catalysts used in the present invention: The zeolite catalysts used in the present invention were obtained from several different vendors. The details about various zeolites used in this study are provided in Table 2. Elemental analysis of a few selected commercial zeolites is provided in Table 3.

Zeolite catalyst modification: The catalyst used in the present invention were subjected to either ion-exchange reaction or salt impregnation or both ion-exchange and salt impregnation before their use in the dehydration reaction involving lactic acid leading to the production of acrylic acid. The nomenclature for various zeolites used throughout this patent specification provides details about the modifications made to the zeolite. In brief, the first one or two letters indicate the non-framework element associated with the zeolite. For example, the name HZSM-5 indicates it is a ZSM-5 zeolite with a proton ($H^+$) as a non-framework element. The name NaZSM-5 indicates it is ZSM-5 zeolite with sodium ($Na^+$) as a non-framework cation. 3×Na-ZSM-5 is a zeolite subjected to ion exchange with a sodium salt three times. The parent zeolite used in the on-exchange reaction might be HZSM-5 (where $H^+$ is exchanged for $Na^+$) or a KZSM-5 where $K^+$ is exchanged for $Na^+$). 7.1 wt % Na2HPO4-3×Na-ZSM-5 is a zeolite subjected to ion-exchange reaction three times followed by impregnation with 1.1 wt % of $Na_2HPO_4$.

Characterization tools: A number of techniques were utilized in the present invention to evaluate the properties, fresh zeolites, ion-exchanged zeolites, salt impregnated zeolites and fresh and spent zeolites. These zeolite characterization techniques include Temperature Programmed Desorption (TPD), Nuclear Magnetic Resonance (NMR), X-Ray Diffraction (XRD), Thermogravimetric analysis (TGA), and Surface area & pore volume analysis (BET analysis) and Inductively Coupled Plasma (ICP) technique for the determination of elemental composition.

Temperature Programmed Desorption (TPD): NH3-TPD measurements were performed with Micromeritics Autochem 2920 for several zeolite samples to study their acidity profile. In a typical measurement, ~0.5 g of samples was used. Description of $NH_3$ was measured using a thermal conductivity detector (TCD). The pretreatment and analysis conditions are summarized as follows: (1) Pretreatment/dying: Temperature is ramped to 450° C. with the rate of 10° C./min and hold for 60 min under He gas flow (50 cc/min); (2) $NH_3$ adsorption: After cooling down to 50° C., $NH_3$ is introduced to the sample tube (20 cc/min) for 60 min; (3) Pre-desorption: Gas is switched to He and temperature is ramped to 150° C. at a rate of 10° C./min and held for 80 min to remove physiosorbed $NH_3$; and (4) TPD: Ramp up to 650° C. with the rate of 5° C./min and hold for 60 min.

This procedure is typical of those found in the published literature to characterize the activity of zeolites. The low temperature desorption peak is typically associated with Lewis acidity, while the high temperature peak is associated with Brθnsted acidity. The results can be somewhat obscured by the influence of re-adsorption and other packed bed dynamics. Therefore, the results are typically analyzed on a more qualitative sense, than quantitative.

Nuclear Magnetic Resonance (NMR): All solid state NMR experiments were carried out on a Bruker AV300. NMR technique is useful in monitoring the incorporation of one or other cation as non-framework cation in zeolite and also the phase transition of the alkali salt impregnated into zeolite materials.

X-Ray Diffraction (XRD): Below paragraph is a generic description of XRD from the internet and Wikipedia. X-ray powder diffraction (XRD) is a rapid analytical technique primarily used for phase identification of a crystalline material and can provide information on unit cell dimensions. The analyzed material is finely ground, homogenized, and average bulk composition is determined. is a tool used for identifying the atomic and molecular structure of a crystal, in which the crystalline atoms cause a beam of incident X-rays to diffract into many specific directions. By measuring the angles and intensities of these diffracted beams, a crystallographer can produce a three-dimensional picture of the density of electrons within the crystal. From this electron density, the mean positions of the atoms in the crystal can be determined, as well as their chemical bonds, their disorder and various other information. The technique of single-crystal X-ray crystallography has three basic steps. The first—and often most difficult—step is to obtain an adequate crystal of the material under study. The crystal should be sufficiently large (typically larger than 0.1 mm in all dimensions), pure in composition and regular in structure, with no significant internal imperfections such as cracks or twinning.

In the second step, the crystal is placed in an intense beam of X-rays, usually of a single wavelength (monochromatic X-rays), producing the regular pattern of reflections. As the crystal is gradually rotated, previous reflections disappear and new ones appear; the intensity of every spot is recorded at every orientation of the crystal. Multiple data sets may have to be collected, with each set covering slightly more than half a full rotation of the crystal and typically containing tens of thousands of reflections.

In the third step, these data are combined computationally with complementary chemical information to produce and refine a model of the arrangement of atoms within the crystal. The final, refined model of the atomic arrangement—now called a crystal structure—is usually stored in a public database.

Thermogravimetric Analysis (TGA): TGA analysis of fresh and spent catalyst was performed with TA Instruments TGA 2050. The TGA profile of the fresh sample indicates desorption of physiosorbed material from the surface of the fresh catalyst occurred at temperatures lower than 200° C. In the case of fresh catalysts there was no mass loss after 200° C. The TGA profile for spent catalyst showed a different profile with mass loss occurring at temperatures higher than 200° C. Assuming that the mass loss occurring in the spent catalyst is attributable to carbon loss, one can estimate the total carbon deposit on the surface of the spent catalyst and from that value one could back calculate the total carbon deposit with reference to the total carbon fed into the reactor.

Brunauer, Emmett and Teller (BET) method for surface area analysis: BET theory is based on the phenomenon of physical adsorption of gases on the external and internal surfaces of a porous material. Such a material which is surrounded by and in equilibrium with a certain gas which has a certain temperature T, and relative vapor pressure P/Po adsorbs physically certain amount of gas. The amount of adsorbed as is dependent on its relative vapor pressure and is proportional to the total external and internal surface of the material. For obtaining BET surface area, nitrogen adsorption-desorption measurement were performed using Micrometrics ASAP 2020 at 77K after degassing the samples at 350° C. for 4 hours using vacuum.

Inductively Coupled Plasma Optical Emission Spectrometry (ICP-OES) techniques: Samples derived from various processes according to the present invention can be tested using Inductively Coupled Plasma Optical Emission Spectrometry. The samples are diluted to less than 5% organics using 2% trace metal grade nitric acid. The ICP-OES produces a curve that ranges from 0.05 ppm to 10 ppm, thus the sample is diluted so that the target molecule concentration falls between these concentrations. If the sample contains any complex matrices or insoluble liquids, they are digested or ashed prior to being dissolved. The samples are then placed in an auto sampler connected to the ICP-OES, with a quality control in the first, middle, and last position. The ICP-OES will then analyzed the standards, generate a calibration curve, and analyze the samples. The software will then calculate the ppm for each substance detected, and from there the initial concentration of the substance can be determined based upon the dilution factor when the sample was prepared.

Example 1

Ion-exchange and Salt Impregnation Protocols for Modifying Zeolite Catalysts

Figure 7:
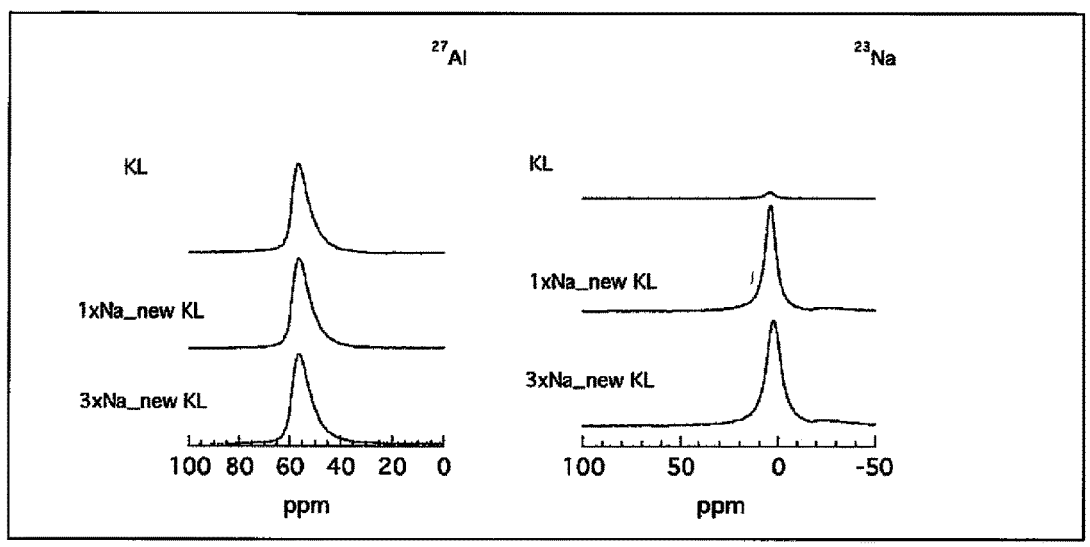
FIG. 7 $^{27}Al$ and $^{23}Na$ solid state NMR spectra for potassium form of zeolite L (KL), potassium form of zeolite L ion-exchanged one time with 200 ml of 1M sodium chloride solution (1×Na-KL) and potassium form of zeolite L ion-exchanged three times with 200 ml of 1M sodium chloride solution (3×Na-KL).

K form of zeolite L catalyst has potassium as the non-framework cation. Following the ion exchange protocol provided below, it is possible to replace the potassium ion with sodium ion as the non-framework cation. 15 grams of zeolite K-form was dissolved in 200 ml of 1M sodium chloride solution and stirred at room temperature for 6 hours. In a modified version of this ion-exchange protocol, it is possible to conduct this stirring step at 60° C. for an hour or for up to 6 hours. At the end of the stirring step, the zeolite L is filtered and the process is repeated three times. At the end of the third filtration step, the filtrate was calcined by slowly ramping the temperature to 450° C. over a 2 hour period and holding it at 450° C. for 2 hours. The calcined material was analyzed using NMR spectroscopy. $^{27}Al$ and $^{23}Na$ solid state NMR spectra for fresh zeolite L-K form and the 1× sodium exchanged (1×Na-Zeolite-L) and 3× sodium exchanged (3×Na-Zeolite-L) form were recorded. As the result shown in FIG. 7 indicates that $^{27}Al$ NMR signal remained the same in zeolite even after three ion-exchange reactions with NaCl solution. On the other hand, $^{23}Na$ NMR signal was not detectable in the fresh zeolite of K form. However, one time ion exchange or three time ion exchange of zeolite L-K form with sodium chloride solution showed the appearance of the $^{23}Na$ specific peak in the NMR spectrum (FIG. 7). The ion-exchange process described in this Example 1 can be appropriately modified for achieving exchange of non-framework cations in any other alumino silicate materials. The modified ion-exchange method has an additional intermediate heat treatment step to improve the ion-exchange efficiency. This was using for converting proton form of ZSM-5 materials from Zeolyst to sodium form and comparing it with the sodium ZSM5 from Tricat. The modified version of the ion exchange did result in improved acrylic acid selectivity but this was never applied to Tricat Na-ZSM5 because it already came in sodium form.

Figure 8:
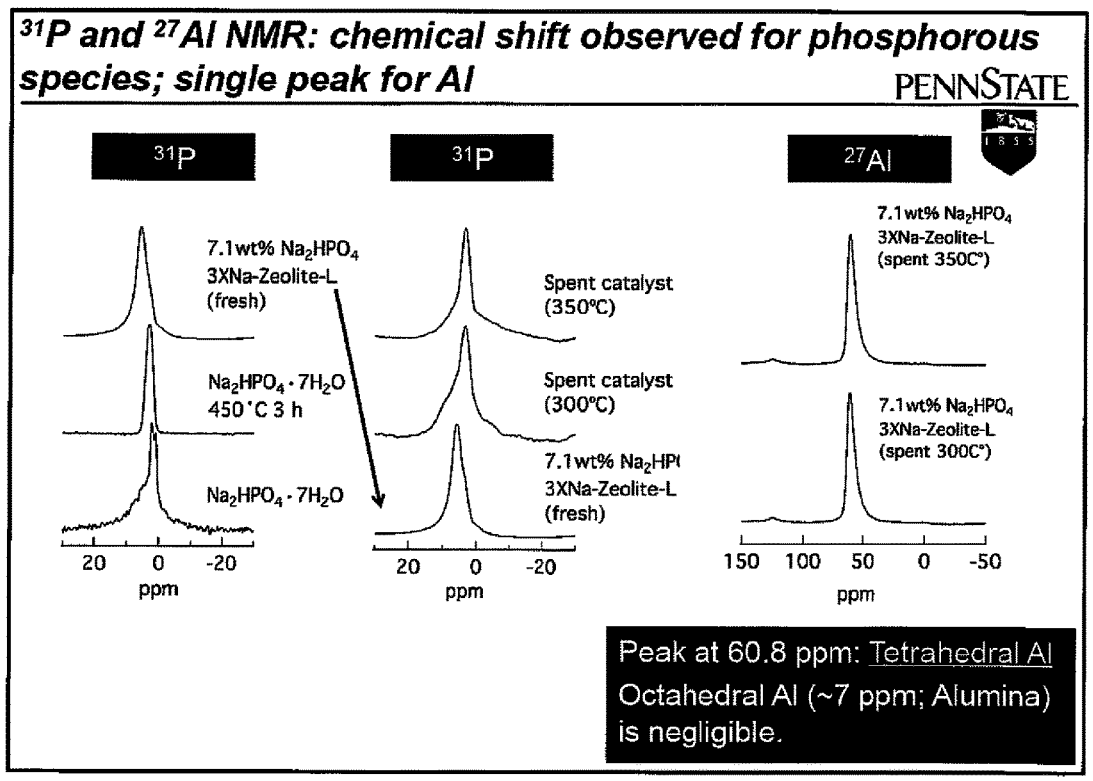
FIG. 8 $^{31}P$ and $^{27}Al$ NMR spectra of $Na_2HPO_4.7H_2O$ and fresh and spent 3×Na-zeolite doped with 7.1 wt % $Na_2HPO_4$.

3×Na-Zeolite-L was further modified by impregnation with 7.1 wt % $Na_2HPO_4 \cdot 7H_2O$ and calcined at 450° C. The resulting 7.1 wt % $Na_2HPO_4$-3×Na-Zeolite-L was used in the vapor phase dehydration reaction using lactic acid as a reactant at 300° C. and 350° C. and the $^{31}P$ and $^{27}Al$ NMR spectra of fresh and spent catalyst from lactic acid dehydration reaction were recorded as shown in FIG. 8.

Example 2

Ion-exchange Reaction with Boron

Figure 9:
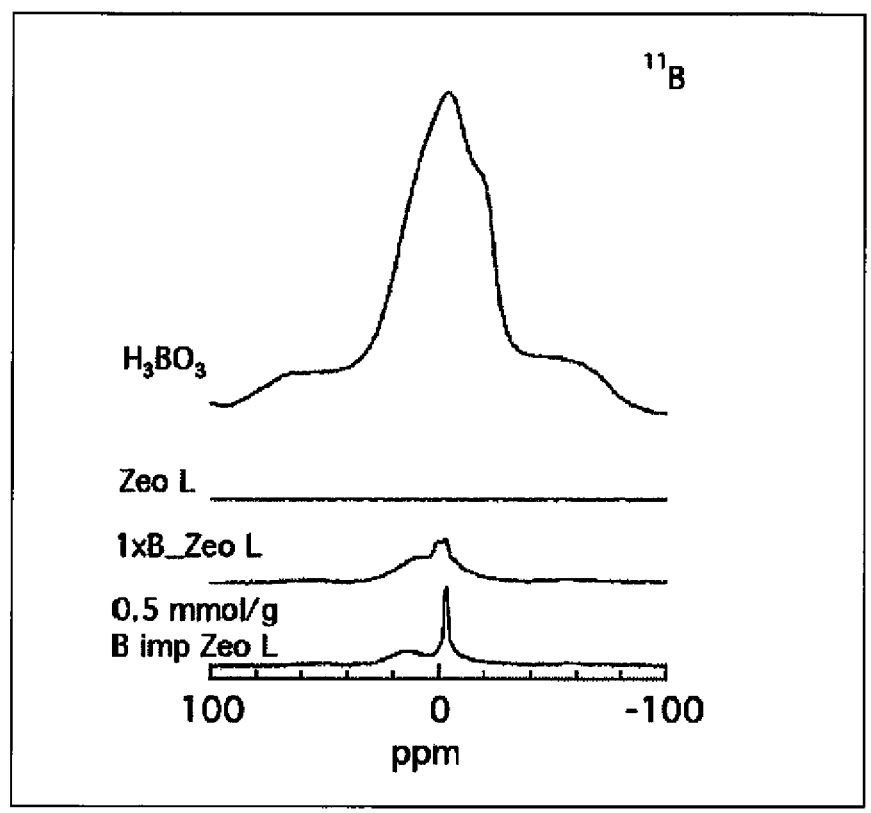
FIG. 9 $^{11}B$ Solid state NMR spectra for $H_3BO_3$, zeolite L (Zeo L), zeolite L ion-exchanged with 5% $H_3BO_3$ solution (1×B-Zeo L) and zeolite L impregnated with $H_3BO_3$ at the concentration of 0.5 mmol of $H_3BO_3$/gram of zeolite L (0.5 mmol/g B imp Zeo L).

The Zeolite-L with potassium as a non-framework cation referred as Zeolite K-L form was ion-exchanged with boron either by treating it with 5% $H_3BO_3$ solution or impregnating it with 0.5 mmol of aqueous $H_3BO_3$ solution of per gram of zeolite K-L. In the ion-exchange experiment, 7.5 grams of zeolite K-L form was suspended in 5% H3BO3 aqueous solution for 6 hours at 60° C. At the end of the stirring step, the zeolite K-L was filtered and the process was repeated three times. At the end of the third filtration step, the filtrate was calcined by slowly ramping up the temperature to 450° C. over a 2 hour period and holding it at 450° C. for 2 hours. The resulting sample was referred as 1×B Zeolite L. In another aspect of this example, 1 gram of zeolite K-L-form was impregnated with 0.5 mmol of aqueous $H_3BO_3$ solution and the resulting material was kept at room temperature for 2 hours followed by heat treatment at 120° C. for two hours. Finally, the boric acid impregnated zeolite K-L-form was calcined at 450° C. for 2 h hour period and held at 450° C. for 2 hours. $^{11}B$ solid state NMR was used to follow the incorporation of boron as non-framework cation in the original zeolite K-L form. The precursor, $H_3BO_3$ gave a broad peak around 4.3 ppm, and a shift was observed in the boron-impregnated zeolite samples to −3.6 ppm in the NMR spectrum. A similar NMR signal was also present in the 1×B Zeolite L (FIG. 9).

Example 3

Temperature Programmed Desorption Analysis

Figure 10:
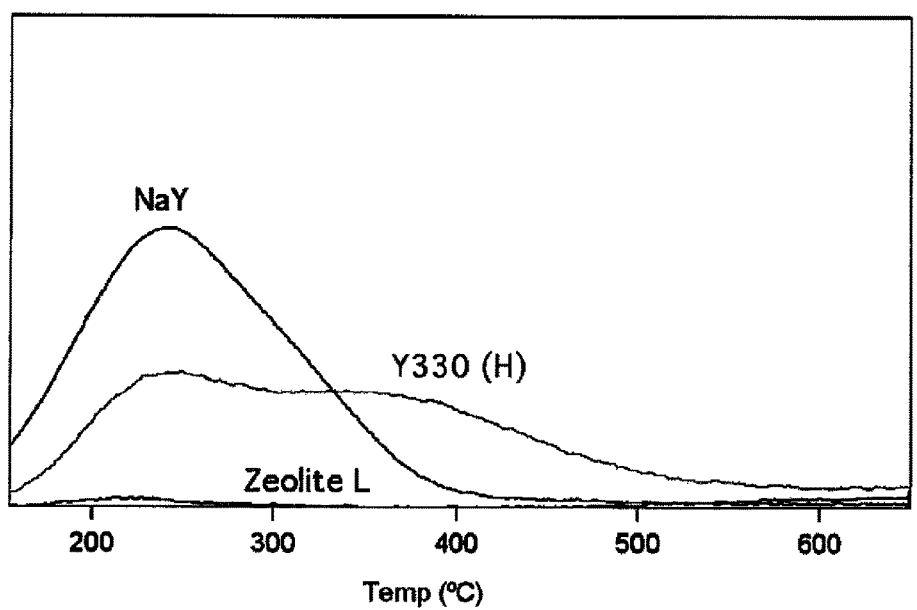
FIG. 10 $NH_3$-Temperature programmed desorption profiles of two Y-type zeolites (NaY and Y330) and a L-type zeolite.

FIG. 10 shows the Temperature Programmed Desorption (TPD) profiles of three different zeolite samples namely Tosoh Zeolite Y-330 (H-form), NaY (Zeolite CC428 from Zeolyst), and Tosho Zeolite L (K-form). These three different zeolite samples with three different non-framework elements ($H^+$, $Na^+$ and $K^+$) clearly showed distinct differences in their surface acidity as determined in their TPD profile. Zeolite Y330 contains a proton as a non-framework element and therefore is expected to have greatest amount of total acidity (weak and strong). Two types of acid sites (weak and strong) are confirmed for Y330 with two broadly overlapping peaks at around 250° C. and 370° C., with almost equal intensities. In contrast, for the NaY sample, the first peak (weak acid site) is more prominent with much less contribution from the second peak. This indicates that the strong acid sites presents in H-form of zeolite Y could be effectively neutralized with incorporation of Na through ion-exchange as in NaY zeolite. Zeolite L-K form presented only a small peak around at 230° C. corresponding to weak acid sites and showed no evidence for strong acid sites.

Apparently, the ion exchange with potassium has effectively neutralized both strong and weak acid groups in zeolite L.

Example 4

Temperature Programmed Desorption Profile of Ammonium Form of Zeolite

Figure 11:
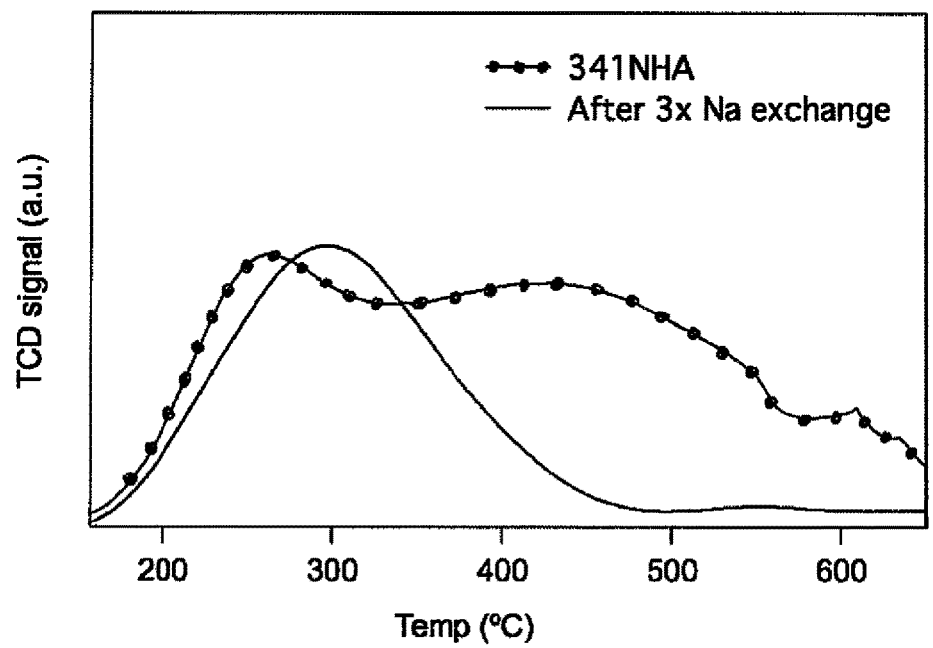
FIG. 11 $NH_3$-TPD profiles of zeolite catalyst 341NHA before and after ion-exchange using NaCl solution. The ion-exchange was carried out three time as per the protocol provided in Example 1.

FIG. 11 shows the temperature programmed desorption (TPD) profiles of 341NHA zeolite in ammonium form recorded before and after 3×Na exchange. The 3×Na exchange was carried out as described in Example 1. Elemental analysis of 341NHA zeolite before and after sodium exchange is provide in Table 4. The sodium content of 341NHA increased 60 fold after ion exchange. The 341NHA zeolite in its original ammonium form showed two broad, overlapping desorption peaks covering a wide temperature range. Upon 3×Na exchange the TPD profile showed a more refined single peak at ~300° C. This demonstrates that with sodium exchange causes the elimination of strong acid sites but the continued presence of weak to moderate acid site as in NaY (Example 3) or Na-ZSM-5 zeolites (Example 9).

Example 5

Effect of Alkali Impregnation on TPD Profile

Figure 12:
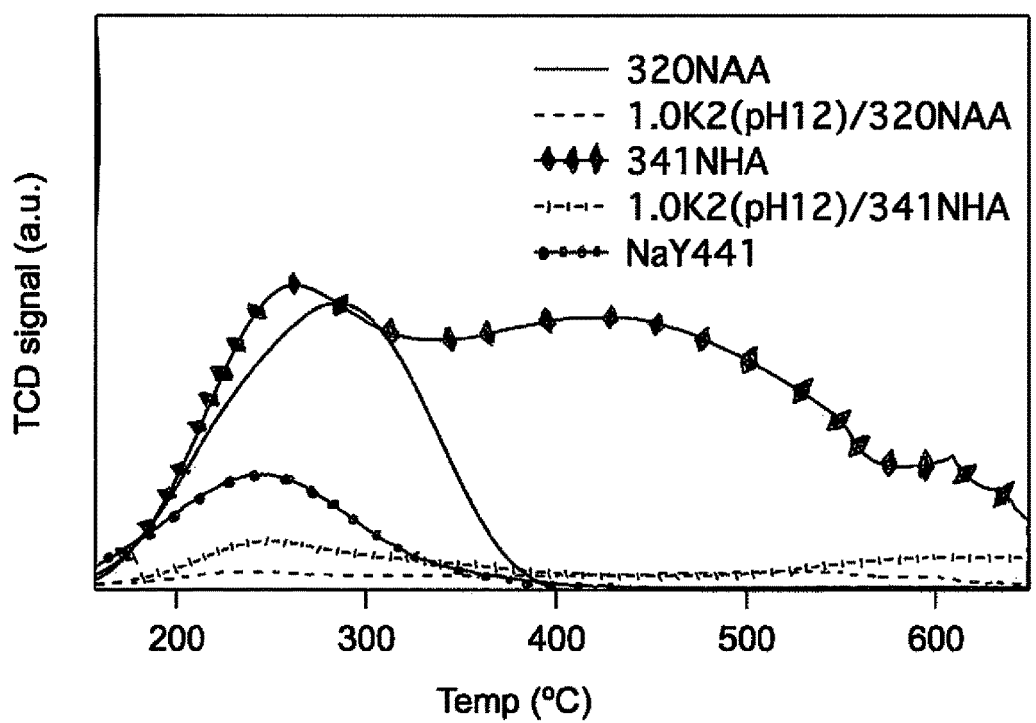
FIG. 12 $NH_3$-TPD profile of sodium form of zeolites NaY441 and 320NAA and ammonia form of zeolite 341NHA. $NH_3$-TPD profile of zeolites 320NAA and 341NHA were obtained before and after phosphate impregnation with $K_2HPO_4$. Phosphate impregnation was carried out at the concentration of 1.0 mmol of $K_2HPO_4$ per gram of zeolite catalyst.

Two new Y-type zeolites from Tosoh namely HSZ300-320NAA (Zeolite Y in sodium form) and HSZ300-341341NHA (Zeolite Y in ammonium form) were impregnated with $K_2HPO_4$ (mmol of $K_2HPO_4$/gram of zeolite) following the impregnation process as in Example 1 and their TPD profiles recorded. TPD Profiles of the original zeolite 320NAA and zeolite 341NHA exhibited similar desorption peaks around at 250-300° C., but in zeolite 341NHA, the desorption peak was much broader in the higher temperature region (FIG. 12). This confirms the presence of stronger acid sites on the surface of the original zeolite 341NHA, which should have formed from the ammonium group during the heat pretreatment before recording TPD profile. After impregnation of 1.0 mmol/g of $K_2HPO_4$, desorption peaks in the TPD profile were substantially weakened (98% reduction in zeolite 320NAA and about 95% reduction in zeolite 341NHA, demonstrating the impact of loading of $K_2HPO_4$ on the surface acidity of zeolites. Also provide in FIG. 12 is the TPD profile of zeolite NaY441

Example 6

TPD Profile of Modernite (CBV-10A) and Faujasite (CC441) Zeolites

Figure 13:
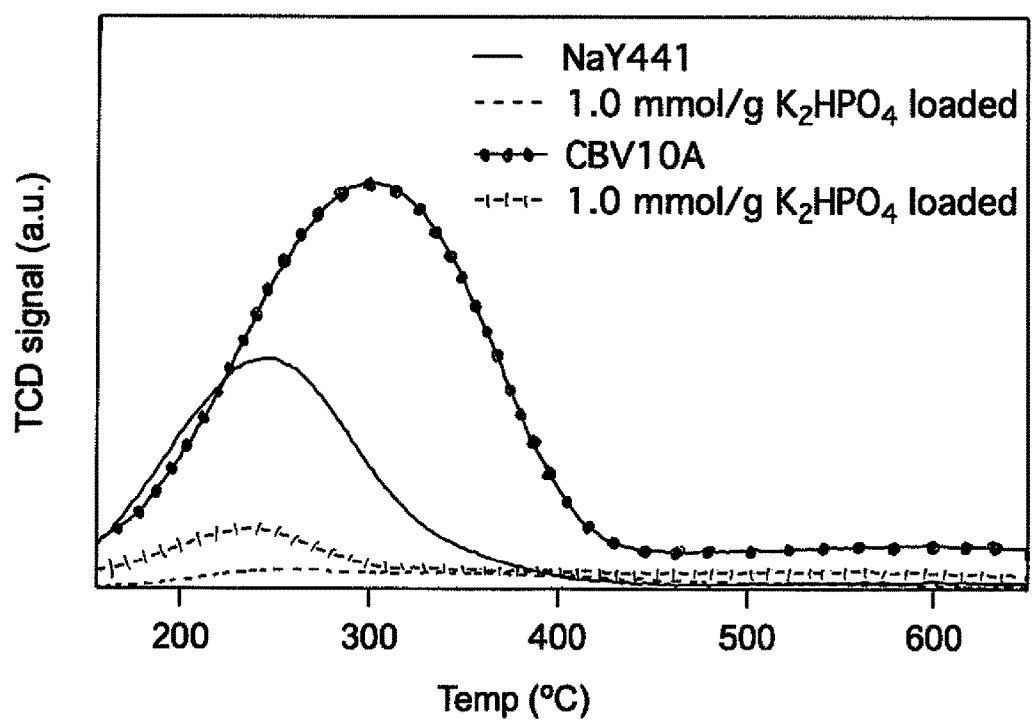
FIG. 13 $NH_3$-TPD profile of modernite catalyst (CCV-10A) and faujasite catalyst (CC441) before and after impregnation with $K_2HPO_4$. Phosphate impregnation was done using at the concentration of 1 mmol of $K_2HPO_4$ per gram of catalyst.

The $NH_3$ desorption from the parent CBV-10A and CC441 zeolites peaked at different temperatures with peak $NH_3$ desorption occurring at 350° C. for CBV-10A and at 245° C. for CC441, indicating stronger acid sites are present in CBV-10A (FIG. 13). Moreover, CBV-10A sample possessed a peak with significantly greater area than the corresponding CC441 samples for both the parent zeolite and phosphate modified samples. Phosphate impregnation was done as described in Example 1. Relative acid quantity is defined based on the integrated TPD signal for the peak with NaY CC441 taken to be unity. The relative acid quantity of CBV-10A is estimated to be 2.77. Impregnation of $K_2HPO_4$ substantially decreased this value to 0.17 from 2.77. This confirms the effective reduction of acidity by modification involving salt impregnation. It is however, still higher than the value for 1.0 mmol/g $K_2HPO_4$/NaY CC441 zeolite preparation (0.04), suggesting residual acidity remains even after the loading of $K_2HPO_4$ in NaY CBV-10A zeolite preparation.

Figure 14:
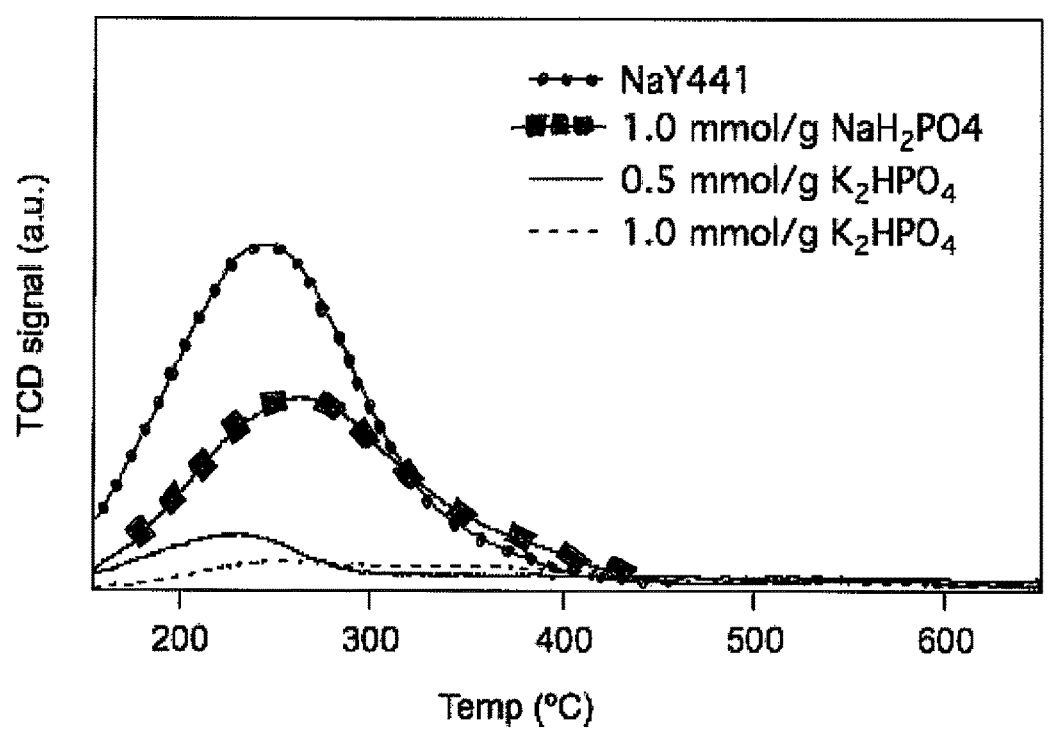
FIG. 14 $NH_3$-TPD profiles of modified NaY catalysts with different alkali loading (1.0 $NaH_2PO_4$, 0.5 $K_2HPO_4$ and 1.0 $K_2HPO_4$)

FIG. 14 shows the TPD profiles of modified NaYCC441 zeolite with different alkali loading (1.0 $NaH_2PO_4$, 0.5 $K_2HPO_4$ and 1.0 $K_2HPO_4$). Alkali loading was done as described in Example 1. As total alkali loading was increased, the desorption peak at 150-350° C. with shoulder at 350-400° C.) became weaker and 1.0 $KH_2PO_4$ exhibited almost no noticeable peak. The desorption peaked at around 270° C. for $NaH_2PO_4$, while it was ~230° C. for 0.5 $KH_2PO_4$, reflecting some difference in acid strength between these modified NaY zeolites in addition to the total acid amount.

Figure 15:
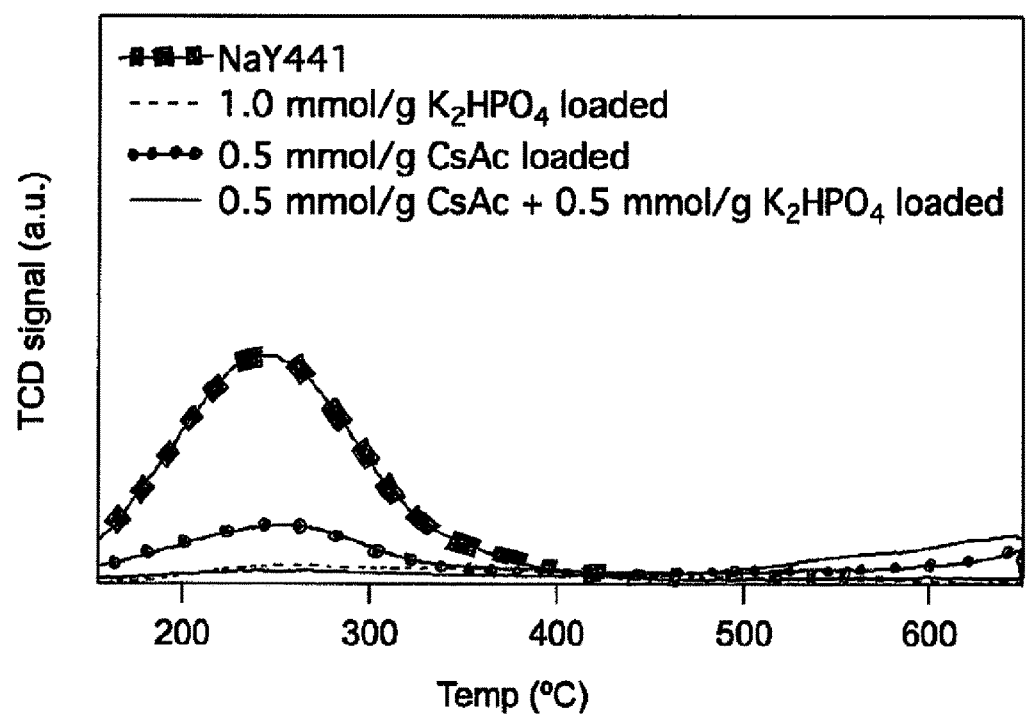
FIG. 15 $NH_3$-TPD profile of ceasium acetate loaded NaY catalysts

FIG. 15 shows the effect of loading of cesium acetate alone or in combination with $K_2HPO_4$ on the TPD profile of NaY CC441. Loading of 0.05 mmol CsAc/g of zeolite greatly reduced the surface acidity of NaY CC441 as determined from TPD profile. Relative acid quantity based on the peak area decreased from 1.0 (basis) to 0.23. This proves the effectiveness of cesium modification on the surface acidity of the original NaY zeolite. Co-loading of CsAc and $K_2HPO_4$ further decreased the acidity to <0.01 which is comparable to the surface acidity of 1.0 mmol/g $K_2HPO_4$ loaded NaY 441 sample.

Figure 16:
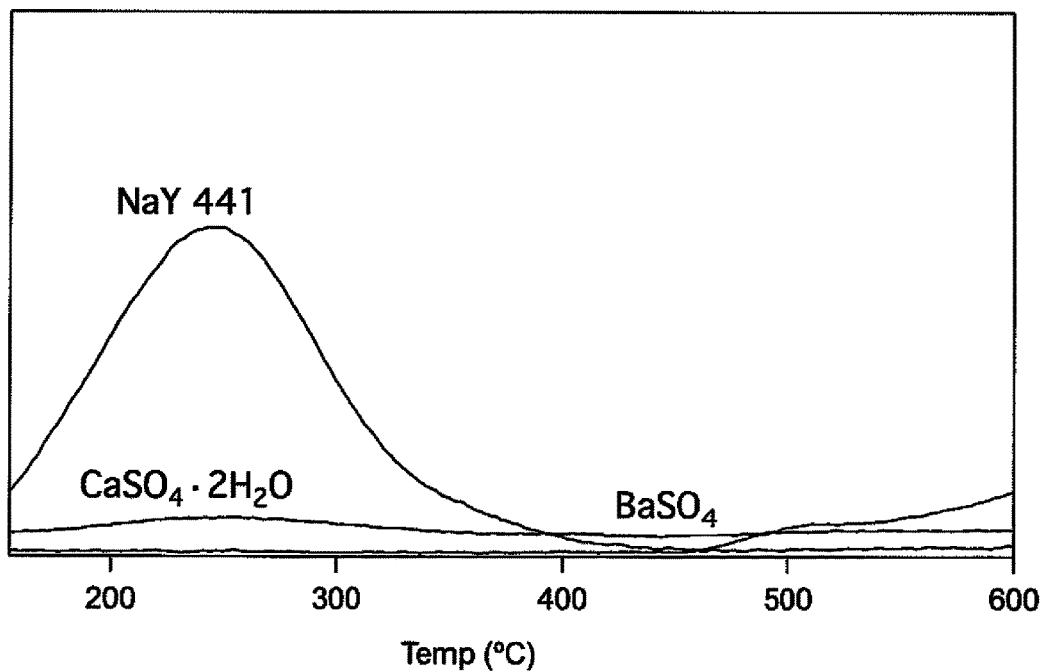
FIG. 16 $NH_3$-TPD Profile of NaY 441 zeolite before and after ion-exchange with $CaSO_4.2H_2O$ and $BaSO_4$.
Figure 17:
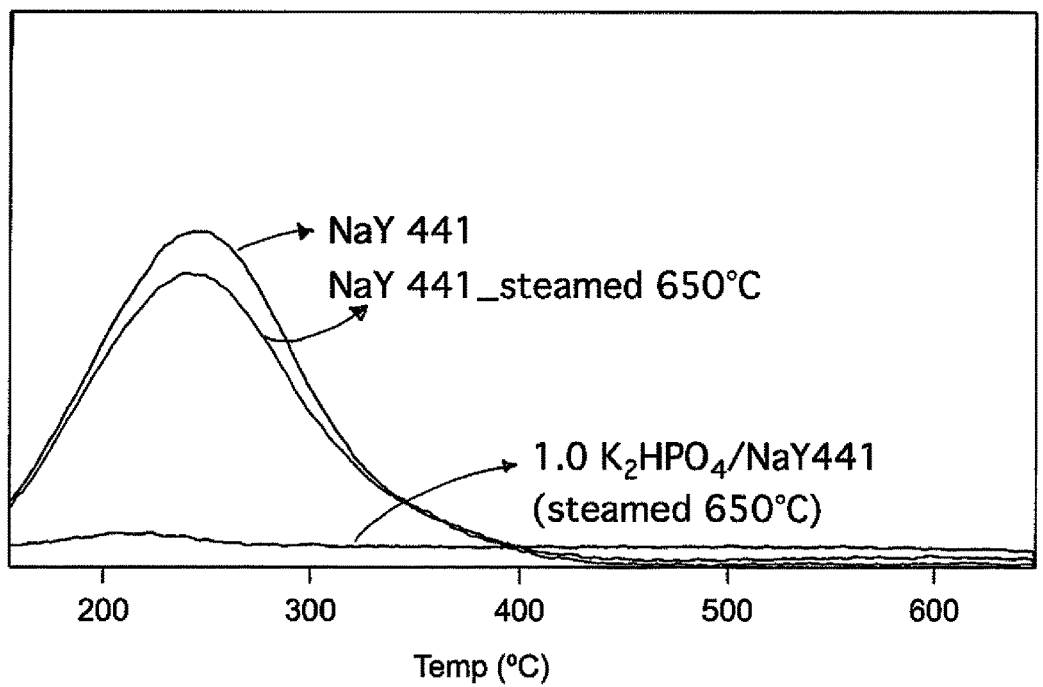
FIG. 17 $NH_3$-TPD Profile of NaY 441 zeolite after steaming and impregnation with alkali salt.
Figure 18:
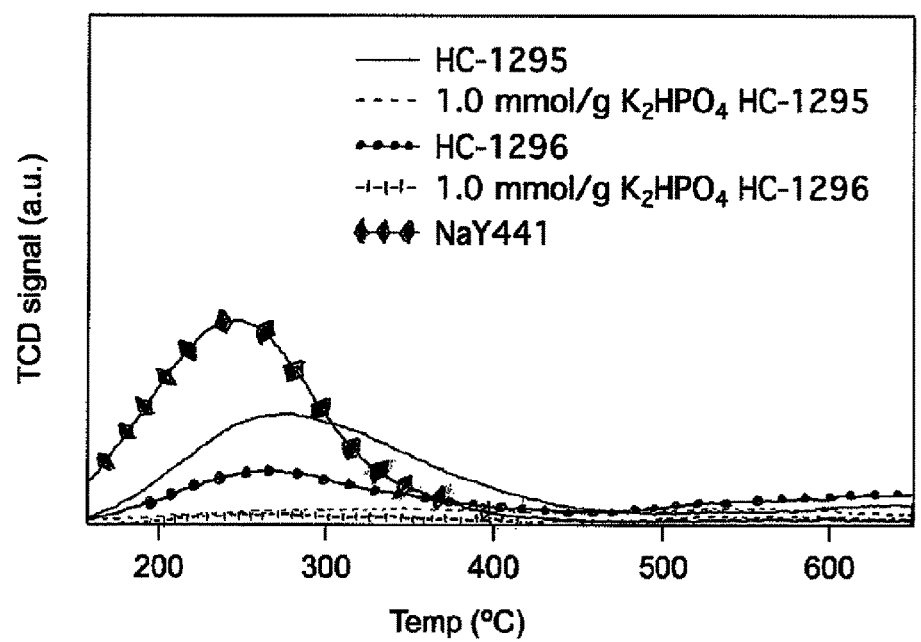
FIG. 18 TPD profiles of new NaY catalysts HC1295 (SiO2/Al2O3~10.8) and HC-1296 (SiO2/Al2O3~23.2) modified with and without $K_2HPO_4$ loading FIG. 19 $NH_3$-TPD profile of Na-ZSM-5 before and after one time ion exchange (1×Na Na-ZSM-5) and phosphate impregnation with $K_2HPO_4$. Phosphate impregnation was done at three different concentrations: 1 mmol $K_2HPO_4$ per gram of catalyst; 1 mmol $K_2HPO_4$ per gram of catalyst; and 1 mmol $K_2HPO_4$ per gram of catalyst. Also shown in this figure is $NH_3$-TPD profile of a Y-type zeolite (NaY441) after phosphate impregnation. The phosphate impregnation in the NaY441 zeolite was done at the concentration of 1 mmol phosphate for 1 gram of NaY441 zeolite catalyst.

FIG. 16 shows the $NH_3$-TPD Profile of NaY 441 zeolite before and after ion-exchange with $CaSO_4.2H_2O$ and $BaSO_4$. Four alkali sulfate salts ($MgSO_4$, $CaSO_4.2H_2O$, $BaSO_4$, and $K_2SO_4$ were impregnated following the standard process. Both $CaSO_4.2H_2O$ and $BaSO_4$ removed the acidity from the surface of NaY 441 zeolite as measured by $NH_3$-TPD technique.

Example 7

NH3-TPD Profile of NaY441 Zeolite after Steaming and Impregnation

Steaming treatment was performed on NaY (CC441) zeolite in a tube furnace by flowing air saturated with $H_2O$ (~20 Torr) at 650° C. for 6 h. The temperature of the sample was increased at a rate of 5° C./min. NH3-TPD was performed on NaY (CC441) zeolite steamed at 650° C. showed a slight reduction of $NH_3$ peak at 250° C. indicative of reduced acidity of the zeolite due to dealumination from the framework of zeolite. Impregnation of steamed NaY C441 zeolite with 1.0 mmol $K_2HPO_4$ completely eliminated the acidity of the steamed NaY 441 zeolite as measured by NH3-TPD profile.

Example 8

TPD Profiles of Zeolites with Higher $SiO_2/Al_2O_3$ Ratio

The zeolite HC1295 has a $SiO_2/Al_2O_3$ ratio of ~10.8 and zeolite HC1296 has a $SiO_2/Al_2O3$ ratio of ~23.2. Higher $SiO_2/Al_2O_3$ ratio samples gave a smaller NH3 desorption peak, which is reasonable as aluminum in the framework is the origin of charge deficiency that that can be compensated with cations (e.g., $Na^+$ or $H^+$). On the other hand, despite its less overall acid quantity, these zeolites with higher $SiO_2/Al_2O_3$ ratio appear to have stronger acid sites than zeolite CC441 with lower $SiO_2/Al_2O_3$ ratio. While desorption from the CC441 samples peaked at 250° C., desorption from HC1295 and HC1296 zeolites samples peaked at 270° C. After impregnation, no significant peak was found in these zeolites with higher $SiO_2/Al_2O_3$ ratio indicative of a substantial reduction in acidity similar to zeolite CC441 with lower $SiO_2/Al_2O_3$ ratio.

Example 9

Ion Exchange and Salt Impregnation Studies with ZSM-5 Zeolite

ZSM-5 zeolite is synthesized using tetrapropylammonium as a non-framework cation and therefore it is initially synthesized in ammonium form and subsequently ion-exchanged with NaCl to sodium form (Na-ZSM-5). NaZSM-5 is commercially available from Tricat.

Figure 19:
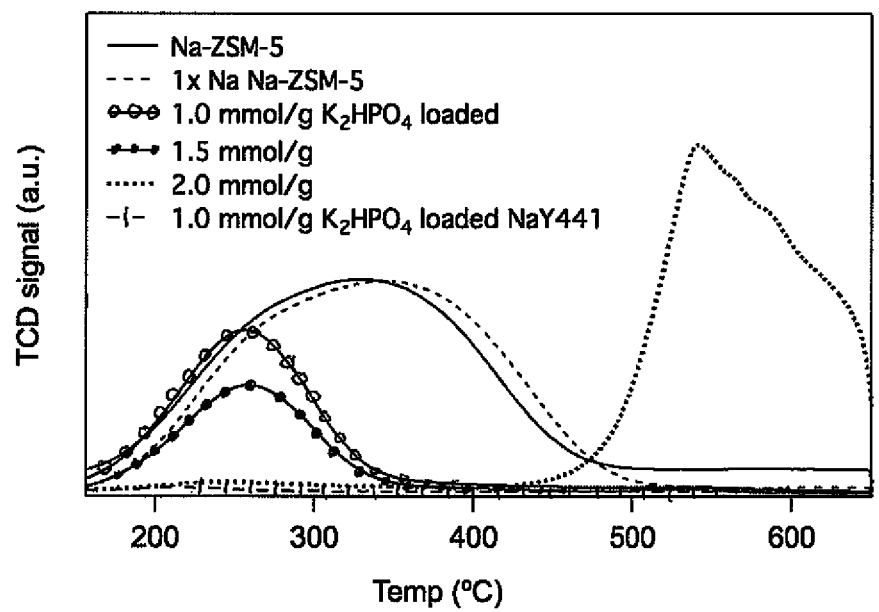
Figure 21:
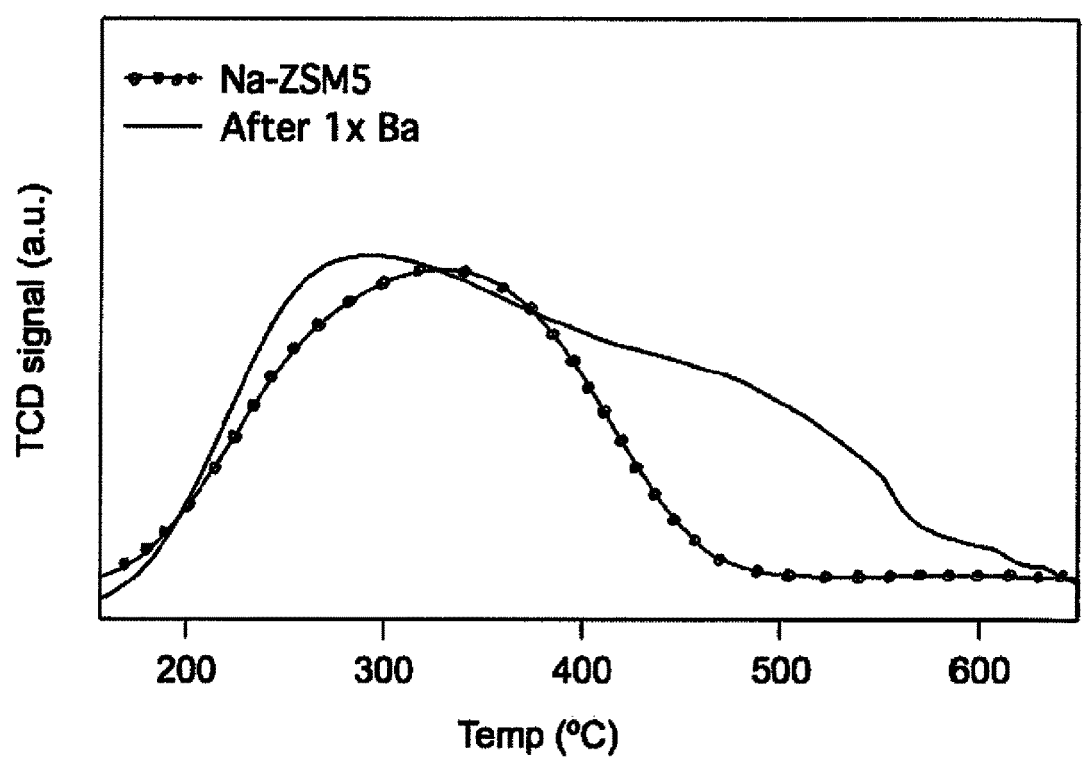
FIG. 21 $NH_3$-TPD profile of Na-ZSM-5 before and after barium exchange. Barium exchange was carried out one time using the protocol as in Example 1.

As shown in FIG. 19, the original Na-ZSM-5 zeolite showed a large, broad desorption peak at 350° C. demonstrating the strong interaction of probe molecule $NH_3$ with Na-ZSM-5. Further sodium chloride treatment of commercially available H-ZSM-5 or $NH_4$—ZSM-5 was done as follows: 15 grams of zeolite ZSM-5 obtained from Na-ZSM-5 was dispersed in 200 ml of 1M sodium chloride solution and stirred at room temperature for 6 hours. In a modified version of this ion-exchange protocol, it is possible to conduct this stirring step at 60° C. for an hour or for up to 6 hours. At the end of the stirring step, the zeolite Na-ZSM-5 was filtered and washed with excess amount of water until chloride free. The solid material was dried at 220 C for 2 hours. This ion-exchange process is repeated for three times in total. The final filtered solid was calcined by slowly increasing the temperature to 450° C. over a 2 hour period and held at 450° C. for 2 hours. The calcined material is referred as 1×Na Na-ZSM-5. Subjecting Na-ZSM-5 from commercial supplier to additional 1×Na exchange did not reduce its surface acidity as measured from TPD profile; in fact, the ammonium desorption peak in the TPD profile was slightly shifted toward higher temperature side. Similarly, with one time barium exchange, the TPD profile was slightly broadened in the temperature range above 400° C. (FIG. 21).

Impregnation of Na-ZSM-5 zeolite received from commercial supplier with $K_2HPO_4$ (1.0 mmol $K_2HPO_4$/g of catalyst) significantly reduced the surface acidity of Na-ZSM-5 zeolite as determined from its TPD profile. After impregnation of 1.0 mmol $K_2HPO_4$/g of zeolite, desorption substantially reduced and a peak was found around 250° C., as opposed to the desorption peak at 350° C. in the unmodified Na-ZSM-5 zeolite, suggesting the retention of weak acid sites after salt impregnation. This confirms that salt impregnation was effective in suppressing the acidity on the surface of Na-ZSM-5. Nevertheless, the impact of salt impregnation on Na-ZSM-5 zeolite was not as much as the effect of salt impregnation on the surface acidity of NaY441, a sodium form of Y-type zeolite, where almost no noticeable peak was detected in the TPD profile after loading of 1.0 mmol $K_2HPO_4$/g of zeolite. By means of further increasing the phosphate concentration in the impregnation process, the surface acidity of Na-ZSM-5 could further be reduced. Thus by increasing the phosphate concentration in the impregnation process to 1.5 mmol $K_2HPO_4$/g zeolite, the surface acidity of Na-ZSM-5 was reduced from the level reached with phosphate concentration at 1.0 mmol $K_2HPO_4$/g zeolite. Increasing the phosphate concentration in the impregnation process to 2.0 mmol $K_2HPO_4$/g zeolite almost completely removed the surface acidity as no distinct as no distinct peak was present in the TPD profile below 500° C. However, loading phosphate at the concentration of 2.0 mmol $K_2HPO_4$/g zeolite showed an anomalously large peak around 550° C. It is most likely the result of decomposition of $K_2HPO_4$ upon heating at temperature above 500° C.

Figure 20:
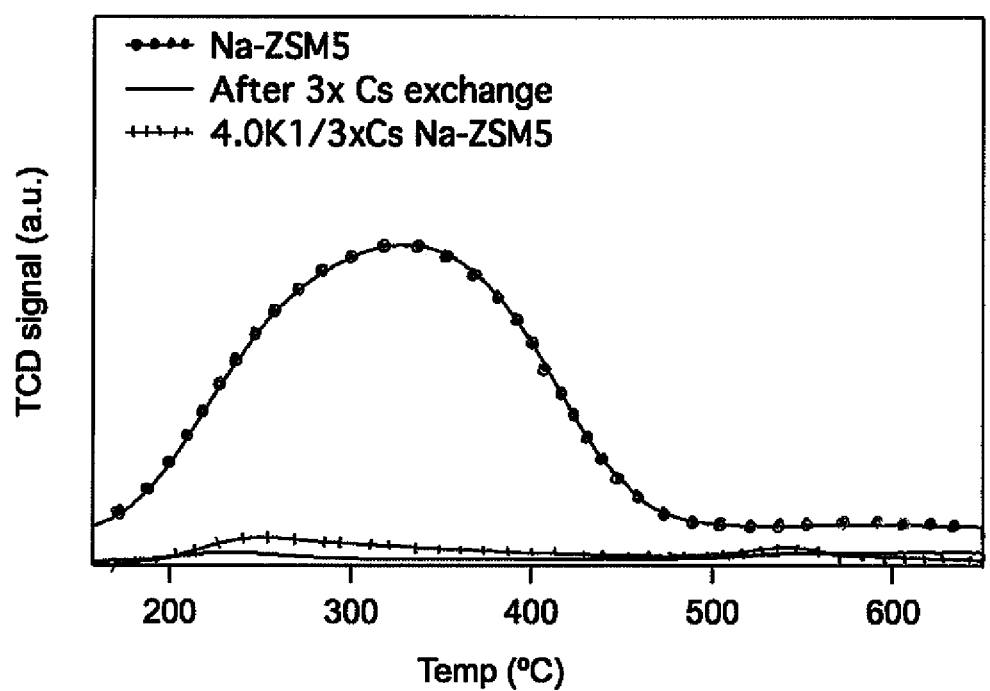
FIG. 20. $NH_3$-TPD profile of fresh Na-ZSM-5 catalyst, Na-ZSM-5 catalyst after ion exchange with CsCl and Na-ZSM-5 catalyst after ion exchange with CsCl followed by phosphate impregnation. Ion exchange with CsCl was done as per the protocol in the Example 1. The phosphate impregnation was done using $KH_2PO_4$ at the concentration of 4.0 mmol of $KH_2PO_4$ per gram of Na-ZSM-5 zeolite catalyst.

Na-ZSM5 zeolite was ion exchanged with cesium chloride (CsCl) using the following protocol: 5 gram of Na-ZSM5 was suspended in 200 ml of 0.5M CsCl solution and stirred overnight (>12 hours) and filtered. The filtrate was washed with 1.5 L of water and calcined at 450° C. for 2 hours. The calcination temperature of 450° C. was reached slowly in the course of 2 hours. These process steps were repeated 3 times. The TPD profile of Cs-exchanged NaZSM-5 zeolite is shown in FIG. 20. The original Na-ZSM-5 exhibited a wide desorption peak around at 340° C. After 3×CsCl treatment no noticeable peak was found. The disappearance of desorption peak in the TPD profile should reflect the successful replacement of Na with Cs. Interestingly, after phosphate loading (4.0 mmol $KH_2PO_4$/g of zeolite) onto 3×Cs Na-ZSM-5, a desorption peak, although still very small, appeared implying interaction of $KH_2PO_4$ with zeolite support might be inducing some sites for NH3 adsorption and thereby causing a slight bump in the TPD profile of 3×Cs Na-ZSM-5 zeolite after phosphate impregnation (FIG. 20).

Example 10

CO2-TPD Profile of Original Na-ZSM-CO2-TPD

Figure 22:
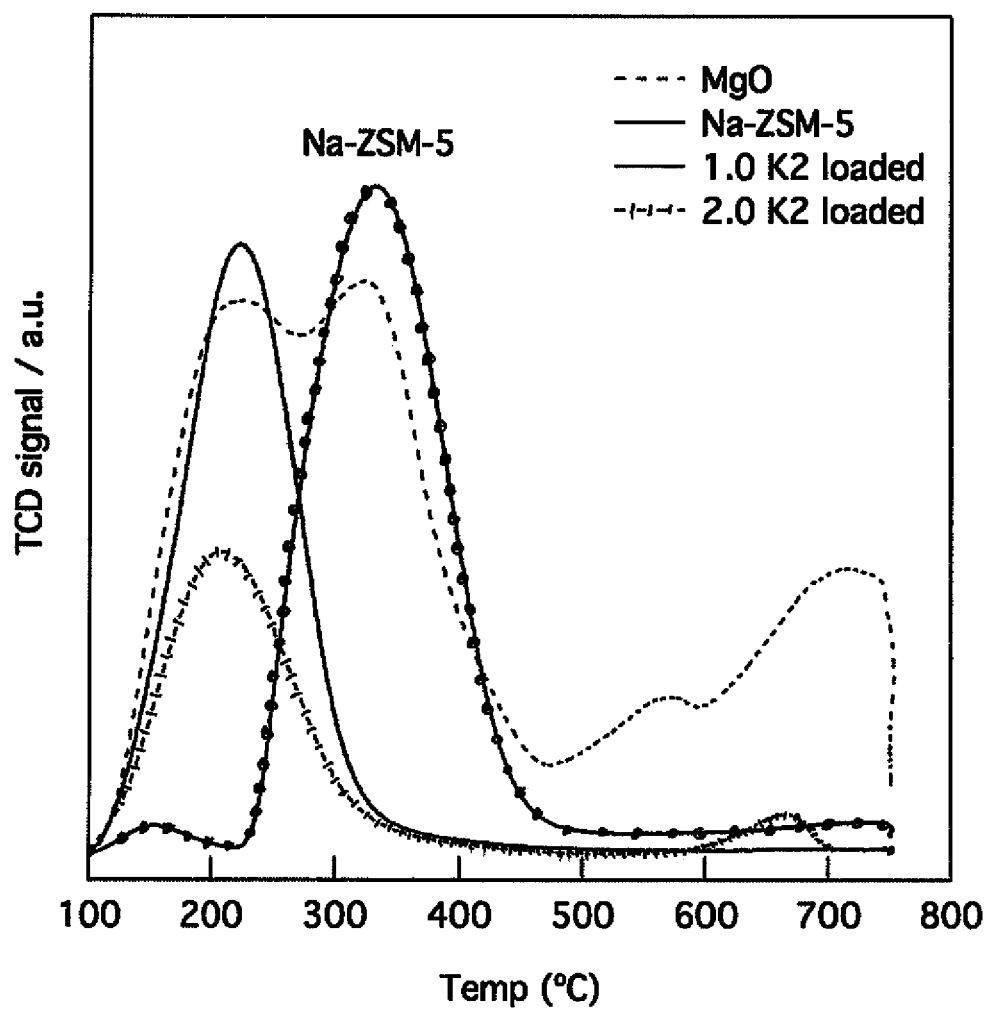
FIG. 22 $CO_2$-TPD profiles of modified Na-ZSM-5 catalysts. Modification of the Na-ZSM-5 catalyst was carried out by impregnation of $K_2HPO_4$ at two different concentrations (2 mmol of $K_2HPO_4$ per gram of Na-ZSM-5 and 1 mmol of $K_2HPO_4$ per gram of NaZSM-5) as explained in the Example 1. Also shown in this figure is a CO2-TPD profile of MgO.

FIG. 22 provides the $CO_2$-TPD profile of original Na-ZSM-5, 1.0 and 2.0 mmol/g $K_2HPO_4$ loaded Na-ZSM-5 samples along with MgO as a reference. Na-ZSM-5 showed a clear desorption peak at around 350° C. and another smaller peak at 150° C. It is reported that cations in the zeolite structure could enhance adsorption of polar molecules such as $CO^2$ because of strong electrostatic interactions. This peak shifted to lower temperature region (220-250° C.) upon loading of $K_2HPO_4$ salt, and the peak decreased with greater loading of $K_2HPO_4$ (2.0 mol/g). Initially it was expected that an increase in the basicity of zeolite resulting from $K_2HPO_4$ loading would allow the growth of a desorption peak or shift it to high temperature in a $CO_2$-TPD profile. The observed result was opposite of this expectation and this might be related physical changes on the surface of zeolite due to salt loading. Higher salt loading might reduce the measurable surface area of zeolite.

Example 11

Phenol-TPD Profiles for Na-ZSM-5 and 4.0K1/NaZSM-5 Catalysis

An effort was made to characterize the "acid-base" pair on the surface of ZSM-5 zeolite through temperature programmed desorption technique using phenol as a probe. Preliminary tests on Phenol-TPD experiment was performed using Autochem 2920 equipment. Phenol was introduced into the flask attached to the heating jacket and the vapor generator of the instrument was kept at 60° C. Phenol vapor pressure is estimated to be around ~6 mbar based on Antoine Equation. The sample loop filled with phenol vapor was introduced to the sample cell at 50° C. after degassing 0.3 grams of the samples at 450° C. for 2 hours. Temperature programmed desorption was performed by ramping the temperature at a rate of 10° C./min to 650° C. Na-ZSM-5 and modified Na-ZSM-5 (4.0 mmol $KH_2PO_4$/g Na-ZSM-5) were analyzed).

Figure 23:
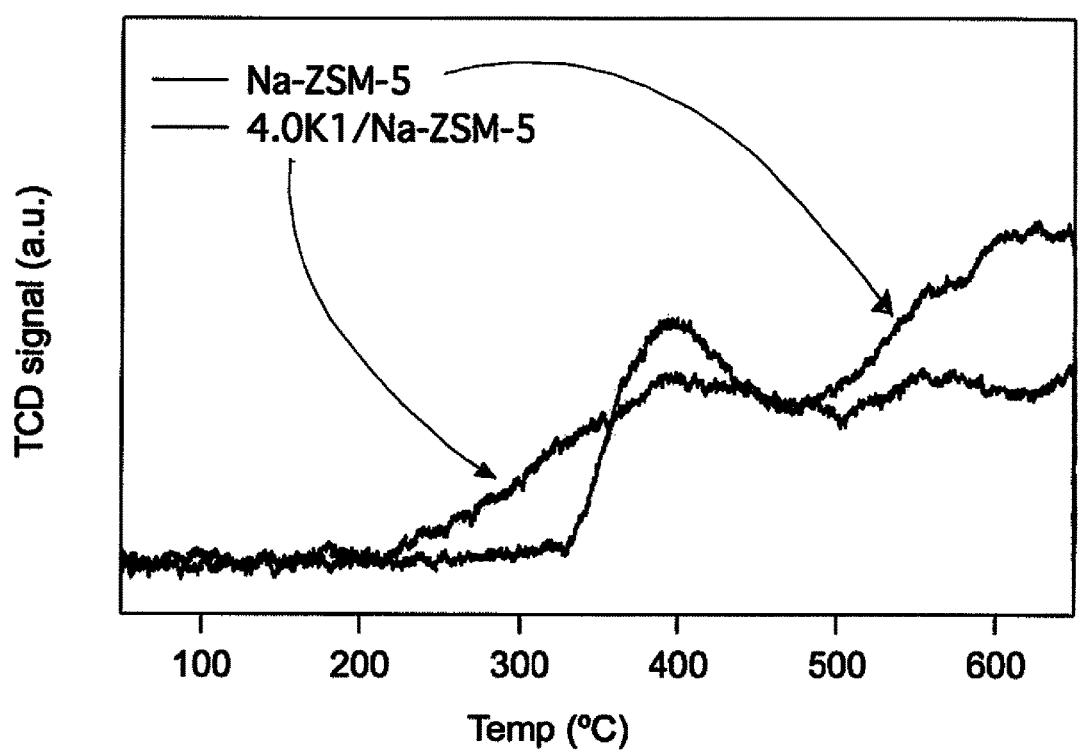
FIG. 23 Phenol-TPD profile of Na-ZSM-5 zeolite catalyst before and after phosphate impregnation. Phosphate impregnation was done with $KH_2PO_4$ at the concentration of 4 mmol $KH_2PO_4$ per gram of Na-ZSM-5 catalyst.

FIG. 23 presents phenol-TPD profiles for Na-ZSM-5 and 4.0 mmol $KH_2PO_4$/g Na-ZSM-5 zeolites. Compared to typical NH3-TPD profiles, signals in the Phenol-TPD profiles were more than 10 times weaker, resulting in poorer signal-to-noise ratio. This ratio might be improved by tuning instrument analytical parameters such as flask temperature, desorption temperature ramping rate, sample loading etc. The unmodified Na-ZSM-5 zeolite showed the first desorption peak from 330° C. to 470° C., and the signal kept rising in the range of 500° C. to 650° C. On the other hand, in 4.0 mmol $KH_2PO_4$/g Na-ZSM-5 zeolite, desorption started at around 220° C. and constantly increased until it reached 400° C. and it remained stable till the end of the analysis at 650° C. The unmodified Na-ZSM-5 showed higher temperature for initial desorption, indicating phenol-surface species are more stable in the unmodified Na-ZSM-5 compared to that of 4.0 mmol $KH_2PO_4$/g Na-ZSM-5 zeolite. The quantification of various catalysts for the acidity by NH3 TPD is shown in Table 5.

Example 12

Measurement of BET Surface Area in Various Zeolites

For obtaining BET surface area, nitrogen adsorption-desorption measurement were performed using Micromeritics ASAP 2020 at 77K after degassing the 20-60 mesh samples at 350° C. for 4 h using vacuum. As shown in Table 6, a decrease in the surface area was observed in all zeolite samples after phosphorous doping suggesting that a substantial portion of micro pores of zeolites is blocked after this phosphate doping.

Example 13

Catalytic Dehydration of Lactic Acid Using Modified NaZSM-5 Zeolite

NaZSM-5 is a commercially available zeolite from Tricat. In this set of experiments, the efficiency of modified NaZSM-5 zeolites in vapor phase dehydration reaction was determined under various process conditions in terms of their conversion efficiency and selectivity for various products as explained in Table 1.

In the first set of experiments, NaZSM-5 zeolite was modified by impregnating one of the five different potassium phosphate compounds as provided in Table 7 and each of the modified NaZSM-5 zeolites was tested for their efficiency in vapor phase dehydration reaction. The vapor phase dehydration reaction using lactic acid as a reactant was carried out using the following experimental parameters: Gas flow rate: 55 cc/min; Feed: Heat treated 20% USP lactic acid; Feed flow rate: 0.1 cc/mi; Temp: 330° C.; Catalyst volume: 3 cc. As the results shown in Table 7 indicate among the five different potassium phosphate compound tested, monobasic potassium phosphate ($KH_2PO_4$) at 2 mmol/g of zeolite was found to be efficient doping agent in terms of resulting in the formation of acetaldehyde as the only major side product in the vapor phase dehydration reaction using lactic acid for the production acrylic acid.

Having established that $KH_2PO_4$ is the desirable doping agent among the five different potassium phosphate compound tested in the modification of NaZSM-5 zeolite, in the next set of experiments, the NaZSM-5 zeolite was impregnated with different amounts of $KH_2PO_4$ to determine the appropriate amount of $KH_2PO_4$ loading. The vapor phase lactic acid dehydration reaction with modified NaZMS-5 was carried out using the following process parameters: Gas flow rate: 55 cc/min; Feed: Heat treated 20% USP lactic acid; Feed flow rate: 0.1 cc/mi; Temp: 330° C.; Catalyst volume: 3 cc. As the results shown in Table 8 show the NaZSM-5 catalyst modified with $KH_2PO_4$ at the concentration of 4 mmol/g of zeolite was found to be highly efficient in terms of eliminating the side products other than acetaldehyde, decreasing the selectivity for acetaldehyde and causing a proportional increase in the selectivity for acrylic acid.

Table 9 shows the effect of feed concentration on efficiency of vapor dehydration of lactic acid feed using modified zeolite 4 mmol $KH_2PO_4$/g NaZSM-5 with following process parameters: Gas flow rate: 55 cc/min; Feed: Heat treated USP lactic acid; Feed flow rate: 0.1 cc/mi; Temp: 330° C.; Catalyst volume: 3 cc. Three different aqueous solutions with varying bio-based aqueous lactic acid concentrations (15 weight %, 20 weight % and 25 weight %) were tested in the dehydration reaction for acrylic acid selectivity in a ½" titanium reactor in trickle bed mode without a preheating zone and titanium wool as catalyst bed support. The feed was subjected to heat treatment for full monomer conversion. NaZSM5 catalyst received from Tricat was modified through incipient impregnation technique and used in the dehydration reaction. An aqueous solution containing 4.0 mmoles of KH2PO4 was impregnated into 1 gram of NaZSM-5 catalyst through drop wise addition. The KH2PO4 impregnated NaZSM-5 catalyst was calcined at 250° C. and subsequently used in the lactic acid dehydration reactor.

Table 10 shows the effect of temperature on the dehydration reaction catalyzed by modified NaZSM-5 catalyst.

Table 11 shows the effect of carrier gas flow rate on the dehydration reaction catalyzed by modified NaZSM-5 catalyst.

Table 12 shows the effect of carrier gas type on the dehydration reaction catalyzed by modified NaZSM-5 catalyst.

Table 13 shows the effect of calcination temperature on the dehydration reaction catalyzed by modified NaZSM-5 catalyst.

Figure 24:
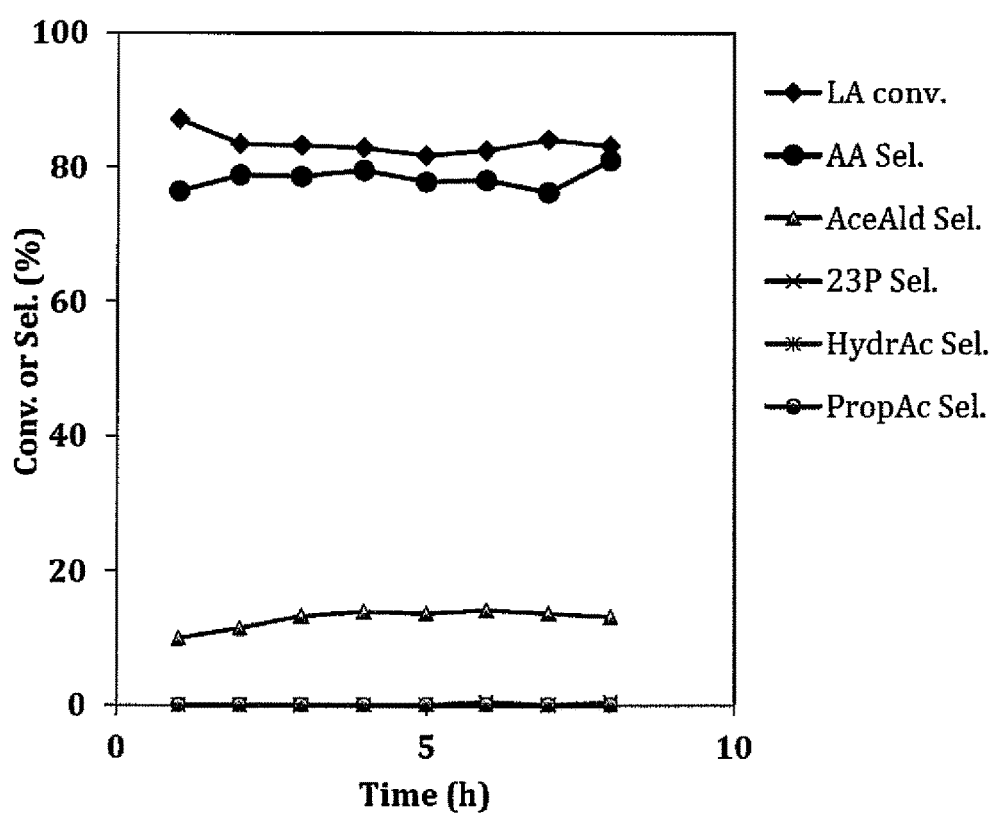
FIG. 24 Time course of LA conversion and normalized weight selectivity of major products for Na-ZSM-5 catalyst impregnated with $KH_2PO_4$ at the concentration of 4 mm $KH_2PO_4$ per gram of Na-ZSM-5 catalyst.

FIG. 24 shows time course of LA conversion and normalized weight selectivity of major products for Na-ZSM-5 catalyst impregnated with $KH_2PO_4$ at the concentration of 4 mm $KH_2PO_4$ per gram of Na-ZSM-5 catalyst.

Example 14

X-Ray Diffraction Pattern of Modified NaZSM-5 Zeolite

Figure 25:
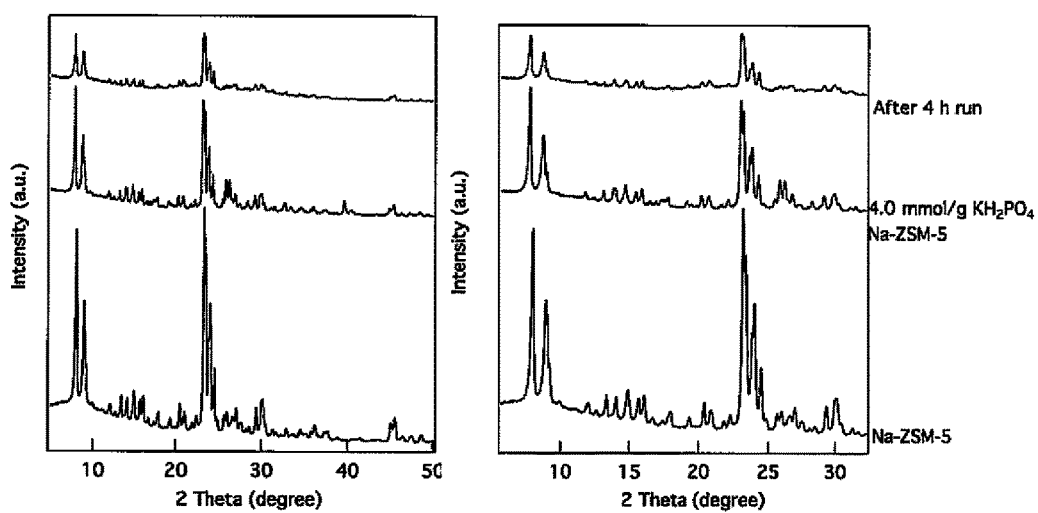
FIG. 25 X-Ray diffraction pattern of fresh Na-ZSM-5 catalyst (Na-ZSM-5), Na-ZSM-5 catalyst after impregnation with $KH_2PO_4$ (4.0 mmol/g $KH_2PO_4$ Na-ZSM-5) and spent catalyst after 4 h run (After 4 h run). Impregnation was done at the concentration of 4 mmol of $K_2HPO_4$ per gram of Na-ZSM-5.

FIG. 25 shows the x-ray diffraction pattern of NaZSM5 zeolite as received from the commercial supplier, fresh NaZSM-5 catalyst after $KH_2PO_4$ impregnation and the spent catalyst after its use for four hours in a lactic acid dehydration reactor. As the x-ray diffraction pattern indicates, there was no loss of crystalline phase of Na-ZSM-5 catalyst either as a result of $KH_2PO_4$ impregnation or as a result of calcination at elevated temperature followed by its use in the lactic acid dehydration reactor for four hours. Both fresh and spent catalyst exhibited only the patterns of MFI zeolite frame work, and no other major peak was found in the X-ray diffraction pattern. In the fresh catalyst, one small peak was found at 39.6° and it disappeared after the reaction run. It might be attributed to some potassium or phosphate species, but we were unable to find any reasonable match in the database.

Example 14

Phosphorus Analysis in the Product of Dehydration Reaction

Elemental analysis was performed on hourly basis on the reactant stream from lactic acid dehydration reactor to determine if phosphorus loaded on NaZSM-5zeolite leaches into the product stream during the reaction period. The result of this phosphorus analysis is provided in Table 14. Among eight samples, three samples did not contain any detectable amount of phosphorus. Low concentration (0.1-0.3 mg/L) of the phosphorus was detected for other five samples. This phosphorus that leached out during the four hours of dehydration reaction only accounted for <0.002% of the phosphorus initially present in the catalyst (approximately 4 mmol per gram based on preparation conditions). Thus leaching of phosphorus from the catalyst occurred during the catalytic dehydration reaction; however, the observed phosphorus leaching is inconsequential at the time scale over which the experiments were conducted.

Example 15

Catalytic Dehydration of Lactic Acid Using Modified NaNH4CZP27 Zeolite

NH4CZP27 zeolite from Clariant with SiO2/Al2O3 ratio of ~27 is in ammonium form. Ion exchange was performed on this zeolite to convert it into a sodium form using the following protocol: 10 gram of NH4CZP27 was dissolved in 200 ml of 1.0 M NaCl solution and stirred at 60° C. overnight (>12 hours) and filtered. The filtrate was washed with 1.5 L water and calcined slowly ramping the temperature to 450° C. for 2 hours and holding it at that temperature for 2 hours. This process was repeated three times and the resulting 3×Na-NH4CZP27 was impregnated with potassium monophosphate at the concentration of 4.0 mmolKH2PO4/g of 3×Na-NH4CZP27 zeolite. The conversion efficiency and selectivity of modified 3×Na-NH4CZP27 for various products in a vapor phase dehydration reaction using lactic acid as a reactant is shown in Table 15.

Example 16

Figure 26:
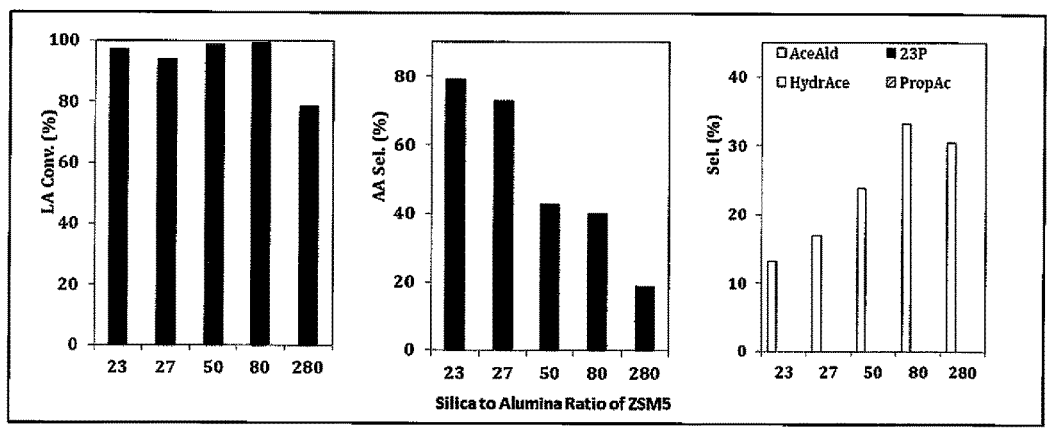
FIG. 26 Effect of $SiO_2/Al_2O_3$ ratio in various ZSM-5 zeolite catalyst on overall lactic acid conversion, normalized acrylic acid weight selectivity and normalized weight selectivity for major side products. Only acetaldehyde was detected as a major side products and the other side products such as 2,3-pentanedione, hydroxyl acetic acid and propionic acid were undetectable. The various ZSM-5 catalysts used in this dehydration reaction were impregnated with $KH_2PO_4$ at the concentration of 4 mmol $KH_2PO_4$ per gram of Na-ZSM-5 catalyst.

Effect of Silica to Alumina Ratio in the ZSM5 Catalyst on the Dehydration Reaction ZSM5 zeolites of different silica ($SiO_2$) to alumina ($Al_2O_3$) ratio were evaluated for their efficiency in the lactic acid dehydration reaction. Five different ZSM-5 catalysts with different Si/Al ratio were obtained from their commercial sources (Table 16). Following the ion-exchange procedure described in the "Experimental Section" above, these ZSM-5 zeolites were converted into sodium form and ensured the full conversion by ICP analysis. FIG. 26 provides the efficacy of these zeolites with different Si/Al ratio in lactic acid conversion and selectivity for acrylic acid (AA), hydroxyl acetone (HydAce), acetaldehyde (AceAld), 2,3-pentadione (23P) and propionic acid (PropAc) in a lactic acid dehydration reaction. The data presented is an average of 4 hour on-stream for each experiment.

Example 17

TGA Profile of Fresh and Spent 3×Na Zeolite L

Figure 27:
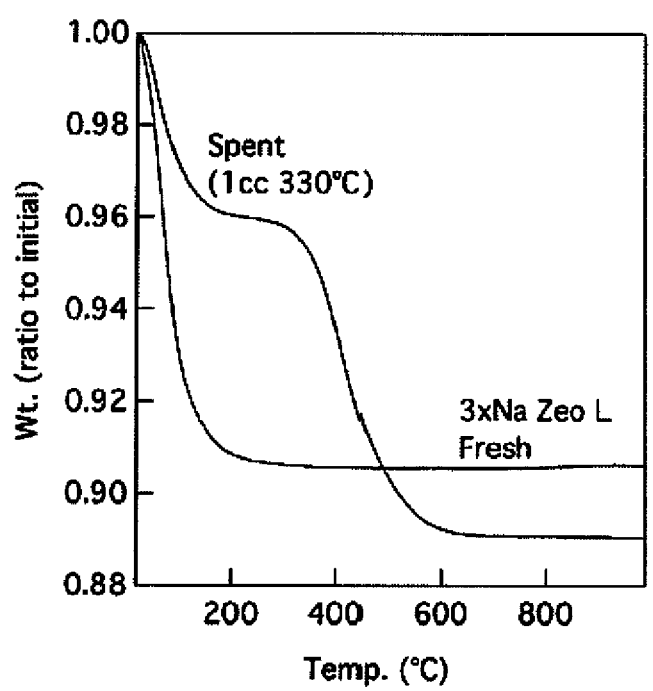
FIG. 27 TGA profile of fresh and spent 3×Na Zeolite L

TGA analysis was followed to quantify the carbonaceous deposition in zeolite catalyst after its use in a dehydration reactor for a specific period of time. Preliminary TGA analysis of fresh and spent 3×Na zeolite L samples was performed with TA Instruments TGA 2050. About 15 mg of samples was placed on a platinum pan and heated to 900° C. at the rate of 10° C. min under air. The results are shown in FIG. 27. The profile for the fresh sample indicates desorption of physisorbed on the surface at lower than 200° C. There is no mass loss after 200° C. For the spent 3×Na Zeolite L catalyst the weight loss profile is quite different than for the fresh sample. If one assumes the steady-state weight ratio represents the loss of carbon only, then we estimate that the weight of carbon is 18 11% of the initial catalyst weight. The actual mass of the deposit was then estimated to be 70.4 mg, which accounts for 3.8% of carbon fed during 4 h of reaction, assuming the deposit is pure carbon.

Figure 28:
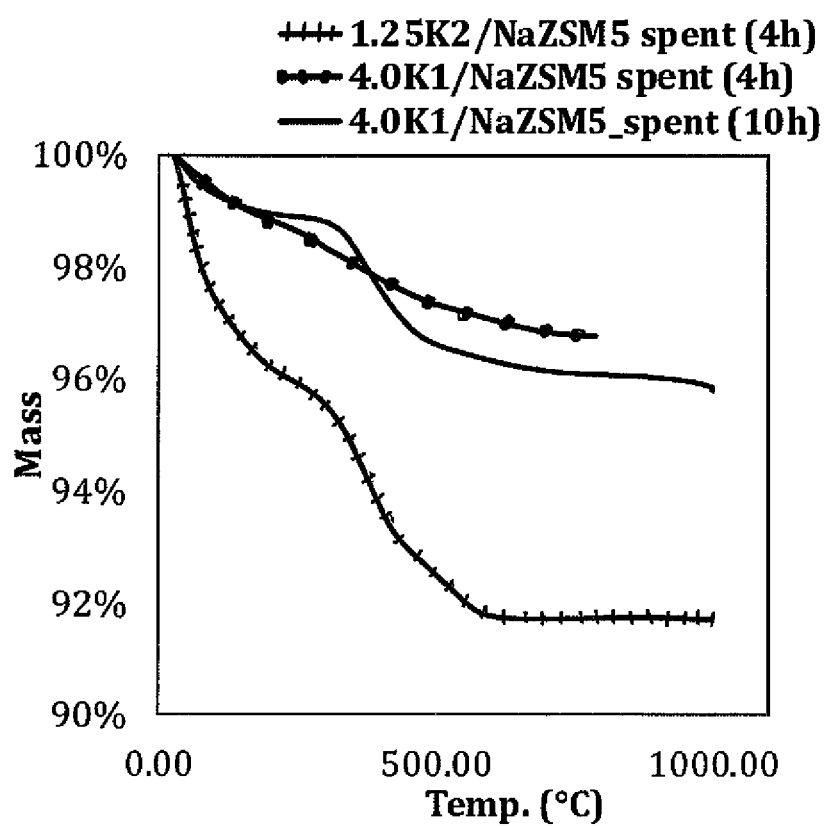
FIG. 28 TGA profile of fresh and spent 4.0K1/Na-ZSM-5 catalyst

TGA analysis of the fresh and spent catalysts 4.0 mmol KH2PO4/g-Na-ZSM-5 is provided in FIG. 28. It was found that spent 4.0 mmol KH2PO4/g-Na-ZSM-5catalyst contains carbon deposition (3.2 wt %; 32 mg/g-cat) which could roughly account for 4.8% of total carbon balance for each hour. The deposition after 10 hour run of 4.0 mmol KH2PO4/g-Na-ZSM-5catalyst was 4.2 wt %, only.

Example 18

Comparison of Support for 4 mmol $KH_2PO_4$

Figure 29:
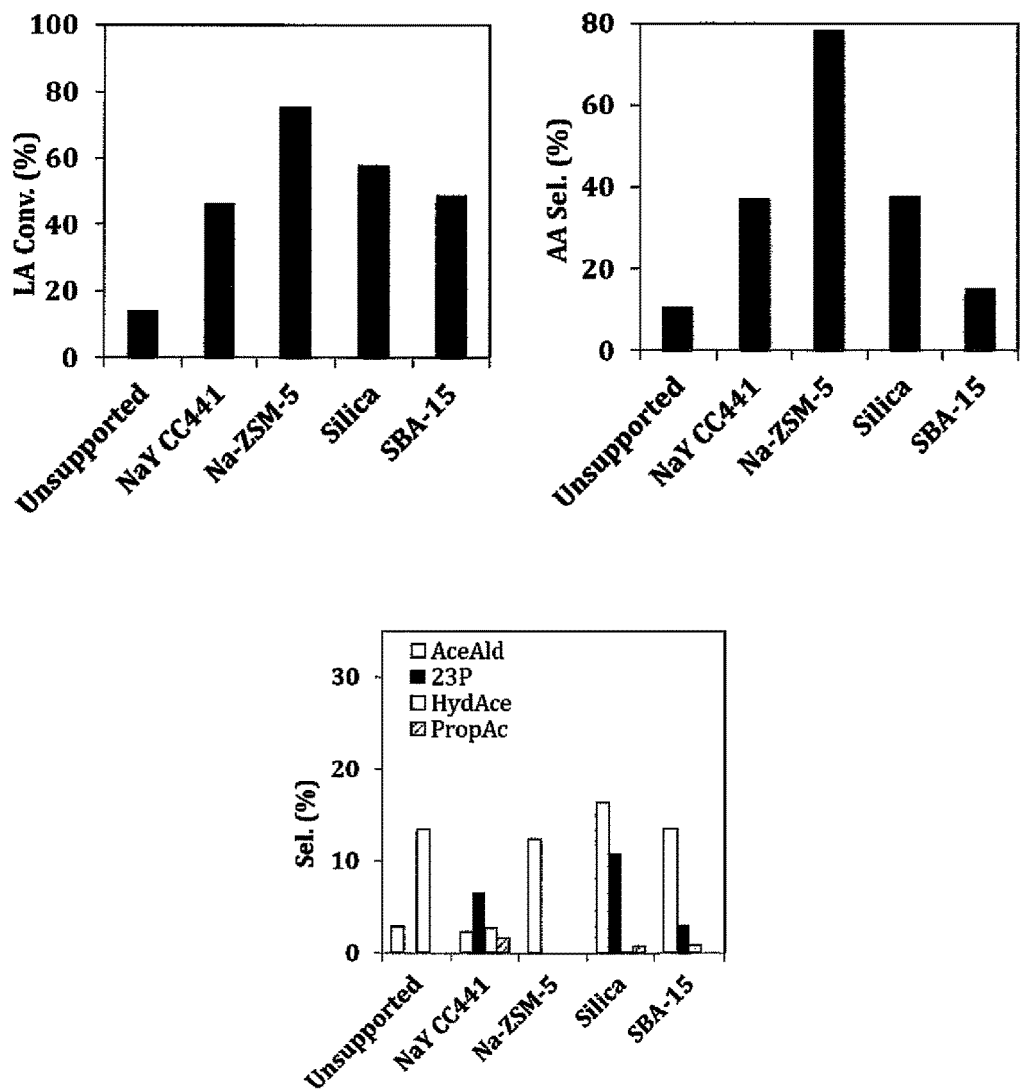
FIG. 29 Effect of support material for 4.0K1 loading on 4-h overall lactic acid conversion and normalized weight selectivity for acrylic acid and other side products acetaldehyde, 2,3-pentanedione. hydroxyl acetic acid and propionic acid.

In this experiment, silica gel (Sigma-Aldrich: 236810), a mesoporous silica (SBA-15), NaYCC441 zeolite and Na-ZSM-5 zeolite were assessed for their use as a support material. The incipient impregnation method was followed and the samples were calcined at 300° C. for 3 hours. The dehydration reaction was conducted using USP 20% LA feed solution at 330° C. for 4 hours. Conversion of lactic acid and normalized lactic acid selectivity for acrylic acid were determined as shown in FIG. 29

Example 19

Characterization of NaY441 and NaZSM5 Catalysts

Figure 30:
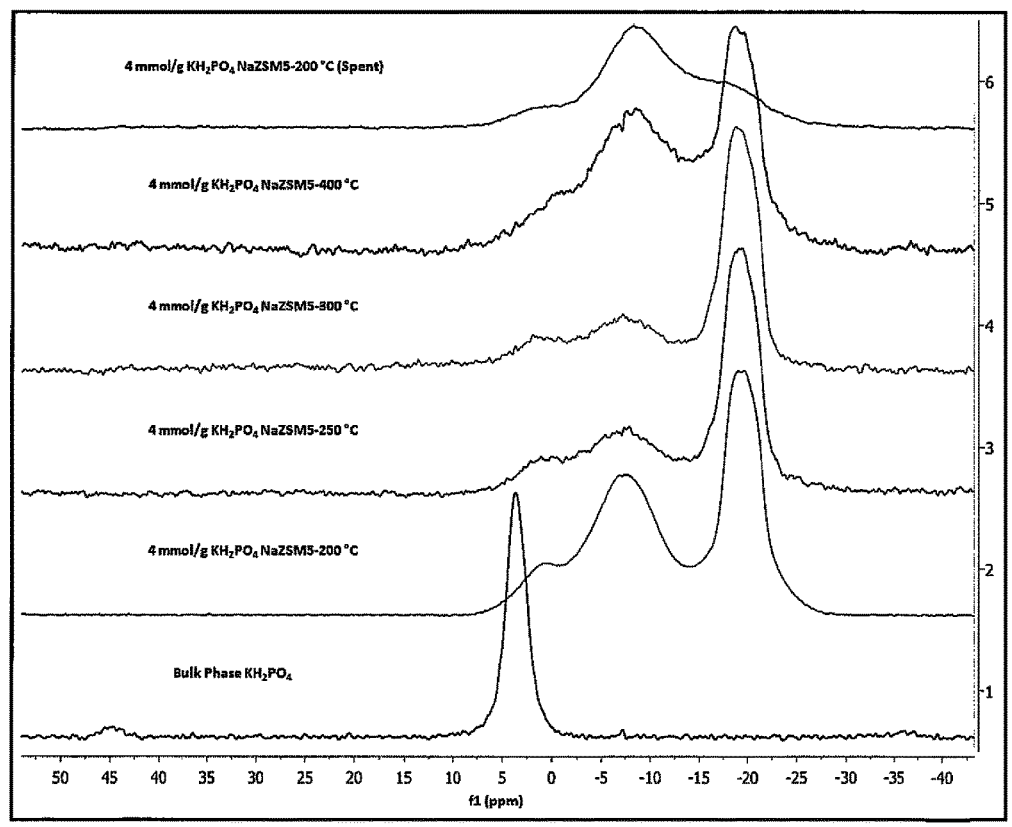
FIG. 30 $^{31}P$ Solid State NMR spectra for 4.0K1/Na-ZSM-5 catalysts calcined at different temperatures. Spent catalyst (4.0K1/NaZSM5) used in this experiment was calcined at 200° C. $^{31}P$ Solid State NMR spectrum of unsupported bulk $KH_2PO_4$ is also shown at the bottom of this figure.

FIG. 30 provides the $^{31}P$ solid state NMR spectra for 4.0mmKH$_2$PO$_4$/g-Na-ZSM-5 catalysts calcined at different temperatures and spent catalyst calcined at 200° C. $^{31}P$ NMR spectrum of unsupported bulk 4.0 mm $KH_2PO_4$ is also shown at the bottom of the FIG. 30.

The peak at ~1 ppm is associated with the excess phosphorus compound, which did not react with the framework aluminum which is the weakest peak in the supported samples. The peak at −7 ppm is due to the phosphorus atoms in pyrophosphoric acid (or on terminal [PO4]3—in polyphosphoric species). The peak at −7 pm decreases in intensity relative to the peak at −19 ppm when the calcination temperature is increased from 200° C. to 300° C., then increases at 400° C. and on the spent catalyst. The remaining broad resonance at −19 ppm contains signals of longer polymeric phosphate chains and extra framework aluminum phosphate as well as highly condensed polyphosphate species. This might be suggest that part of the Si—O—Al bonds in the tetrahedral coordinated framework Al species were broken such that phosphorus occupied the silicon sites to form the $(SiO)_x Al(PO)_{4-x}$ species.

Figure 31:
FIG. 31 Photographs of fresh and spent 1.0K2(pH13)/NaY441, 1.25K2/NaZSM5 and 4.0K1NaZSM5 catalysts are shown in the top row. 1.0K2(pH13)/NaY441 is NaY441 zeolite impregnated with 1 mmol of $K_2HPO_4$/g at pH 13. 1.25K2/NaZSM5 is NaZSM5 zeolite impregnated with 1.25 mmol of $K_2HPO_4$/g. 4.0K1NaZSM5 is NaZSM5 catalyst impregnated with 4.0 mmol of $KH_2PO_4$. In each pair, the fresh catalyst is on the left side and the spent catalyst is on the right side. Shown in the lower row are vials containing product solutions from the dehydration reaction catalyzed by 1.0K2(pH13)/NaY441, 1.25K2/NaZSM5 and 4.0K1ZSM5 catalysts. The reaction product from the dehydration catalyzed by 1.0K2(pH13)/NaY441 catalyst was slightly turbid and yellowish in color. The reaction products from the dehydration reaction catalyzed by 1.25K2/NaZSM5 and 4.0K1ZSM5 catalysts were clear colorless solutions.
Figure 31:
Figure 31:
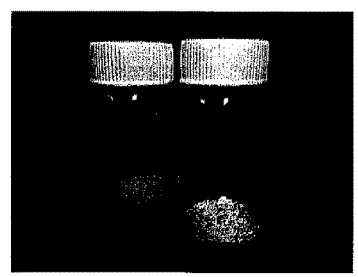
Figure 31:
Figure 31:
Figure 31:

FIG. 31 provides the picture of three different fresh and spent catalysts. In the case of NaY441 zeolite impregnated with 1.0 mmol $K_2HPO_4$/g, when compared to the fresh catalyst, the spent catalyst was slightly brown in color. In addition the product resulting from the vapor phase dehydration of lactic acid using NaY441 zeolite impregnated with 1.0 mmol K2HPO4/g was slightly turbid and yellow in color. In the case of NaZSM-5 zeolite impregnated with 1.25 mmol $K_2HPO_4$/g and NaZSM-5 zeolite impregnated with 4.0mmol$KH_2PO_4$/g, the spent catalyst maintained the original white color. In addition, products resulting from the vapor phase dehydration of lactic acid using NaZSM-5 zeolite impregnated with 1.25 mmol$K_2HPO_4$/g and NaZSM-5 zeolite impregnated with 4.0 mmol $KH_2PO_4$/g were clear and colorless in appearance.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

TABLE 1

| Formulae for estimating space velocity, conversion and selectivity | |
|---|---|
| Liquid Hourly Space Velocity ("LHSV") | $LHSV (mL/mL_C/h) = \dfrac{F_{lf}}{V_C}$ |
| Gas Hourly Gas Space Velocity ("GHSV") | $GHSV (mL/mL_C/h) = \dfrac{F_{gf}}{V_C}$ |
| Weight Hourly Space Velocity ("WHSV") | $WSHV (g_X/g_C/h) = \dfrac{G_X}{G_C * time}$ |
| Reactant Conversion ("Cnv$_X$") | $Cnv_X (\%) = \dfrac{[X]_{in} - [X]_{out}}{[X]_{in}} \times 100$ |
| Product Selectivity ("Sel$_Y$") | $Sel_Y (\%) = \dfrac{[Y]_{out}}{[X]_{in} - [X]_{out}} \times 100$ |
| Normalized Wt. selectivity (%) | Sel$_Y$ (%)/% theoritical maximum weight yield | where:

C denotes a catalyst;

mL$_c$ denotes volume of catalyst mL denotes volume of liquid

X denotes a reactant;

Y denotes a component of the product;

$F_{lf}$ is the liquid flow rate in mL/h;

$F_{gf}$ is the gas flow rate in mL/h;

$V_C$ is the volume of C in the reactor;

$G_X$ is the mass of X;

$G_C$ is the mass of C in the reactor;

$[X]_{in}$ is the molar concentrations of X in the starting composition;

$[X]_{out}$ is the molar concentrations of X in the exit flow; and $[Y]_{out}$ is the molar concentration of Y in the exit flow.

Please see the next page and incorporate the details about Normalized Wt. Sel.

TABLE 2

Zeolites used in the present study

| Catalyst Type | Silica/Alumina | Si/Al | Cation | Shape/Form | Supplier |
|---|---|---|---|---|---|
| Zeolite-Y, HiSiv-1000 | 4 | 7.0 | Hydrogen | Extrudates | UOP |
| Zeolite-NaY | 4-5 | | Sodium | Extrudates | WR Grace |
| Zeolite-KY | 4-5 | | Potassium | Extrudates | WR Grace |
| Zeolite-X | NA | | NA | Extrudates | Wako |
| Zeolite-L | 6.1 | 10.7 | Potassium | Extrudates | Tosoh |
| Zeolite-L, HSZ500KOD1C | 6.1 | 10.7 | Potassium | Extrudates | Tosoh |
| Zeolite-L, HSZ500KOD1C | 6.1 | 10.7 | Potassium | Extrudates | Tosoh |
| Zeolite-L, HSZ500KOA | 6.1 | 10.7 | Potassium | Powder | Tosoh |
| Zeolite-Y, 330HUD1A | 6 | 10.5 | Hydrogen | Extrudates | Tosoh |
| Zeolite-Y, 360HUD1C | 15 | 26.3 | Hydrogen | Extrudates | Tosoh |
| Mordenite, 640HOA1A | 18 | 31.6 | Hydrogen | Extrudates | Tosoh |
| Zeolite Beta, 920HOD1A | 18 | 31.6 | Hydrogen | Extrudates | Tosoh |
| Zeolite Beta, 930HOD1S | 27 | 47.4 | Hydrogen | Extrudates | Tosoh |
| zeolite-Y, CBV 100 | 5.1 | 8.9 | Sodium | Powder | Zeolyst |
| zeolite-Y, CBV 500 | 5.2 | 9.1 | $NH_4$ | Powder | Zeolyst |
| zeolite-Y, CBV 712 | 12 | 21.1 | $NH_4$ | Powder | Zeolyst |
| zeolite-beta, CP814E | 25 | 43.9 | $NH_4$ | Powder | Zeolyst |
| Amorphous silica-alumina, CC461 | 0.1 | 0.2 | None | Powder | Tricat |
| SAPO-34, CC436 | 0.5 | 0.9 | None | Powder | Tricat |
| ZSM-5-25, CC439 | 25 | 43.9 | Hydrogen | Powder | Tricat |
| NaY Zeolite, CC428 | 5.3 | 9.3 | Sodium | Powder | Tricat |
| NaY Zeolite, CC441 | 6.3 | 11.1 | Sodium | Powder | Tricat |
| K—X zeolite | | | | Powder | Tricat |
| Li—X zeolite | | | | Powder | Tricat |
| Na—X zeolite | | | | Powder | Tricat |
| Na-ZSM5 | 27 | 47.4 | Sodium | Powder | Tricat |
| Mesoporous NaY | | | Sodium | Powder | Yuriy Roman |

TABLE 3

Elemental analysis of selected commercial zeolites

| Zeolite t | Sodium (ppm) | Potassium (ppm) | Phosphorous (ppm) | Iron (ppm) | Calcium (ppm) | Magnesium (ppm) | $SiO_2/Al_2O_3$ |
|---|---|---|---|---|---|---|---|
| Zeolyst CBV 2314 | 23354 | 38 | n.d. | 45 | n.d. | n.d. | 23 |
| TRICAT NaZSM5 | 24342 | 223 | n.d. | 236 | 779 | 240 | 27 |
| Zeolyst CBV 5524G | 17814 | 45 | n.d. | 36 | n.d. | n.d. | 50 |
| Zeolyst CBV 8014 | 10879 | 70 | n.d. | n.d. | n.d. | n.d. | 80 |
| Zeolyst CBV 28014 | 3395 | 118 | n.d. | n.d. | n.d. | n.d. | 280 | n.d. = Not detected

TABLE 4

Elemental analysis of 341NHA and 3X Na-341NHA

| Catalyst | Element (mg/L) | | | | | |
|---|---|---|---|---|---|---|
| | Ca | Fe | K | Zn | Na | NH4 |
| 341NHA | 159 | 639 | 99 | 78 | 600 | 33318 |
| 3x Na-341NHA | 102 | 159 | 386 | 56 | 37070 | n.d |

TABLE 5

Quantified NH3-TPD over different K1 catalysts

| Sample | Sample amount (g) | Area Count | NH$_3$ [cm$^3$-STP] | NH$_3$ [cm$^3$-STP/g] | NH$_3$ [mmol/g] |
|---|---|---|---|---|---|
| NaYCC428 | 0.5039 | 3.10 | 6.59 | 13.1 | 0.58 |
| NaYCC441 | 0.5050 | 2.38 | 5.06 | 10.0 | 0.45 |
| 1.0 K2HPO4_NaY441 | 0.5107 | 0.10 | 0.21 | 0.4 | 0.02 |
| NaZSM5 | 0.2445 | 5.27 | 11.21 | 45.8 | 2.05 |
| 1.0 K2HPO4_NaZSM5 | 0.3790 | 2.27 | 4.82 | 12.7 | 0.57 |
| 1.0 K2HPO4_NaZSM5 | 0.4505 | 0.16 | 0.34 | 0.7 | 0.03 |
| 1.0 K2HPO4_NaY441_pH12 | 0.4640 | 0.05 | 0.11 | 0.2 | 0.01 |
| 2.0 K2HPO4_NaZSM5 | 0.3085 | 6.75 | 14.35 | 46.5 | 2.08 |
| 1.5 K2HPO4_NaZSM5 | 0.2999 | 1.58 | 3.36 | 11.2 | 0.50 |
| K2HPO4 bulk | 0.2957 | 0.00 | 0.00 | 0.00 | 0.00 |
| 2.0 K2HPO4_NaZSM5 | 0.3247 | 5/96 | 12.69 | 39.1 | 1.74 |
| 1xNa NaZSM | 0.3195 | 6.89 | 14.66 | 45.9 | 2.05 |
| 4.0 KI/NaZSM5 | 0.2918 | 0.45 | 0.96 | 3.3 | 0.15 |
| 4.0KI/NaZSM5 - pH 5 | 0.3228 | 0.65 | 1.38 | 4.3 | 0.19 |
| 4.0KI/NaZSM5 - pH 7 | 0.3237 | 0.63 | 1.34 | 4.1 | 0.18 |

TABLE 6

Surface area, relative acid quantity and SiO2/Al2O3 ratio for various zeolites

| Sample | Surface Area BET (m$^2$/g) | Relative Acid quantity* | SiO2/Al2O3 ratio |
|---|---|---|---|
| Zeolite - L | 279.6 | | |
| 3 x Na-Zeolite-L | 301.6 | | |
| 7.1 wt. % Na2HPO4-3xNa-Zeolite L | 61.9 | | |
| NaY - CC441 | 687.5 | 1 | 6.3 |
| 1.0 mmol/gm K$_2$HPO$_4$ on NaY (CC441), calcined at 450° C. | 330.0 | 0.04 | |
| 1.0 mmol/gm K$_2$HPO$_4$ on NaY (CC441), calcined at 450° C. - After 4 h reaction at 330° C. | 10.5 | | |
| NaY - CBV-10A | 310.2 | | |
| CBV-10A - 0.5 mmol/g K$_2$HPO$_4$ loaded | 33.2 | | |
| CBV-10A - 1.0 mmol/g K$_2$HPO$_4$ loaded | 19.3 | | |
| HC-1295 | 610.5 | 0.92 | 10.8 |
| HC1295 - K$_2$HPO$_4$ loaded | 404.9 | 0.05 | |
| HC1296 | 587.3 | 0.36 | 23.2 |
| HC1296 - K$_2$HPO$_4$ loaded | 436.9 | 0.07 | |
| Na-ZSM-5 | 290.4 | | |
| Na-ZSM-5 1.0 mmol/g K$_2$HPO$_4$ Na-ZSM-5 | 222.7 | | |
| Na-ZSM-5 1.5 mmol/g K$_2$HPO$_4$ Na-ZSM-5 | 191.1 | | |
| Na-ZSM-5 2.0 mmol/g KH$_2$PO$_4$ Na-ZSM-5 | 152.2 | | |
| Na-ZSM-5 4.0 mmol/g KH$_2$PO$_4$ Na-ZSM-5 | 115.2 | | |
| Na-ZSM-5 4.0 mmol/g KH$_2$PO$_4$ Na-ZSM-5 | 6.9 | | |

*Relative acid quantity, determined form the TPD profiles (normalized with NaY CC441 taking to the unity.

TABLE 7

Effect of alkali salt impregnation of ZSM5 zeolite on the dehydration reaction

| Impregnation composition | Time (hr) | Mass Recovery (%) | Conversion of Lactic Acid (%) | Selectivity (%) | | | | |
|---|---|---|---|---|---|---|---|---|
| | | | | AceAld | 23P | HyAce | PropA | AA |
| 2 mmol/g K1: K$_2$HPO$_4$ | 1 | 94.3 | 87.6 | 21.1 | 0.0 | 0.0 | 0.0 | 60.8 |
| | 2 | 91.5 | 89.8 | 20.3 | 0.0 | 0.0 | 0.0 | 56.6 |
| | 3 | 91.6 | 92.0 | 20.0 | 0.0 | 0.0 | 0.0 | 53.2 |
| | 4 | 94.0 | 91.8 | 20.5 | 0.0 | 0.0 | 0.0 | 54.1 |
| | Overall | 92.9 | 90.3 | 20.5 | 0.0 | 0.0 | 0.0 | 56.1 |
| 2 mmol/g K2: K$_2$HPO$_4$ | 1 | 95.1 | 88.9 | 9.1 | 6.0 | 1.1 | 5.4 | 54.0 |
| | 2 | 95.4 | 91.2 | 9.8 | 6.7 | 1.3 | 6.4 | 53.3 |
| | 3 | 95.9 | 93.2 | 9.3 | 6.4 | 1.4 | 7.9 | 49.6 |
| | 4 | 100.9 | 92.3 | 8.3 | 5.8 | 1.4 | 10.3 | 47.6 |
| | Overall | 96.8 | 91.4 | 9.1 | 6.2 | 1.3 | 7.5 | 51.1 |

TABLE 7-continued

Effect of alkali salt impregnation of ZSM5 zeolite on the dehydration reaction

| Impregnation composition | Time (hr) | Mass Recovery (%) | Conversion of Lactic Acid (%) | Selectivity (%) | | | | |
|---|---|---|---|---|---|---|---|---|
| | | | | AceAld | 23P | HyAce | PropA | AA |
| 1 mmol/g K3: K$_3$PO$_4$ | 1 | 94.4 | 94.4 | 8.8 | 7.6 | 0.8 | 3.6 | 45.8 |
| | 2 | 94.5 | 94.5 | 9.6 | 8.0 | 0.6 | 3.9 | 48.6 |
| | 3 | 93.4 | 93.4 | 10.2 | 7.8 | 0.5 | 4.1 | 48.1 |
| | 4 | 101.7 | 101.7 | 11.1 | 7.8 | 0.0 | 4.6 | 51.3 |
| | Overall | 96.0 | 96.0 | 9.9 | 7.8 | 0.5 | 4.1 | 48.4 |
| 1 mmol/g K4: K$_4$P$_2$O$_7$ | 1 | 96.1 | 84.7 | 16.7 | 3.1 | 0.5 | 1.5 | 39.3 |
| | 2 | 91.2 | 85.0 | 16.0 | 3.5 | 0.7 | 1.7 | 38.9 |
| | 3 | 03.1 | 80.7 | 15.0 | 4.2 | 0.9 | 1.9 | 42.9 |
| | 4 | 96.2 | 77.2 | 17.8 | 5.2 | 1.3 | 2.2 | 45.7 |
| | Overall | 94.1 | 81.9 | 16.3 | 4.0 | 0.8 | 1.8 | 41.6 |
| 1 mmol/g K5: K$_5$P$_3$O$_{10}$ | 1 | 96.6 | 88.8 | 10.8 | 1.2 | 0.0 | 3.0 | 60.8 |
| | 2 | 95.6 | 79.0 | 8.7 | 3.7 | 0.0 | 2.5 | 54.1 |
| | 3 | 94.8 | 71.4 | 8.8 | 4.5 | 0.0 | 2.3 | 53.8 |
| | 4 | 98.9 | 65.7 | 10.8 | 6.1 | 0.0 | 2.9 | 63.0 |
| | Overall | 96.5 | 76.2 | 9.8 | 3.7 | 0.0 | 2.7 | 57.9 |

TABLE 8

Effect of alkali phosphate loading on the vapor phase lactic dehydration reaction catalyzed by modified NaZSM-5 zeolites

| Catalyst | Time (h) | Mass Recovery | Conversion of lactic acid | Selectivity (%) | | | | |
|---|---|---|---|---|---|---|---|---|
| | | | | AceAld | 23P | HyAce | PropA | AA |
| NaZMS-5 Unmodified | 1 | 93.0 | 89.3 | 24.7 | 0/0 | 0.0 | 0.2 | 36. |
| | 2 | 93.4 | 88.6 | 28.3 | 0.0 | 0.0 | 0.3 | 41.3 |
| | 3 | 90.2 | 79.3 | 30.7 | 0.0 | 0.0 | 0.5 | 46.7 |
| | 4 | 96.2 | 68.1 | 25.5 | 0.0 | 0.0 | 0.4 | 49.1 |
| | Overall | 93.2 | 81.3 | 27.3 | 0.0 | 0.0 | 0.4 | 42.8 |
| NaZMS-5 KH$_2$PO4 2 mmol/g | 1 | 94.3 | 87.6 | 21.1 | 0.0 | 0l.0 | 0.0 | 60.8 |
| | 2 | 91.5 | 89.8 | 20.3 | 0.0 | 0.0 | 0.0 | 56.6 |
| | 3 | 91.6 | 92.0 | 20.0 | 0.0 | 0.0 | 0.0 | 53.2 |
| | 4 | 94.0 | 91.8 | 20.5 | 0.0 | 0.0 | 0.0 | 54.1 |
| | Overall | 92.9 | 90.3 | 20.5 | 0.0 | 0.0 | 0.0 | 56.1 |
| NaZMS-5 KH$_2$PO4 3 mmol/g | 1 | 92.6 | 83.8 | 16.9 | 0.0 | 0.0 | 0.3 | 67.0 |
| | 2 | 90.6 | 85.2 | 19.5 | 0.4 | 0.0 | 0.0 | 61.8 |
| | 3 | 92.3 | 85.2 | 20.2 | 0.0 | 0.0 | 0.0 | 61.0 |
| | 4 | 96.3 | 80.7 | 18.8 | 0.6 | 0.0 | 0.0 | 68.6 |
| | Overall | 93.0 | 83.7 | 18.8 | 0.2 | 0.0 | 0.1 | 64.5 |
| NaZMS-5 KH$_2$PO4 4 mmol/g | 1 | 96.5 | 97.8 | 11.7 | 0.0 | 0.0 | 0.0 | 81.0 |
| | 2 | 96.3 | 98.2 | 11.8 | 0.0 | 0.0 | 0.0 | 85.9 |
| | 3 | 95.7 | 98.1 | 12.0 | 0.0 | 0.0 | 0.0 | 82.8 |
| | 4 | 101.6 | 98.1 | 11.7 | 0.0 | 0.0 | 0.0 | 92.7 |
| | Overall | 97.5 | 98.0 | 11.8 | 0.0 | 0.0 | 0.0 | 85.6 |
| NaZMS-5 KH$_2$PO4 5 mmol/g | 1 | 94.7 | 96.0 | 14.7 | 0.9 | 0.0 | 0.4 | 74.1 |
| | 2 | 96.1 | 93.2 | 14.4 | 1.4 | 0.0 | 0.4 | 69.4 |
| | 3 | 97.0 | 91.2 | 13.6 | 1.7 | 0.0 | 0.9 | 68.2 |
| | 4 | 101.3 | 88.2 | 12.8 | 1.9 | 0.0 | 1.7 | 67.4 |
| | Overall | 97.3 | 92.2 | 13.9 | 1.5 | 0.0 | 0.8 | 69.8 |
| NaZMS-5 KH$_2$PO4 6 mmol/g | 1 | 93.7 | 79.2 | 15.8 | 0.0 | 0.0 | 0.0 | 58.2 |
| | | 95.4 | 66.7 | 220.6 | 0.0 | 0.0 | 0.0 | 53.5 |
| | 3 | 94.9 | 64.6 | 27.0 | 0.0 | 0.0 | 0.3 | 43.5 |
| | 4 | 98.3 | 63.2 | 25.9 | 0.0 | 0.0 | 0.4 | 411.9 |
| | Overall | 95.6 | 678.4 | 22.0 | 0.0 | 0.0 | 0.2 | 49.8 |

TABLE 9

Effect of feed concentration on the dehydration of lactic acid using modified NaZSM-5 catalyst..

| Feed Conc. (w/v) | Time (hr) | Mass Recovery (%) | Lactic acid conversion (%) | Selectivity (%) | | | | |
|---|---|---|---|---|---|---|---|---|
| | | | | Acetic Acid | 2,3-Pentanediol | Hydroxy Acetone | Propionic acid | Acrylic acid |
| 25% | 1 | 94.4 | 96.3 | 15.3 | 0.3 | 0.0 | 0.0 | 78.2 |
| | 2 | 93.0 | 94.9 | 15.7 | 0.4 | 0.0 | 0.0 | 80.5 |

TABLE 9-continued

Effect of feed concentration on the dehydration of lactic acid using modified NaZSM-5 catalyst..

| Feed Conc. (w/v) | Time (hr) | Mass Recovery (%) | Lactic acid conversion (%) | Selectivity (%) | | | | |
|---|---|---|---|---|---|---|---|---|
| | | | | Acetic Acid | 2,3-Pentanediol | Hydroxy Acetone | Propionic acid | Acrylic acid |
| | 3 | 94.9 | 93.6 | 15.5 | 0.5 | 0.0 | 0.0 | 83.5 |
| | 4 | 98.6 | 92.1 | 14.4 | 0.6 | 0.0 | 0.0 | 86.3 |
| | Overall | 95.2 | 94.2 | 15.2 | 0.4 | 0.0 | 0.0 | 82.1 |
| 20% | 1 | 93.2 | 85.6 | 13.7 | 0.0 | 0.0 | 0.0 | 73.0 |
| | 2 | 95.6 | 82.1 | 15.5 | 0.0 | 0.0 | 0.0 | 76.8 |
| | 3 | 95.5 | 82.1 | 18.4 | 0.0 | 0.0 | 0.0 | 82.6 |
| | 4 | 10.2.0 | 8.0.8 | 14.5 | 0.0 | 0.0 | 0.0 | 81.8 |
| | Overall | 96.6 | 82.6 | 15.5 | 0.0 | 0.0 | 0.0 | 78.5 |
| 15% | 1 | 93.8 | 94.5 | 9.0 | 0.0 | 0.0 | 0.0 | 71.0 |
| | 2 | 93.9 | 92.3 | 8.7 | 0.0 | 0.0 | 0.0 | 75.3 |
| | 3 | 94.1 | 92.6 | 8.7 | 0.0 | 0.0 | 0.0 | 75.2 |
| | 4 | 98.1 | 91.1 | 8.1 | 0.0 | 0.0 | 0.0 | 79.8 |
| | Overall | 95.0 | 92.6 | 8.6 | 0.0 | 0.0 | 0.0 | 75.3 |

TABLE 10

Effect of temperature on the dehydration reaction catalyzed by modified NaZSM5 catalyst

| Reaction Temperature | Time | Mass Recovery (%) | Conversion of Lactic Acid (%) | Selectivity (%) | | | | |
|---|---|---|---|---|---|---|---|---|
| | | | | AceAld | 23P | HyAce | PropA | AA |
| 310° C. | 1 | 92.5 | 62.3 | 27.6 | 0.0 | 0.0 | 1.1 | 50.7 |
| | 2 | 95.1 | 58.4 | 29.6 | 0.0 | 0.0 | 0.8 | 48.2 |
| | 2 | 96.0 | 54.5 | 25.5 | 0.7 | 0.0 | 1.0 | 51.8 |
| | 4 | 102.9 | 45.1 | 25.8 | 0.7 | 0.0 | 1.2 | 63.1 |
| | Overall | 96.6 | 54.6 | 27.4 | 0.4 | 0.0 | 1.0 | 53.2 |
| 320° C. | 1 | 97.5 | 67.2 | 17.0 | 0.7 | 0.0 | 0.6 | 68.2 |
| | 2 | 96.7 | 65.3 | 19.7 | 0.7 | 0.0 | 0.5 | 61.6 |
| | 3 | 97.6 | 64.1 | 20.0 | 0.9 | 0.0 | 0.5 | 61.9 |
| | 4 | 103.2 | 64.7 | 24.2 | 1.0 | 0.0 | 0.6 | 60.3 |
| | Overall | 98.8 | 65.3 | 20.2 | 0.8 | 0.0 | 0.6 | 63.0 |
| 330° C. | 1 | 95.0 | 70.2 | 12.9 | 0.0 | 0.0 | 0.0 | 70.3 |
| | 2 | 97.1 | 66.7 | 14.4 | 0.0 | 0.0 | 0.4 | 74.5 |
| | 3 | 96.1 | 63.7 | 14.7 | 0.0 | 0.0 | 0.0 | 74.0 |
| | 4 | 101.2 | 62.3 | 14.5 | 0.0 | 0.0 | 0.0 | 79.4 |
| | Overall | 97.3 | 65.8 | 14.1 | 0.0 | 0.0 | 0.1 | 74.4 |
| 340° C. | 1 | 92.8 | 96.3 | 1.5 | 1.3 | 0.0 | 0.4 | 61.9 |
| | 2 | 95.3 | 93.7 | 14.7 | 2.0 | 0.0 | 0.7 | 64.4 |
| | 3 | 94.9 | 91.0 | 14.0 | 2.4 | 0.0 | 0.7 | 62.3 |
| | 4 | 99.6 | 87.8 | 13.7 | 2.9 | 0.0 | 1.1 | 64.1 |
| | Overall | 95.7 | 92.2 | 14.3 | 21.1 | 0.0 | 0.7 | 63.2 |
| 350° C. | 1 | 94.7 | 91.6 | 22.1 | 0.6 | 0.0 | 0.3 | 56.2 |
| | 2 | 93.3 | 89.5 | 20.7 | 0.9 | 0.0 | 0.3 | 58.0 |
| | 3 | 93.0 | 87.7 | 19.2 | 1.1 | 0.0 | 0.4 | 60.8 |
| | 4 | 71.5 | 88.6 | 14.3 | 1.1 | 0.0 | 0.3 | 46.2 |
| | Overall | 88.1 | 89.3 | 19.1 | 0.9 | 0.0 | 0.3 | 55.3 |

TABLE 11

Effect of carrier gas flow rate on the dehydration reaction catalyzed by ZSM5 catalyst

| Carrier gas flow rate | Time (hr) | Mass Recovery (%) | Conversion of lactic acid (%) | Selectivity (%) | | | | |
|---|---|---|---|---|---|---|---|---|
| | | | | AceAld | 23P | HyAce | PropA | AA |
| 25 cc/min He | 1 | 95.4 | 88.2 | 16.3 | 0 | 0 | 0.4 | 70.5 |
| | 2 | 94 | 86.5 | 16.7 | 0.4 | 0 | 0.4 | 66.3 |
| | 3 | 95 | 83.3 | 18.9 | 0.6 | 0 | 0.4 | 67.7 |
| | 4 | 99.1 | 82.8 | 19.6 | 0.7 | 0 | 0.7 | 69.7 |
| | Overall | 95.9 | 85.2 | 17.9 | 0.4 | 0 | 0.5 | 68.6 |
| 55 cc/min He | 1 | 93.1 | 83.2 | 9.04 | 0 | 0 | 0 | 68.7 |
| | 2 | 95.3 | 75.9 | 10.5 | 0 | 0 | 0 | 76.8 |
| | 3 | 95.3 | 75.2 | 11.2 | 0 | 0 | 0 | 77.6 |

TABLE 11-continued

Effect of carrier gas flow rate on the dehydration reaction catalyzed by ZSM5 catalyst

| Carrier gas flow rate | Time (hr) | Mass Recovery (%) | Conversion of lactic acid (%) | Selectivity (%) | | | | |
|---|---|---|---|---|---|---|---|---|
| | | | | AceAld | 23P | HyAce | PropA | AA |
| | 4 | 101.8 | 71.7 | 12.3 | 0 | 0 | 0 | 86.4 |
| | Overall | 96.4 | 76.3 | 10.8 | 0 | 0 | 0 | 77.3 |
| 110 cc/min He | 1 | 95.3 | 69.3 | 10.4 | 0 | 0 | 0.4 | 62.8 |
| | 2 | 97.1 | 62.1 | 12.4 | 0 | 0.5 | 0.4 | 67.4 |
| | 3 | 98.1 | 56.2 | 12.6 | 0 | 0.7 | 0.4 | 77.3 |
| | 4 | 102.2 | 54.8 | 14 | 0 | 0.6 | 0 | 79.7 |
| | Overall | 98.2 | 60.6 | 12.2 | 0 | 0.4 | 0.3 | 71.2 |
| 165 cc/min He | 1 | 96.3 | 98.1 | 12 | 0.3 | 0 | 0 | 69 |
| | 2 | 93.4 | 98.5 | 16.4 | 0.3 | 0 | 0 | 51.9 |
| | 3 | 92.1 | 98.8 | 17 | 0.3 | 0 | 0 | 46.4 |
| | 4 | 94.5 | 98.4 | 13.3 | 0.4 | 0 | 0 | 45.3 |
| | Overall | 94.1 | 98.5 | 14.7 | 0.3 | 0 | 0 | 53.1 |

TABLE 12

Effect of carrier gas type on the dehydration reaction catalyzed by ZSM5 catalyst

| Carrier Gas Type | Time (hr) | Mass Recovery (%) | Conversion of Lactic Acid (%) | Selectivity (%) | | | | |
|---|---|---|---|---|---|---|---|---|
| | | | | AccAld | 23P | HyAce | PropA | AA |
| 10% CO in He | 1 | 96.9 | 99.4 | 14.0 | 0.5 | 0.0 | 0.0 | 79.9 |
| | 2 | 97.3 | 99.3 | 14.2 | 0.6 | 0.0 | 0.0 | 80.5 |
| | 3 | 94.7 | 99.2 | 13.9 | 0.6 | 0.0 | 0.0 | 78.2 |
| | 4 | 103.8 | 99.0 | 13.3 | 0.7 | 0.0 | 0.0 | 85.3 |
| | Overall | 98.1 | 99.2 | 13.9 | 0.6 | 0.0 | 0.0 | 80.9 |
| $CO_2$ | 1 | 93.2 | 93.7 | 14.2 | 0.0 | 0.0 | 0.0 | 76.7 |
| | 2 | 93.2 | 93.2 | 15.5 | 0.0 | 0.0 | 0.0 | 79.0 |
| | 3 | 94.5 | 93.4 | 16.6 | 0.0 | 0.0 | 0.0 | 80.3 |
| | 4 | 99.2 | 92.9 | 16.5 | 0.0 | 0.0 | 0.0 | 82.7 |
| | Overall | 95.0 | 93.3 | 15.7 | 0.0 | 0.0 | 0.0 | 79.7 |
| $N_2$ | 1 | 96.6 | 86.0 | 12.2 | 0.0 | 0.0 | 0.0 | 67.9 |
| | 2 | 95.6 | 79.8 | 13.5 | 0.0 | 0.0 | 0.0 | 73.5 |
| | 3 | 95.5 | 77.3 | 14.3 | 0.0 | 0.0 | 0.0 | 71.7 |
| | 4 | 103.9 | 74.3 | 15.1 | 0.0 | 0.0 | 0.0 | 78.5 |
| | Overall | 97.9 | 79.4 | 13.7 | 0.0 | 0.0 | 0.0 | 72.7 |
| He | 1 | 92.0 | 95.2 | 11.3 | 0.0 | 0.0 | 0.0 | 74.9 |
| | 2 | 94.0 | 94.0 | 11.6 | 0.0 | 0.0 | 0.0 | 82.3 |
| | 3 | 94.5 | 93.1 | 12.2 | 0.0 | 0.0 | 0.0 | 81.7 |
| | 4 | 97.2 | 92.1 | 12.1 | 0.0 | 0.0 | 0.0 | 84.6 |
| | Overall | 94.6 | 93.6 | 11.8 | 0.0 | 0.0 | 0.0 | 80.8 |

TABLE 13

Effect of calcination temperature for 4.0K1/Na-ZSM-5 on lactic acid conversion, mass recovery, and selectivity for individual product in a dehydration reaction at 330° C. LA: Lactic acid; AceAld: acetaldehyde; 23P: 2-3pentanedione; HyAce: hydroxyl acetic acid; PropA: Propionic acid; AA: Acrylic acid

| Calcination Temperature | Time | Mass Recovery (%) | Conversion of Lactic Acid | Selectivity (%) | | | | |
|---|---|---|---|---|---|---|---|---|
| | | | | AceAld | 23P | HyAce | PropA | AA |
| 100° C. | 4 hr | 93.5 | 83.0 | 22.1 | 0.0 | 0.0 | 0.0 | 50.0 |
| 150° C. | 4 hr | 92.0 | 76.3 | 19.5 | 0.0 | 0.0 | 0.0 | 41.6 |
| 175° C. | 4 hr | 95.7 | 94.1 | 10.3 | 0.0 | 0.0 | 0.0 | 82.2 |
| 200° C. | 4 hr | 98.5 | 55.6 | 12.7 | 0.0 | 0.0 | 0.0 | 81.7 |
| 225° C. | 4 hr | 95.9 | 87.6 | 12.0 | 0.0 | 0.0 | 0.0 | 80.2 |
| 250° C. | 4 hr | 98.1 | 68.0 | 13.1 | 0.0 | 0.0 | 0.0 | 75.6 |
| 300° C. | 4 hr | | | | | | | |
| 400° C. | 4 hr | 96.8 | 66.1 | 13.1 | 0.0 | 0.0 | 0.0 | 74.7 |

TABLE 13-continued

Effect of calcination temperature for 4.0K1/Na-ZSM-5 on lactic acid conversion, mass recovery, and selectivity for individual product in a dehydration reaction at 330° C. LA: Lactic acid; AceAld: acetaldehyde; 23P: 2-3pentanedione; HyAce: hydroxyl acetic acid; PropA: Propionic acid; AA: Acrylic acid

| Calcination Temperature | Time | Mass Recovery (%) | Conversion of Lactic Acid | Selectivity (%) | | | | |
|---|---|---|---|---|---|---|---|---|
| | | | | AceAld | 23P | HyAce | PropA | AA |
| 500° C. | 4 hr | 96.5 | 55.4 | 18.1 | 0.9 | 0.8 | 0.0 | 55.6 |
| 600° C. | 4 hr | 98.6 | 46.0 | 1.7 | 1.7 | 0.6 | 0.6 | 68.1 |

Samples were analyzed at 1 hr, 2nr, 3 hr and 4 hr and the values provided is an average of all four values for each sample.

TABLE 14

Phosphorus elemental analysis of effluent solution from the dehydration reaction over 4.0 K1/Na-ZMS-5 zeolite

| Sample | P [mg/L] | P [mmol] | P ratio to catalyst |
|---|---|---|---|
| 0 hour | n.d | — | — |
| Run# 1 - 1 hour | 0.21 | $4.61 \times 10^5$ | 0.001% |
| Run# 1 - 2 hour | n.d | — | — |
| Run# 1 - 3 hour | n.d | — | — |
| Run# 1 - 4 hour | 0.10 | $2.29 \times 10^5$ | 0.001% |
| Run# 2 - 1 hour | 0.29 | $6.50 \times 10^5$ | 0.002% |
| Run# 2 - 2 hour | 0.21 | $4.73 \times 10^5$ | 0.001% |
| Run# 2 - 3 hour | 0.23 | $5.23 \times 10^5$ | 0.001% |
| Run# 2 - 4 hour | n.d | — | — |

TABLE 15

Conversion of lactic acid and normalized weight selectivity of major product for 4.0K1/3x Na NH4CZP27 catalysts. LA: lActic acid; AceAld: acetaldehyde; 23P 2,3-Pentanedione; HyAce: hydroxyacetone; PropA: propionic acid; AA: acrylic aid

| Catalyst | Time | Mass Recovery (%) | Conversion of LA (%) | Selectivity (%) | | | | |
|---|---|---|---|---|---|---|---|---|
| | | | | AceAld | 23P | HyAce | PropA | AA |
| 4.0K1 | 1 | 95.1 | 94.1 | 14.8 | 0.0 | 0.0 | 0.0 | 70.5 |
| 3xNa | 2 | 94.6 | 93.9 | 16.3 | 0.0 | 0.0 | 0.0 | 72.4 |
| NH4CZp27 | 3 | 91.6 | 94.3 | 18.0 | 0.0 | 0.0 | 0.0 | 71.9 |
| | 4 | 100.0 | 94.2 | 18.6 | 0.0 | 0.0 | 0.0 | 76.7 |
| | Overall | 95.3 | 94.1 | 16.9 | 0.0 | 0.0 | 0.0 | 72.9 |

TABLE 16

Elemental analysis of five different ZSM-5 zeolites

| Zeolite/Supplier | Element (ppm) | | | | | | $SiO_2/Al_2O_3$ |
|---|---|---|---|---|---|---|---|
| | Na | K | P | Fe | Ca | Mg | |
| NaZSM/Zeolyst | 23354 | 38 | n.d. | 45 | n.d | n.d. | 23 |
| NaZSM/TRICAT | 24342 | 223 | n.d. | 236 | 779 | 240 | 27 |
| NaZSM/Zeolyst | 17814 | 45 | n.d. | 36 | n.d. | n.d. | 50 |
| NaZSM/Zeolyst | 10879 | 70 | n.d. | n.d. | n.d. | n.d. | 80 |
| NaZSM/Zeolyst | 3395 | 118 | n.d. | n.d. | n.d. | n.d. | 280 |

REFERENCES

All references are listed for the convenience of the reader. Each reference is incorporated by reference in its entirety.
U.S. Pat. No. Re. 29,857
U.S. Pat. No. 2,183,357
U.S. Pat. No. 2,464,364
U.S. Pat. No. 2,859,240
U.S. Pat. No. 2,881,205
U.S. Pat. No. 2,882,243
U.S. Pat. No. 2,882,244
U.S. Pat. No. 2,962,525
U.S. Pat. No. 3,012,853
U.S. Pat. No. 3,022,336
U.S. Pat. No. 3,087,962
U.S. Pat. No. 3,130,007
U.S. Pat. No. 3,702,886
U.S. Pat. No. 4,631,264
U.S. Pat. No. 4,657,749
U.S. Pat. No. 4,729,978
U.S. Pat. No. 4,786,756
U.S. Pat. No. 4,995,963
U.S. Pat. No. 5,068,399
U.S. Pat. No. 5,071,754
U.S. Pat. No. 5,250,729
U.S. Pat. No. 5,252,473
U.S. Pat. No. 5,268,506
U.S. Pat. No. 5,294,579
U.S. Pat. No. 5,371,273

U.S. Pat. No. 6,096,936
U.S. Pat. No. 6,545,175
U.S. Pat. No. 6,992,209
U.S. Pat. No. 7,238,636
U.S. Pat. No. 7,538,247
U.S. Pat. No. 7,629,162
U.S. Pat. No. 7,687,661
U.S. Pat. No. 7,696,375
U.S. Pat. No. 7,851,188
U.S. Pat. No. 7,910,342
U.S. Pat. No. 7,993,889
U.S. Pat. No. 9,012,686
U.S. Patent Application Publication No. US20040158113
U.S. Patent Application Publication No. US2010195505
U.S. Patent Application Publication No. US20100129886
U.S. Patent Application Publication No. US20100221801
U.S. Patent Application Publication No. US20100062505
U.S. Patent Application Publication No. US20110183392
U.S. Patent Application Publication No. US20110159558
U.S. Patent Application Publication No. US20110195505
U.S. Patent Application Publication No. US 20110112334
European Patent Application Publication No. 0,614,983 A2
Patent Abstracts of Japan Publication No. 2003-284580
Patent Abstracts of Japan Publication No. 2004-315411
International Patent Application Publication No. WO/2011/040700

Aida, T. K., Ikarashi, A., Saito, Y., Watanabe, M., Smith Jr., R. L., and Arai, K. (2009) *J. Supercritical Fluids* 50: 257-264.

Alvarez, M. E. T., Moraes, E. B., Machado, A. B., Filho, R. M., Wolf-Maciel, M. R. (2007) Evaluation of liquid-liquid extraction process for separating acrylic acid produced from renewable sugars. *App. Biochem. Biotech.* 136-140: 451-462.

Danner, H., Urmos, M., Gartner, M., and Braun, R. (1998) Biotechnological production of acrylic acid from biomass. *App. Biochem. Biotechnol.* 70-72: 887-894.

Fan, Y., Zhou, C., and Zhu, X. (2009) Selective catalysis of lactic acid to produce commodity chemicals. *Catalysis Review* 51(3): 293-324)

Glauser, J., Blagoev, M., and Kumamoto, T. (2011) CEH Marketing Research Report. Acrylic acid, acrylate esters and superabsorbent polymers.

Gunter, G. C., Langford, R. H., Jackson, J. E., Miller, D. J. (1995) Catalysts and supports for conversion of alctic acid to acrylic acid and 2,3-pentanedione. *Ind. Eng. Chem. Res.* 34: 974-980.

Iizuka, T., Fujie, S., Ushikubo, T., Chen, Z-h., Tanabe, K. (1986) Esterification of acrylic acid with methanol over niobic acid catalyst. *App. Catal.* 28: 1-5.

Jiang, X., Meng, X. and Xian, M. (2009) Biosynthetic pathway for 3-hydroxy propionic acid production. *Appl. Microbiol. Biotechnol.* 82: 995-10030.

Jinfeng, Z., Jianping, L., Xiaobo, X. and Peilin, C. (2008) Evaluation of catalysts and optimization of reaction conditions for the dehydration of methyl lactate to acrylates. *Chin. J. Chem. Eng.* 16: 263-269.

Lira, C. T and McCrackin, P. J. (1993) *Ind. Eng. Chem. Res.* 32: 2608-2613

Lunelli, B. H., Rivera, E. C., Vasco de Toledo, E. C., Macial, M. R. W., and Filho, R. M. (2008) *Appl. Biochem. Biotechnol.* 148: 175-187

Mok, W. S-L., and Antal Jr. M. J. (1989) Formation of acrylic acid from lactic acid in supercritical water. *J. Org. Chem.* 54: 4596-4602.

Shi, H. F., Hu, Y. C., Wang, Y., Huang, H. (2007) KNaY-zeolite catalyzed dehydration of methyl lactate. *Chin. Chem. Lett.* 18: 476-478.

Straathof, A. J. J., Sie, S., Franco, T. T. (2005) Feasibility of acrylic acid production by fermentation. *Appl. Microbiol. Biotechnol.* 67: 727-734.

Sun, P., Yu, D., Fu, K., Gu, M., Wang, Y., Huang, H. and Ying, H. (2009) Potassium modified NaY: A selective and durable catalyst for dehydration of lactic acid to acrylic acid. *Catal. Comm.* 10: 1345-1349.

Wadley, D. C., Tam. M. S. Kokitkar, P. B., Jackson, J. E., Miller, D. J. (1997) Lactic acid conversion to 2,3-pentanedione and acrylic acid over silica-supported sodium nitrate: Reaction optimization and identification of sodium lactate as the active catalyst. *J. Catal.* 165: 162-171.

Wang, H., Yu, D., Sun, P., Yan, J. Wang, Y. and Huang, H. (2008) Rare earth metal modified NaY: Structure and catalytic performance for lactic acid dehydration to acrylic acid. *Catal. Comm.* 9: 1799-1803.

Yang, Jung-II, Cho, S-H., Kim, H-J., Joo, H., Jung, H., Lee, K-Y. (2007) Production of 4-hydroxybutyl acrylate and its reaction kinetics over amberlyst 15 catalyst. *Can. J. Chem Eng.* 85: 83-91.

Zhang, J., Lin, J., Cen, P. (2008) Catalytic dehydration of lactic acid to acrylic acid over sulfate catalysts. *Can. J. Chem. Eng.* 86:1047-1053.

Zahng, Z., Qu, Y. Wang, S. and Wang, J. (2009) Catalytic performance and characterization of silica supported sodium phosphates for the dehydration of methyl lactate to methyl acrylate and acrylic acid. *Ind. Eng. Chem. Res.* 48: 9083-9089.

Xhang, Z., Qu, Y., Wang, S., Wang, J. (2010) Theoretical study on the mechanisms of the conversion of methyl lactate over sodium polyphosphate catalysts. *J. Mol. Catal. A: Chem.* 323: 91-100.

Xu, X., Lin, J. and Cen, P. (2006) Advances in the research and development of acrylic acid production from biomass. *Chinese J. Chem. Eng.* 14: 419-427.

B. Q. Xu, T. Yamaguchi, K. Tanabe, Mater. Based on the literature on phenol TPD on silica alumina, MgO and ZrO2 Chem. Phys 1988 19, 291-297.

Zhang, J., Zhao, Y., Pan, M., Feng, X., Ji, W., Au, C-T. (2011) Efficient acrylic acid production through bio lactic acid dehydration over NaY Zeolite modified by alkali phosphates. *ACS Catal.* 1: 32-41.

What is claimed is:

1. A method comprising:
a) providing a solvent and a reactant comprising at least one member selected from the group consisting of an α-hydroxycarboxylic acid, an α-hydroxycarboxylic acid ester, a β-hydroxycarboxylic acid, a β-hydroxycarboxylic acid ester, a cyclic ester thereof, and acetoxylated acid or ester thereof;
b) providing a porous or crystalline aluminosilicate material having surface acidity;
c) treating said porous or crystalline aluminosilicate material with an inorganic salt to reduce said surface acidity at least by 50% as measured by temperature programmed desorption technique;
d) performing a dehydration reaction at above ambient temperature to produce α, β-unsaturated carboxylic acid and/or an α, β-unsaturated carboxylic acid ester with a minimum selectivity of 70%, acetaldehyde with a maximum selectivity of 20%, 2,3-pentadione with a maximum selectivity of less than 1.0%; and propionic acid with a maximum selectivity of less than 1.0%.

2. The process of claim 1, wherein said porous aluminosilicate material comprises aluminum and silicon in the ratio 1:1 to 1:150.

3. The process of claim 1, wherein said inorganic salt is selected from a group consisting of at least one selected from a phosphate, a, sulfate, a nitrate, a carbonate, a halide, a molybdate, a tungstate, a stanate, an antimonite, any combination thereof.

4. The process of claim 1, wherein said porous aluminosilicate material is treated with said inorganic salt through an incipient impregnation process.

5. The process of claim 1, wherein said porous aluminosilicate material is treated with said inorganic salt through a wet impregnation process.

6. The process of claim 1, wherein said inorganic salt is selected from a group consisting of a monosodium phosphate, disodium phosphate, a trisodium phosphate, a potassium phosphate, a sodium aluminum phosphate compound, and any combination thereof.

7. The process of claim 1, wherein a part of said surface acidity of porous aluminosilicate material is Brønsted acidity.

8. The process of claim 1, wherein a part of said surface acidity of porous aluminosilicate material is Lewis acidity.

9. The process of claim 1, wherein said dehydration reaction is carried in the temperature range of 250° C. to 400° C.

10. The process of claim 1, wherein said dehydration reaction is carried with gas hourly space velocity in the range of 4000-40,000/hour.

11. The process of claim 1, wherein said porous aluminosilicate material is a zeolite selected from a group consisting of Zeolite A, Zeolite B, Zeolite L, Zeolite X, Zeolite Y, Zeolite ZK-4, mordenite, beta and Zeolite ZSM-5.

12. The process of claim 1, wherein said porous aluminosilicate material is ZSM-5.

13. The process of claim 1, wherein said porous aluminosilicate material has undergone at least one ion exchange.

14. The process of claim 1, wherein said porous aluminosilicate material has associated therewith at least one ion selected from the group consisting of $H^+$, $Li^+$, $Na^+$, $K^+$, $Cs^+$, $Mg^{2+}$, $Ca^{2+}$, $Ba^{2+}$, $La^{2+}$, $La^{3+}$, $Ce^{2+}$, $Ce^{3+}$, $Sm^{2+}$, $Sm^{3+}$, $Eu^{2+}$, $Eu^3+$, and any combination thereof.

15. The process of claim 1, wherein the dehydration reaction occurs in the presence of a carrier gas selected from a group consisting of carbon dioxide, helium, and nitrogen and any combination thereof.

16. The process of claim 1, wherein the dehydration reaction is performed in a reactor vessel comprising a reactor material comprising at least on selected from the group consisting of titanium, silanized stainless steel, quartz, and any combination thereof.

* * * * *